(12) United States Patent
Hauer et al.

(10) Patent No.: US 8,951,750 B2
(45) Date of Patent: Feb. 10, 2015

(54) MALONATE DECARBOXYLASES FOR INDUSTRIAL APPLICATIONS

(75) Inventors: Bernhard Hauer, Fussgönheim (DE); Nina Schneider, Offenburg (DE); Krzysztof Okrasa, Manchester (GB); Jason Micklefield, Stockport (GB); David Leys, Todmorden (GB); Colin Levy, Rawtenstall (GB)

(73) Assignee: BASF SE, Ludwigshafen (DE)

( * ) Notice: Subject to any disclaimer, the term of this patent is extended or adjusted under 35 U.S.C. 154(b) by 275 days.

(21) Appl. No.: 12/744,937

(22) PCT Filed: Nov. 28, 2008

(86) PCT No.: PCT/EP2008/010131
§ 371 (c)(1),
(2), (4) Date: May 27, 2010

(87) PCT Pub. No.: WO2009/068308
PCT Pub. Date: Jun. 4, 2009

(65) Prior Publication Data
US 2010/0311037 A1    Dec. 9, 2010

(30) Foreign Application Priority Data

Nov. 28, 2007   (EP) .................................... 07023075
May 16, 2008   (EP) .................................... 08156393

(51) Int. Cl.
| | |
|---|---|
| C12Q 1/64 | (2006.01) |
| G01N 33/53 | (2006.01) |
| C07B 37/06 | (2006.01) |
| C12N 9/88 | (2006.01) |
| C07K 14/235 | (2006.01) |

(Continued)

(52) U.S. Cl.
CPC ................ *C12N 9/88* (2013.01); *C07K 14/235* (2013.01); *C12N 9/90* (2013.01); *C12P 7/40* (2013.01); *C12P 7/42* (2013.01); *C12Q 1/00* (2013.01); *C12Y 401/01076* (2013.01); *C07K 2299/00* (2013.01)
USPC ............................... 435/9; 435/7.71; 562/479

(58) Field of Classification Search
None
See application file for complete search history.

(56) References Cited

U.S. PATENT DOCUMENTS 7,981,645 B2 *   7/2011   Aygun et al. .................. 435/146
2010/0144010 A1   6/2010   Aygün et al.

FOREIGN PATENT DOCUMENTS

| EP | PCT/EP2005/001156 | * | 2/2005 |
|---|---|---|---|
| WO | WO-2005/078111 A1 | | 8/2005 |

OTHER PUBLICATIONS

AMDA_BORBO (last viewed on Feb. 27, 2012).*

(Continued)

*Primary Examiner* — Alexander Kim
(74) *Attorney, Agent, or Firm* — Drinker Biddle & Reath LLP

(57) ABSTRACT

The present invention relates to a method for the enzymatic decarboxylation of malonic acid (propanedioic acid) derivatives catalyzed by enzymes structurally and/or functionally related to arylmalonate decarboxylase (AMDase) as isolated from microorganisms of the genus *Bordetella*. The present invention also relates to novel enzymes with a decarboxylase activity, useful for performing the claimed method, mutants thereof, corresponding coding sequences and expression systems, methods of preparing said novel enzymes, and screening methods for obtaining further suitable enzymes also having said decarboxylase activity.

21 Claims, 8 Drawing Sheets (1) : Ar = Ph, R = H
(2) : Ar = Ph, R = CH₃
(3) : Ar = 2-naphthyl-, R = CH₃
(4) : Ar = 2-thienyl-, R = CH₃

(51) Int. Cl.
*C12N 9/90* (2006.01)
*C12P 7/40* (2006.01)
*C12P 7/42* (2006.01)
*C12Q 1/00* (2006.01)

(56) References Cited

OTHER PUBLICATIONS

Okrasa et al., Structure-Guided Directed Evolution of Alkenyl and Arylmalonate Decarboxylases., Angew Chem Int Ed. (2009), vol. 48(41), pp. 7691-7694.*
Guo et al., Protein tolerance to random amino acid change, 2004, Proc. Natl. Acad. Sci. USA 101: 9205-9210.*
Lazar et al., Transforming Growth Factor α: Mutation of Aspartic Acid 47 and Leucine 48 Results in Different Biological Activity, 1988, Mol. Cell. Biol. 8:1247-1252.*
Hill et al., Functional Analysis of conserved Histidines in ADP-Glucose Pyrophosphorylase from *Escherichia coli*, 1998, Biochem. Biophys. Res. Comm. 244:573-577.*
Wacey et al., Disentangling the perturbational effects of amino acid substitutions in the DNA-binding domain of p53., Hum Genet, 1999, vol. 104, pp. 15-22.*
De Luca et al., Molecular cloning and analysis of cDNA encoding a plant tryptophan decarboxylase: comparison with animal dopa decarboxylases., Proc. Natl. Acad. Sci. USA, (1989), vol. 86, pp. 2582-2586.*
Matoishi, K., et al., "Mechanism of Asymmetric Decarboxylation of ∝-aryl-∝-methylmalonate Catalyzed by Arylmalonate Decarboxylase Originated From *Alcaligenes bronchisepticus*", Journal of Molecular Catalysis B: Enzymatic, vol. 27, (2004), pp. 161-168.
Miyamoto, K., et al., "Asymmetric Decarboxylation of Disubstituted Malonic Acid by *Alcaligenes bronchisepticus* KU 1201", Biocatalysis, vol. 5, (1991), pp. 49-60.
Miyamoto, K., et al., "Cloning and Heterologous Expression of a Novel Arylmalonate Decarboxylase Gene From *Alcaligenes bronchisepticus* KU 1201", Appl. Microbiol. Biotechnol., vol. 38, (1992), pp. 234-238.
Miyamoto, K., et al., "Effect of Conformation of the Substrate on Enzymatic Decarboxylation of ∝-Arylmalonic Acid", Bioorganic & Medicinal Chemistry, vol. 2, No. 6, (1994), pp. 469-475.
Miyamoto, K., et al., "Enzyme-Mediated Asymmetric Decarboxylation of Disubstituted Malonic Acids", J. Am. Chem. Soc., vol. 112, (1990), pp. 4077-4078.
Miyamoto, K., et al., "Purification and Characterization of Arylmalonate Decarboxylase From *Achromobacter* sp. KU1311", Journal of Bioscience and Bioengineering, vol. 104, No. 4, (2007), pp. 263-267.
Miyamoto, K., et al., "Purification and Properties of a Novel Arylmalonate Decarboxylase From *Alcaligenes bronchisepticus* KU 1201", Eur. J. Biochem., vol. 210, (1992), pp. 475-481.
Miyamoto, K., et al., Stereochemistry of Decarboxylation of Arylmalonate Catalyzed by Mutant Enzymes, Chemistry Letters, vol. 36, No. 5, (2007), pp. 656-657.
Terao, Y., et al., "Improvement of the Activity of Arylmalonate Decarboxylase by Random Mutagenesis", Appl. Microbiol. Biotechnol., vol. 73, (2006), pp. 647-653.
Terao, Y., et al., "Introduction of Single Mutation Changes Arylmalonate Decarboxylase to Racemase", Chemical Communications, vol. 34, (2006), pp. 3600-3602.
Terao, Y., et al., "Inversion of Enantioselectivity of Arylmalonate Decarboxylase Via Site-Directed Mutation Based on the Proposed Reaction Mechanism", Journal of Molecular Catalysis B:Enzymatic, vol. 45, (2007), pp. 15-20.
"Asp/Glu racemase", Database UniProt Accession No. A6TMI5, Aug. 21, 2007.
"238aa long hypothetical arylmalonate decarboxylase", Database UniProt Accession No. 058713, Aug. 1, 1998.
"Putative decarboxylase", Database UniProt Accession No. Q7WM62, Oct. 1, 2003.
"Asp/Glu racemase", Database UniProt Accession No. Q11DV3, Aug. 22, 2006.
Banerjee, A., et al., "A High-Throughput Amenable Colorimetric Assay for Enantioselective Screening of Nitrilase-Producing Microorganisms Using pH Sensitive Indicators", Journal of Biomolecular Screening, vol. 8, No. 5, (2003), pp. 559-565.
Dimroth, P., et al., "Enzymic and Genetic Basis for Bacterial Growth on Malonate", Molecular Microbiology, vol. 25, No. 1, (1997), pp. 3-10.
Dominguez De Maria, P., et al., "Improved Process for the Enantioselective Hydrolysis of Prochiral Diethyl Malonates Catalyzed by Pig Liver Esterase", Synlett, No. 11, (2005), pp. 1746-1748.
Glavas, S., et al., "Active Site Residues of Glutamate Racemase", Biochemistry, vol. 40, (2001), pp. 6199-6204.
Handa, S., et al., Stereochemical Course of Biotin-Independent Malonate Decarboxylase Catalysis, Archives of Biochemistry and Biophysics, vol. 370, No. 1, (1999), pp. 93-96.
Hoenke, S., et al., "Biosynthesis of Triphosphoribosyl-dephosphocoenzyme A, the Precursor of the Prosthetic Group of Malonate Decarboxylase", Biochemistry, vol. 39, (2000), pp. 13223-13232.
Hwang, K. Y., et al., "Structure and Mechanism of Glutamate Racemase from *Aquifex pyrophilus*", Nature Structural Biology, vol. 6, No. 5, (1999), pp. 422-426.
Janes, L. E., et al., "Quantitative Screening of Hydrolase Libraries Using pH Indicators: Identifying Active and Enantioselective Hydrolases", Chem. Eur. J., vol. 4, No. 11, (1998), pp. 2324-2331.
Kuettner, E.B., et al., "Active-Site Mobility Revealed by the Crystal Structure of Arylmalonate Decarboxylase from *Bordetella bronchiseptica*", Journal of Molecular Biology, vol. 377, No. 2, (2008), pp. 386-394.
Liu, L., et al., "Crystal Structure of Aspartate Racemase from *Pyrococcus horikoshii* OT3 and Its Implications for Molecular Mechanism of PLP-Independent Racemization", J. Mol. Biol., vol. 319, (2002), pp. 479-489.

* cited by examiner (1) : Ar = Ph, R = H
(2) : Ar = Ph, R = $CH_3$
(3) : Ar = 2-naphthyl-, R = $CH_3$
(4) : Ar = 2-thienyl-, R = $CH_3$

AMDase [Bordetella bronchiseptica]
MQQASTPTIGMIVPPAAGLVPADGARLYPDLPFIASGLGLGSVTPEGYDAVIESVV
DHARRLQKQGAAVVSLMGTSLSFYRGAAFNAALTVAMREATGLPCTTMSTAVLNG
LRALGVRRVALATAYIDDVNERLAAFLAEESLVPTGCRSLGITGVEAMARVDTATL
VDLCVRAFEAAPDSDGILLSCGGLLTLDAIPEVERRLGVPVVSSSPAGFWDAVRLA
GGGAKARPGYGRLFDESLEHHHHHH

Asp/Glu racemase [Mesorhizobium sp. BNC1]
(M cleaved off) SAEDPVIGLIVPPAAGLVPPEAVAMYPEVTFHASGLGLKEMTPCGYAGV
IDLVGDHAERHAQAGAQAVALMGTSLSFFRGAAFNAELITHMSNRSGLPATTMSQ
AVVDELKSHGARRIAVVTAYRQDVNNLLAAFLNEHGIEARSLKSLGITSVADVAGTP
AKRLLQLCKEAVHDAGPVDAVLISCGGLHTLDVIVDVEISTGLPVVTSATAGVRGAV
GLLKRSAETAEHATSKFLTGRALEHHHHHH

Hypothetical arylmalonate decarboxylase [Pyrococcus horikoshii OT3]
MYGWRRRIGLIVPSSNTTMEPEFWKMAPEGVSIHTARMRLREVTEESLLEMERHA
KDAALELADAEVDVIVYGCTSGSLIKGKGYDKEIAKNLEEASGIKTITTSTAVLNALN
TLDIQKVVVATPYIDSVNEREKEFLEANGIEVLRIKGLGIVKNTEIGRQEPWVAYKL
ALEVYTPEADGLFISCTNFRTIEIIDKLEVELGVPVVTSNQATMWYALKTMKVKEKY
DMYGTLLKEKLLEHHHHHH

Putative decarboxylase [Bordetella bronchiseptica RB50]
MPTPTQMKTTARYRPYAWRAKVGLIVPSTNTINEPEFYRLAPDGVTIHTGRAINAG
PATQENYDRMARGVLEAADLIKTAEVDVVAYGCTSGSIVCSLDELCDGMSERVGV
PAIATAGAVVAALRALGVRRVAVGTPYIDFVNQREREFLEQYGFEVVSIEGMDLGH
TQEERRDIGRVPPQSTFQLARDIDRPQAEAIFLSCTNLATLDMIERIENELGKPVVT
SNQATFWACLRLLGLSCAIPGYGRLLTDCLAPITRASYALALEHHHHHH

Asp/Glu racemase [Alkaliphilus metalliredigenes QYMF]
(M cleaved off) SDFSYGGRAKIGLIYPAPGWVMEPEFYLMAPWGVSTYTTRISLKHVNVA
ELRKLGDQSVEAAELLAQAPLDVIALGCTSGSFVNGSRYDQELIEKMEGVSGGIPC
TTTSTAVVAALKALHVTKIAVATPYIDEVNLKAKNFLEAEGLDVVNIKGLGLLQDIEI
DRQDMETVYRLAKEVDHVEAQAIVILCTGLRSVPIIEALENDLGKPVISAIQATFWH
CLRLSGVRENVEGYGSLLRIEGLLEHHHHHH

Glutamate racemase [Aquifex pyrophilus]
MKIGIFDSGVGGLTVLKAIRNRYRKVDIVYLGDTARVPYGIRSKDTIIRYSLECAGFL
KDKGVDIIVVACNTASAYALERLKKEINVPVFGVIEPGVKEALKKSRNKKIGVIGTPA
TVKSGAYQRKLEEGGADVFAKACPLFVPLAEEGLLEGEITRKVVEHYLKEFKGKID
TLILGCTHYPLLKKEIKKFLGDVEVVDSSEALSLSHNFIKDDGSSSLELFFTDLSPN
LQFLIKLILGRDYPVKLAEGVFTHLEHHHHHH

Fig.2

```
CLUSTAL W (1.83) multiple sequence alignment

BAA02419.1          --------------MQQASTPTIGMIVPPAAGLVPADGARLYPD-LPFIASG-LGLGSVTP 45
EAN08019.1          --------------MSAEDPVIGLIVPPAAGLVPPEAVAMYPE-VTFHASG-LGLKEMTP 44
NP_888076.1         MPTPTQMKTTARYRPYAWRAKVGLIVPSTNTINEPEFYRLAPDGVTIHTGRAINAGPATQ 60
BAA30082.1          --------------MYGWRRRIGLIVPSSNTTMEPEFWKMAPEGVSIHTAR-MRLREVTE 45
ZP_00801202.1       ----------MSDFSYGGRAKIGLIYPAPGWVMEPEFYLMAPWGVSTYTTR-ISLKHVNV 49
                              :*:* *..      .:       : *  :.  :  :

BAA02419.1          EGYDAVIESVVDHARRLQKQGAAVVSLMGTSLSFYRGAAFNAALTVAMREATG-LPCTTM 104
EAN08019.1          CGYAGVIDLVGDHAERHAQAGAQAVALMGTSLSFFRGAAFNAELITHMSNRSG-LPATTM 103
NP_888076.1         ENYDRMARGVLEAADLIKTAEVDVVAYGCTSGSIVCS---LDELCDGMSERVG-VPAIAT 116
BAA30082.1          ESLLEMERHAKDAALELADAEVDVIVYGCTSGSLIKGKGYDKEIAKNLEEASG-IKTITT 104
ZP_00801202.1       AELRKLGDQSVEAAELLAQAPLDVIALGCTSGSFVNGSRYDQELIEKMEGVSGGIPCTTT 109
                          :   :  *   .     . **  *:  .      :    :   * :   :

BAA02419.1          STAVLNGLRALGVRRVALATAYIDDVNERLAAFLAEESLVPTGCRSLGITGV----EAMA 160
EAN08019.1          SQAVVDELKSHGARRIAVVTAYRQDVNNLLAAFLNEHGIEARSLKSLGITSV----ADVA 159
NP_888076.1         AGAVVAALRALGVRRVAVGTPYIDFVNQREREFLEQYGFEVVSIEGMDLGHTQEERRDIG 176
BAA30082.1          STAVLNALNTLDIQKVVVATPYIDSVNEREKEFLEANGIEVLRIKGLGIVKN----TEIG 160
ZP_00801202.1       STAVVAALKALHVTKIAVATPYIDEVNLKAKNFLEAEGLDVVNIKGLGLLQD----IEID 165
                    : **:  *.:    :!.:  *.* : **      **   . :           ...::

BAA02419.1          RVDTATLVDLCVRAFEAAPDSDGILLSCGGLLTLDAIPEVERRLGVPVVSSSPAGFWDAV 220
EAN08019.1          GTPAKRLLQLCKEAVHDAGPVDAVLISCGGLHTLDVIVDVEISTGLPVVTSATAGVRGAV 219
NP_888076.1         RVPPQSTFQLARDIDRPQ--AEAIFLSCTNLATLDMIERIENELGKPVVTSNQATFWACL 234
BAA30082.1          RQEPWVAYKLALEVYTPE--ADGLFISCTNFRTIEIIDKLEVELGVPVVTSNQATMWYAL 218
ZP_00801202.1       RQDMETVYRLAKEVDHVE--AQAIVILCTGLRSVPIIEALENDLGKPVISAIQATFWHCL 223
                     *.:             :..:.:  * .:  ::      *  :*  * **::: *  .:

BAA02419.1          RLAG-GGAKARPGYGRLFDES------------ 240
EAN08019.1          GLLKRSAETAEHATSKFLTGRA----------- 241
NP_888076.1         RLLG--LSCAIPGYGRLLTDCLAPITRASYALA 265
BAA30082.1          KTMK--VKEKYDMYGTLLKEKL----------- 238
ZP_00801202.1       RLSG--VRENVEGYGSLLRIEGL---------- 244
                      .  ::
```

Fig.3 (a)

```
            Large binding    Small binding        Oxy-anion         Small binding       Active site
              pocket            pocket              holes              pocket              Cys 12 13 14 15 16 17   39 40 41 42 43 44 45 46 47 48 49 50 51   73 74 75 76 77   124 125 126 127 128   154 155 156 157 158 159 160 161 162   186 187 188 189 190 ...

AMDAse         I V P P A A - G L G S V T P E G Y D A V - M G T S L - T A Y I D - T G V E A M A R V - L S C G G L
EAN08019.1     I V P P A A - G L K E M T P C G Y A G V - M G T S L - T A Y R Q - T S V A D V A G T - I S C G G L
NP_888076.1    I V P S T N - N A G P A T Q E N Y D R M - G C T S G - T P Y I D - T Q E E R R D I G - L S C T N L
BAA30082.1     I V P S S N - R L R E V T E E S L L E M - G C T S G - T P Y I D - V K N T E I G R Q - I S C T N F
ZP_00801202.1  I Y P A P G - S L K H V N V A E L R K L - G C T S G - T P Y I D - L Q D I E I D R Q - I L C T G L

MALONATE DECARBOXYLASES FOR INDUSTRIAL APPLICATIONS

RELATED APPLICATIONS

This application is a national stage application (under 35 U.S.C. §371) of PCT/EP2008/010131, filed Nov. 28, 2008, which claims benefit of European application 07023075.0, filed Nov. 28, 2007, and European application 08156393.4, filed May 16, 2008.

SUBMISSION OF SEQUENCE LISTING

The Sequence Listing associated with this application is filed in electronic format via EFS-Web and hereby incorporated by reference into the specification in its entirety. The name of the text file containing the Sequence Listing is Sequence_List_13111_00147_US. The size of the text file is 42 KB, and the text file was created on May 24, 2010.

The present invention relates to a method for the enzymatic decarboxylation of alpha-substituted malonic acid (propanedioic acid) derivatives catalyzed by enzymes structurally and/or functionally related to arylmalonate decarboxylase (AMDase) as isolated from microorganisms of the genus Bordetella, in particular Bordetella bronchiseptica. The present invention also relates to novel enzymes with decarboxylase activity, useful for performing the claimed method, mutants thereof, corresponding coding sequences and expression systems, methods of preparing said novel enzymes, and screening methods for obtaining further suitable enzymes also having said decarboxylase activity.

BACKGROUND OF THE INVENTION

Decarboxylation of malonyl substrates is a common enzymatic transformation that occurs in a number of important biological pathways. For example, numerous aerobic and anaerobic bacteria can grow on malonate as the sole carbon source, because they possess malonate decarboxylase systems that transform malonate or malonyl-CoA to acetate.[1] Most of these archetypicali malonate decarboxylases are multienzyme systems involving acyl carrier proteins (ACPs) with unusual prosthetic groups as well as biotin dependent decarboxylases.[2] Decarboxylation of malonyl units also occurs during the Claisen-type condensation reaction catalysed by β-ketoacyl ACP synthase (KAS) enzyme and domains within fatty acid and polyketide synthases.

An arylmalonate decarboxylase (AMDase) was isolated from the gram-negative bacterium, Alcaligenes bronchisepticus (Bordetella bronchiseptica),[3,4] which catalyzes the enantioselective decarboxylation of α-aryl-α-methylmalonates to give optically pure α-arylpropionates. Whilst the biological role of the enzyme has not been established, it has been shown to be a robust catalyst decarboxylating a range of substrates including: phenylmalonic acid 1; 2-methyl-2-phenylmalonic acid 2; 2-methyl-2-naphthyl malonic acid 3 and 2-thienylmalonic acid 4 (see FIG. 1 (a)).[5] The AMDase is unusual amongst malonate decarboxylases[6] as it does not require biotin or any other co-factors for activity. In addition, decarboxylation does not involve formation of a malonyl thioester-enzyme intermediate[7] which is a common driving force for several malonate decarboxylases.[1,2] The mechanism of the enzyme is thus of considerable interest. The chiral carboxylic acid products of the AMDase are also potentially attractive for industrial applications, particularly as precursors for pharmaceutical synthesis.

AMDase from B. bronchiseptica (SEQ ID NO:2) shows sequence similarity with a number of racemases and isomerases.[7,8] Moreover the putative catalytic cysteine is preserved in all enzymes as shown by sequences alignment. However no AMDase activity was reported for those enzyme and AMDase from B. bronchiseptica (SEQ ID NO:2) remained the only enzyme capable to catalyze the decarboxylation of α-arylmalonates to α-arylpropionates.

In the case of the glutamate and aspartate racemases two cysteine residues are located on either side of the amino acid substrate in the active site. Indeed, it was discussed that the two cysteine residues function in general acid-base catalysis, abstracting the α-proton from the substrate to generate a planar enolate which is re-protonated from the opposite face leading to the racemate.[9,10] In the case of the AMDase, a single active site Cys residue (Cys188) has been shown to play a crucial role in enzyme catalysis. This led to the proposal that the mechanism of the AMDase is similar to the racemases. For example, decarboxylation of the substrate 2-methyl-2-phenylmalonate is suggested to result in an enolate anion, which is protonated on the si-face by Cys188 to form a R-configured α-phenylpropionate product.[8] To support the mechanistic similarity with the racemase family, the introduction of second cysteine, guided by sequence alignment,[8] resulted in a AMDase single point mutant (G74C), which was capable of racemising homochiral α-arylpropionates, albeit with very low catalytic efficiencies.[7] In addition the double mutation G74C/C188S, which was predicted to reposition the key active site Cys on the opposite face of the enolate intermediate, led to an enzyme with opposite enantioselectivity. Once again the catalytic efficiency of this mutant was several orders of magnitude lower than the wild type AMDase.[11]

WO 2005/07811 provides specific examples of mutants of and AMDase enzyme isolated from B. bronchiseptica KU1201 carrying up to two mutated amino acid residues. The following mutants with altered enzyme activity are suggested: A84G, F85A, A87G, R94A, T103A, I127A, (F85A, R173A), (F85A, E176A) and (F85A, A178G); The following mutants with improved thermostability are suggested: P15A, P32A, G74A, T75A, D128A, D163A, A165G and C171A. Generically, mutations in at least one of the positions 17, 19, 22, 24, 25, 32, 41, 42, 46, 47, 53, 60, 61, 63, 68, 74, 83, 84, 85, 87, 94, 103, 105, 112, 116, 119, 121, 139, 142, 155, 168, 171, 173, 178, 199, 201, 202, 203, 204, 205, 210, 221, 222, 224, 225, 226, 227, 228, 229, 230, 235, 238, 239 and 240 are mentioned. However, said document neither discloses the entire crystal structure of said mutants or of the parent AMDase or the structural organization of the catalytic site of such enzymes, nor does said document teach or suggest that AMDase activity might be associated with proteins of different origin. The document speculates about further "product structures" which might be accessible via enzyme mutants disclosed therein. However, enzyme activities of a limited number of mutants were merely reported for phenyl malonic acid and alpha-hydroxy-(4-methylphenyl) malonic acid. No hydrocarbyl-substituted, in particular no alkenyl-substituted malonic acid derivatives have been suggested or even tested.

Further enzymes with AMDase activity, so far, have not been described in the art.

There is therefore a need for alternative, optionally improved enzymes with AMDase activity, which potentially are applicable in industrial processes for preparing preferably optically pure decarboxylation products of malonic acid derivatives, as for example α-arylpropionates, and which do not require biotin or any other co-factors for decarboxylase activity.

There is also a need for identifying novel malonate decarboxylase enzyme with extended or altered/modified substrate specificity, i.e. enzymes decarboxylating malonate derivatives different from alpha-aryl malonates, which potentially are applicable in industrial processes for preparing preferably optically pure alpha-substituted monocarboxylic acids from corresponding malonate substrates.

There is also a need for functional mutants derived from such enzymes with AMDase activity or enzymes with extended or altered/modified substrate specificity, which potentially are applicable in industrial processes for preparing preferably optically pure mono-carboxylic acids from malonate substrates. Said functional mutants may be adapted to the preferred or exclusive decarboxylation of malonate substrates different from aryl malonates, as for example non-aromatic alpha-substituted malonate derivatives, like alkenyl-substituted malonates.

It is therefore an object of the present invention to provide such alternative or optionally improved enzymes with malonate decarboxylase activity (MDase activity) as mentioned above.

SUMMARY OF THE INVENTION

The above-mentioned problems could, surprisingly, be solved by identifying further enzymes for which an AMDase activity or MDase activity so far has not been described.

In particular, the present inventors identified a crystal structure of the AMDase from B. bronchiseptica (SEQ ID NO:2), and performed $^{18}O$ labelling studies which allow the detailed molecular mechanism of this interesting decarboxylase to be demonstrated. Based on this the present inventors were able to identify further industrially suitable AMDase enzymes. For example, an enzyme from Mesorhizobium sp. BNC1 (SEQ ID NO:4) was identified, which is shown to have a structure, stereochemistry, mechanism and catalytic efficiencies similar to AMDase from B. bronchiseptica. The present inventors also observed extended or modified substrate specificity and/or enzyme activity (if compared to the parent enzyme) for such enzymes, allowing the biocatalytic conversion of further alpha-substituted malonate derivatives. Based on said studies the present inventors were also able to provide functional engineered mutants of said enzymes.

DESCRIPTION OF THE FIGURES

FIG. 2: Sequences of purified enzymes with C-terminal His$_6$-tag as determined after ESI-MS analysis. Sequences shown are AMDase [Bordetella bronchiseptica] (SEQ ID NO: 2); Asp/Glu racemase [Mesorhizobium sp. BNC1] (SEQ ID NO: 4); Hypothetical arylmalonate decarboxylase [Pyrococcus horikoshii OT3] (SEQ ID NO: 6); Putative decarboxylase [Bordetella bronchiseptica RB50] (SEQ ID NO: 8); Asp/Glu racemase [Alkaliphilus metalliredigenes QYMF] (SEQ ID NO: 10 and Glutamate racemase [Aquifex pyrophilus] (SEQ ID NO: 12).

FIG. 3. (a) Sequence alignment of AMDase from B. bronchiseptica (BAA02419.1, SEQ ID NO: 2) (upper line) and examples of structurally and functionally related enzymes from different microorganisms: Mesorhizobium sp. BNCI (EAN08019.1, SEQ ID NO: 4), Bordetella bronchiseptica RB50 (NP 888076.1, SEQ ID NO: 8), Pyrococcus horikoshii OT3 (BAA30082.1, SEQ ID NO: 6) and Alkaliphilus metalliredigenes QYMF (ZP_00801202.1, SEQ ID NO: 10)

(b) alignment of functionally related sequence regions of AMDase from B. bronchiseptica (SEQ ID NO: 2) (upper line) and examples of structurally and functionally related enzymes from different microorganisms. Sequences shown are (EAN08019.1, SEQ ID NO: 4); (NP_888076.1, SEQ ID NO: 8); (BAA30082.1, SEQ ID NO: 6); and (ZP_00801202.1, SEQ ID NO: 10).

Figure 4:
Figure 4:
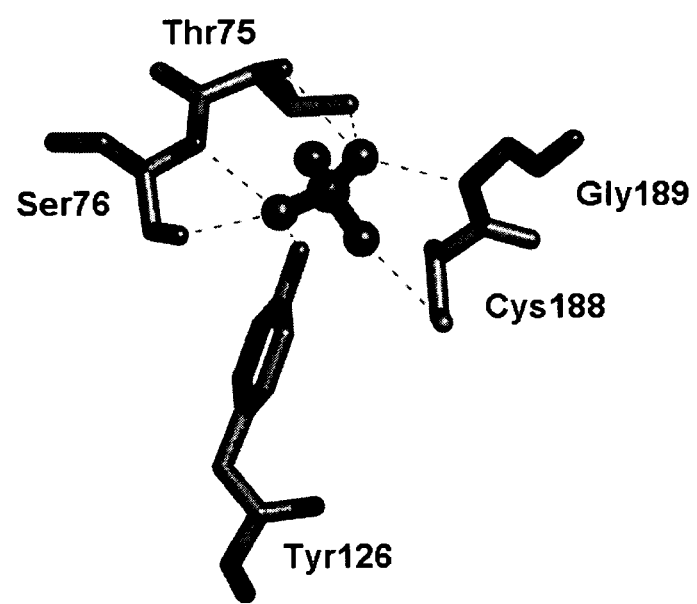

FIG. 4: (a) Cartoon representation of AMDase crystal structure with highlighted: phosphate and Cys188. (b) AMDase active site with bound phosphate and hydrogen bonding pattern observed to $O_1$, $O_2$ and $O_3$ of phosphate.

Figure 5:
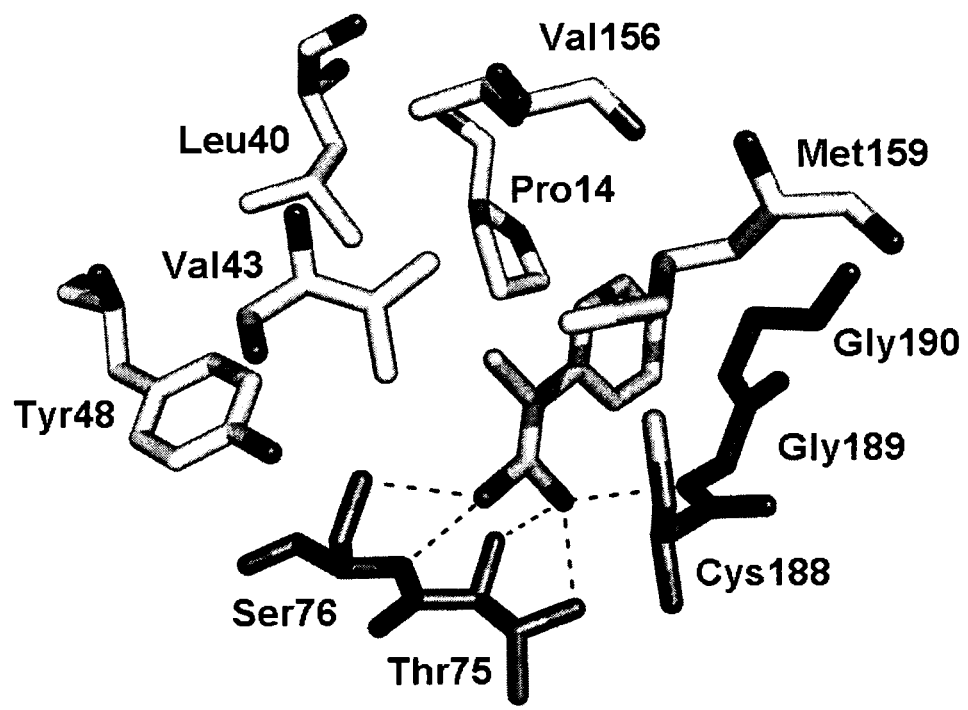

FIG. 5: Active site of AMDase with residues Lys40, Val43, Tyr48, Val156, Pro14, Met159 associated in building the smaller binding pocket (lighter colour) surrounding methyl group of intermediate enolate bound to the oxy-anion hole residues Ser76, Thre75, Gly189 (darker colour) and in proximity to the catalytic site Cys188.

Figure 6:
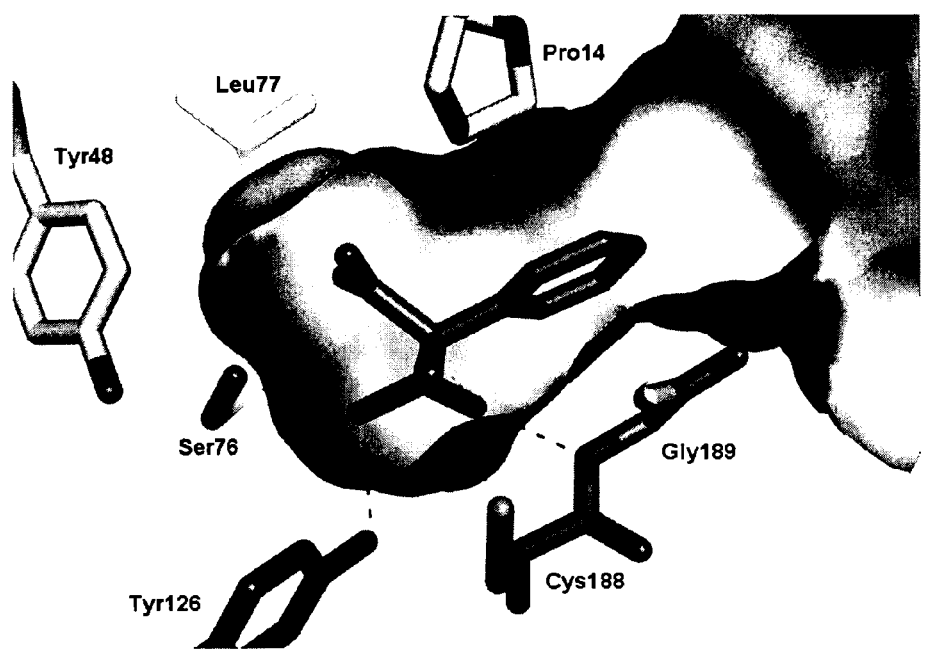
Figure 6:
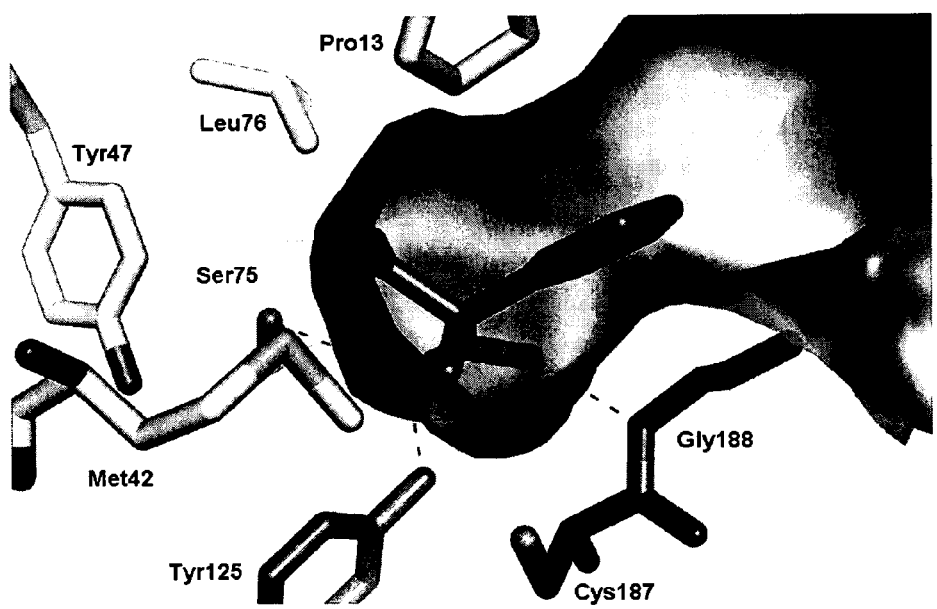

FIG. 6: (a) Cross sections of the B. bronchiseptica AMDase active site with solvent accessible surface showing a model of 2-methyl-2-phenylmalonate situated in the binding pockets. Residues building oxy-anion hole are darker and residues building hydrophobic pockets lighter. (b) Active site of Mesorhizobium sp. BNCI AMDase.

Figure 7:
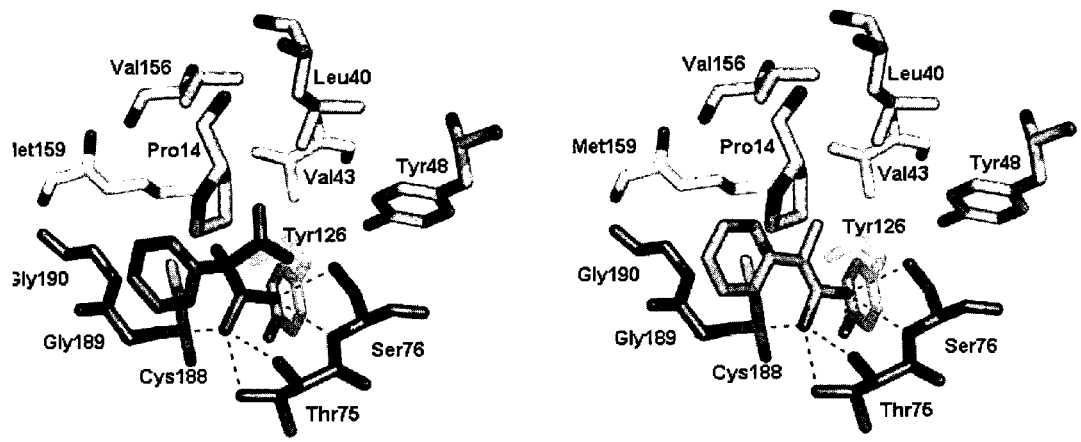

FIG. 7: Orientation of 2-methyl-2-phenylmalonate (left) and the enolate (right) in the active site of AMDase.

Figure 8:
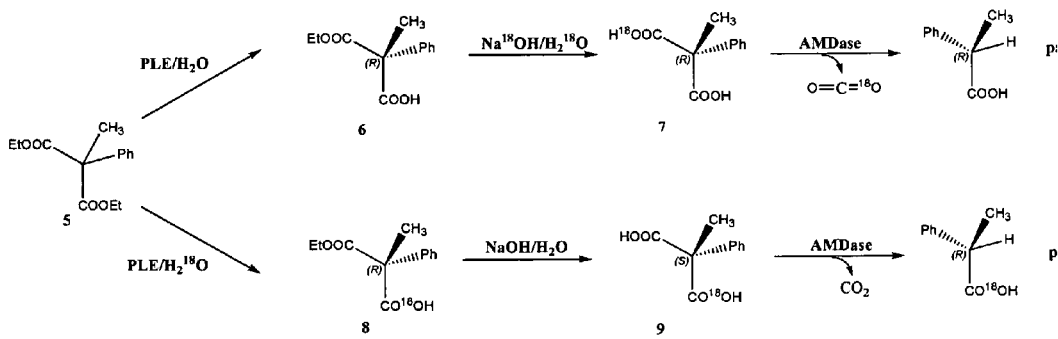

FIG. 8: Determination of AMDase stereochemistry using $^{18}O$ labelled water.

Figure 9:
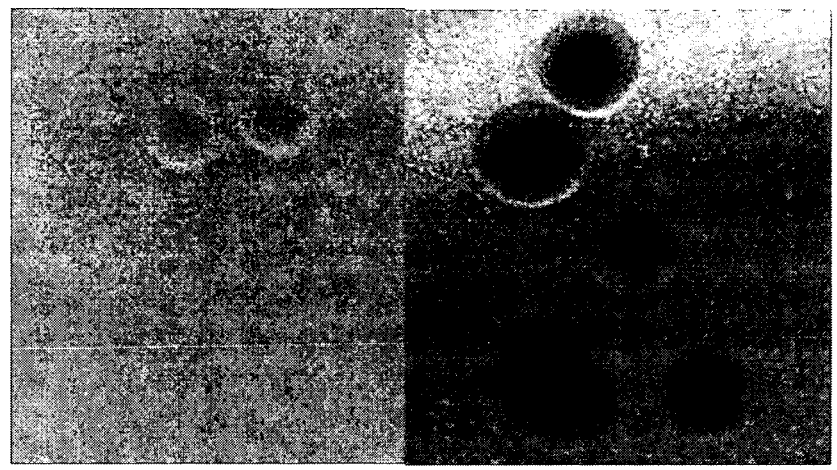

FIG. 9: In vivo assay for AMDase activity using 2-methyl-2-phenylmalonate as a substrate, left picture—colonies of E. coli containing pET30b vector without gene of AMDase, right picture—containing pET30b vector with the gene.

Figure 10:
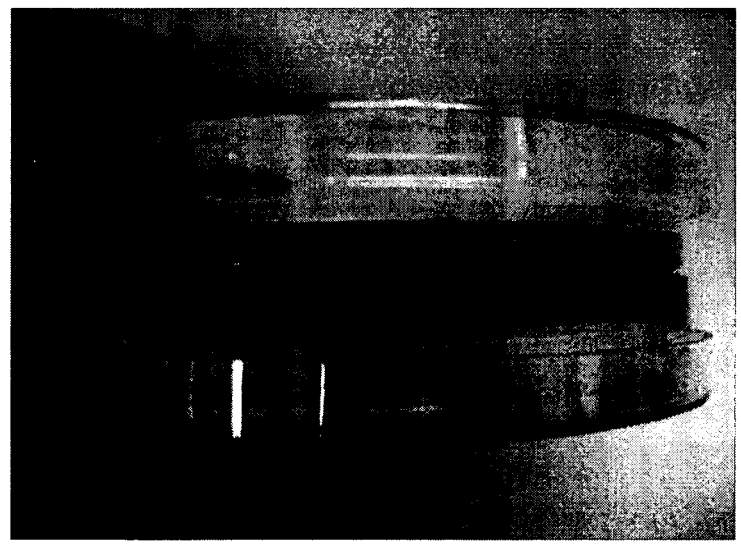

FIG. 10: In vivo assay for AMDase activity using 2-methyl-2-phenylmalonate as a substrate. Top plate—BL21 (DE3) containing pET30b, bottom plate—BL21(DE3) containing pET30b with AMDase gene.

DETAILED DESCRIPTION OF THE INVENTION

1. Preferred Embodiments

A first aspect of the invention relates to a biocatalytic method of decarboxylating an alpha-substituted malonate compound of formula I,

HOOC—C(R$^1$)(R$^2$)—COOH        (I)

or a salt form thereof,
wherein
residue R$^1$ represents a mono- or bicyclic, optionally 1-, 2- or 3-fold substituted, ring, which is for example an optionally substituted, in particular monocyclic, aromatic or heteroaromatic ring; or a non-aromatic, in particular mono- or bicyclic ring optionally carrying one or two carbon-carbon double bonds within its ring; and
residue R$^2$ represents H, OH, SH, NH$_2$, lower alkoxy, lower alkylthio, lower alkyl, lower alkenyl, lower alkynyl or hydroxyl-lower alkyl, in particular OH, SH or lower alkyl
which method comprises
  a) contacting at least on compound of formula I, in the form of any stereoisomer mixture or in optically pure form, with
    (i) a protein having malonate decarboxylase activity, in particular arylmalonate decarboxylase activity, and comprising an amino acid sequence having a sequence identity of 100% or less or, in particular, of less than 99%, as for example less than 98, 97, 96 or 95%, but of at least 25%, as for example at least 30, 35, 40, 45, 50, 60, 70, 80 or 90% sequence identity, for example 25 to 98, 30 to 97, 30 to 95, 30 to 90 or 30 to 80 or 30 to 70 or 30 to 70% sequence identity to the *Bordetella bronchiseptica* protein of SEQ ID NO: 2 (residues 1 to 240) (Blast database entry BAA02419.1) or (ii) a protein having malonate decarboxylase activity, in particular arylmalonate decarboxylase activity and comprising an amino acid sequence having a sequence identity of 100% or less as for example less than 99%, as for example less than 98, 97, 96 or 95%, but of at least 25%, as for example at least 30, 35, 40, 45, 50, 60, 70, 80 or 90% sequence identity, for example 25 to 98, 30 to 97, 30 to 95, 30 to 90 or 30 to 80 or 30 to 70 or 30 to 70% sequence identity to the *Aquifex pyrophilus* protein of SEQ ID NO: 12 (residues 1 to 254) (Blast database entry AAF25672)

b) and optionally isolating at least one decarboxylation product of a compound of formula I, preferably one particular stereoisomer of the reaction product.

In another alternative embodiment the present invention provides a method of the above type for decarboxylating a compound of formula I, or a salt form thereof, wherein residue $R^1$ represents a linear or branched mono- or poly-unsaturated lower alkenyl group optionally carrying one or more cyclic substituents; as for example being substituted by one or more, preferably one, mono- or bicyclic, optionally substituted aromatic or non-aromatic rings; or wherein two, for example terminal, substituents of the lower alkenyl group form together a carbo- or heterocyclic, saturated or unsaturated, aromatic or in particular non-aromatic ring, as for example cycloalkylidene residues as defined herein; and residue $R^2$ represents H, OH, SH, $NH_2$, lower alkoxy, lower alkylthio, lower alkyl, lower alkenyl, lower alkynyl or hydroxyl lower alkyl, in particular, OH, SH or lower alkyl.

According to said alternative embodiment the enzyme activity applied is an MDase activity as defined herein.

In a particular group of compounds of formula I, or a salt form thereof, residue $R^1$ represents a linear or branched mono-unsaturated lower alkenyl group optionally substituted by a mono- or bicyclic, optionally substituted ring, and residue $R^2$ is a lower alkyl group.

In particular, compounds are to be mentioned, wherein $R^1$ represents a linear $C_1$-$C_6$-alken-1-yl group optionally substituted by a mono- or bicyclic, optionally substituted ring, and residue $R^2$ is a $C_1$-$C_6$-alkyl group.

For example, residue $R^1$ represents a linear $C_1$-$C_6$-alken-1-yl group, like ethenyl, propen-1-yl or buten-1-yl, and residue $R^2$ is a $C_1$-$C_6$-alkyl group. Optionally said residue $R^1$ may be further substituted by a mono- or bicyclic, in particular, monocyclic, aromatic or non-aromatic ring. Said ring group, which may preferably be aromatic, and may be a group as defined below, may be further substituted by 1, 2 or 3 optional substituents also as defined below. Optionally said residue $R^1$ may also be terminally substituted by In another embodiment compounds have to be mentioned, wherein $R^1$ represents a linear $C_1$-$C_6$-alken-1-yl group terminally substituted by a cycloalkylidene ring, optionally in turn substituted, and residue $R^2$ is a $C_1$-$C_6$-alkyl group.

As non-limiting examples of compounds of formula I there may be mentioned: 2-phenyl-malonic acid, 2-ethenyl-malonic acid, 2-propen-1-yl-malonic acid, 2-buten-1yl-malonic acid, 2-(cyclohexylidenemethyl)malonic acid, 2-cyclohexen-1-yl-malonic acid; and the corresponding methylmalonic acid compounds.

Preferably said methods comprise a decarboxylation reaction, which is a stereoselective mono-decarboxylation.

Preferably, an optically pure substituted product of the formula II $$HC(R^1)(R^2)\text{—COOH} \qquad (II)$$

or a salt form thereof is obtained, wherein residue $R^1$ and $R^2$ are as defined above.

A non-limiting example of a method of the invention may be illustrated by the following scheme:

$R^3$=H, $CH_3$
$R^4$=H, $CH_3CH_2$
Me=$CH_3$ wherein an alpha-disubstituted malonate III is biocatalytically mono-decarboxylated to form, in high enantioselectivity, the corresponding mono-carboxylic acid IV.

A further non-limiting example of a suitable method refers to the decarboxylation of compounds of formula III to form compounds of formula IV, wherein the Me (i.e. methyl) substituent in alpha position is replaced by SH, or, in particular, OH.

A skilled reader will recognize that the present invention is not limited to the preferred decarboxylation reactions as described herein. As enzymatic reactions, in principle, are reversible reactions, the present invention also covers the corresponding reverse reaction, i.e. the carboxylation reactions, with compounds of formula II as substrate and malonates of formula I as products.

In a preferred embodiment, the protein having AMDase or MDase activity and showing an amino acid sequence identity of 100% or less or, in particular, of less than 99% to the *Bordetella bronchiseptica* protein of SEQ ID NO: 2 forms a substrate pocket having the ability to carry a substrate molecule of formula I, and comprising in functional arrangement the following structural elements a) a Cystein containing catalytic site (CS), the Cystein residue of which is able to interact with the substrate, in particular by transferring a proton to the substrate forming an enolate intermediate, b) an oxy-anion hole (OAH), comprising a plurality of polar amino acid side chains interacting with the carboxylic group of the substrate not to be cleaved off.

In addition said substrate pocked may further comprise c) a large binding pocket (LBP) interacting with the cyclic, preferably aromatic or heteroaromatic, residue $R^1$ and d) a small binding pocket (SBP) interacting with residue $R^2$.

As further illustrated by the attached figures, the analysis of the crystal structure of the AMDase enzyme of *B. bronchiseptica* (SEQ ID NO:2) allowed the identification of individual amino acid residues or amino acid sequence portions involved in the formation of the reactivity centre of the enzyme, so that a model system or reference enzyme for suitable further enzymes with AMDase or MDase activity and functional mutants derived there from could be established.

In particular, for said specific reference enzyme certain "key amino acid residues" could be identified, which are predicted to be involved in the formation of functionally distinct portions of the substrate pocket. Said functionally distinct portions are designated catalytic site (CS), oxy-anion hole (OAH) small binding pocket (SBP) and large binding pocket (LBP).

A first functional portion is CS and a key amino acid residue is Cys188. Moreover, it was found that sequence portions not adjacent to each other in the primary amino acid sequence, are nevertheless functionally related, by contributing to the same functional portion of the binding pocket. Thus, is was observed that the functional portion OAH is formed by at least two distinct sequence portions, which were designated OAH1 and 2 comprising key amino acid residues as described below.

OAH1 Thr75, Gly189
OAH2 Ser76, Tyr126

It was also observed that said reference enzyme forms the binding pocket regions SBP and LBP the amino acid residues associated therewith may be further subdivided in accordance with their preferential orientation with respect to the substrate of formula I attached to the enzyme.

LBP may be subdivided into LBP 1 and LBP2 characterized by the following key residues:

LBP1 Pro14, Pro15, Gly189, Gly190, Met104
LBP2 Val13, Met73, Pro21, Ser212

LBP1 residues are located around cyclic group ($R^1$) of the substrate, while LBP2 residues are building rest of big binding pocket).

SBP may be subdivided into SBP 1 and SBP2 characterized by the following key residues:

SBP1 Lys40, Val43, Tyr48, Leu77, Val156, Pro14, Gly74
SBP2 Val156, Met159, Val43

SBP1 residues form the bigger part of small binding pocket around the leaving carboxyl group of the substrate, while SBP2 residues are building the smaller part of said binding pocket around the less bulky residue ($R^2$) of the substrate.

Based on this analysis a highly characteristic sequence pattern could be developed, by means of which further candidates of proteins with the desired enzymatic activity may be searched, and actually could be found by the inventors. Examples of such newly recognized AMDase or MDase enzymes and corresponding portions of their amino acid sequences, which also show said characteristic sequence pattern, are shown in the alignment of FIG. 3(b). A characteristic sequence pattern of key amino acid residues (i.e. a subgroup of said key amino acids) may be derived from said alignment. Said subgroup comprises in particular:

Pro14, Thr75, Ser76, Tyr126, Cys188 or combinations of 3 or 4 of these residues, as for example:

Thr75, Ser76, Tyr126, Cys188
Pro14, Thr75, Ser76, Cys188

Searching for further candidate enzymes and/or mutants by applying said sequence pattern would also be encompassed by the present invention. It will be understood by a skilled reader that the above sequence pattern is not limited by the exact distances between two adjacent amino acid residues of said pattern. Each of the distances between two neighbours in the above patterns may, for example, vary independently of each other by up to ±10, ±5, ±3, ±2 or ±1 amino acid positions without substantially affecting the desired enzymatic activity.

In view of the close spatial proximity individual key amino acid residues may be allocated to more than one of said above-mentioned sequence portions (see for example amino acids in position 14, 43, 74, 75, 189).

In line with said above functional and spatial analysis of individual amino acid residues based on the crystallographic data as obtained according to the present invention, unique partial amino acid sequences characteristic of potentially useful enzymes with aryl malonate or malonate decarboxylase activity of the invention may be identified.

According to a further preferred embodiment the enzymes of the invention as preferred partial amino acid sequences the may be mentioned a) the Cystein containing catalytic site sequence "CSS", which is formed by a sequence region corresponding to residues 186 to 191 of SEQ ID NO: 1 which shows the following sequence pattern:

```
"CSS"
(S/L)C (G/T)(G/N)       (SEQ ID NO: 13)
``` and b) the oxy-anion hole forming sequences "OAH1S" and "OAH2S" corresponding to residues 73 to 77 and 124 to 128, respectively of SEQ ID NO: 1, which show the following two sequence pattern:

```
"OAH1S"
(M/G)(G/C)TS(L/G)       (SEQ ID NO: 14)

"OAH2S"
T(A/P)Y(I/R)(D/Q)       (SEQ ID NO: 15)
``` wherein in OAH2S the first and/or last amino acid residue may be missing.

Specific examples of suitable partial sequences CSS, OAH1S and OAH2S can be derived from FIG. 3 (b).

According to a further embodiment said structural elements CSS, OAH1S and OAH2S are arranged in the amino acid chain in the following sequential (N->C) order:

OAH1S-OAH2S-CSS and wherein said structural elements are linked together via amino acid sequences independently of each other comprising one or more amino acid residues.

In particular, said structural elements CSS, OAH1S and OAH2S may be arranged in the amino acid chain in the following sequential (N->C) order:

OAHS1-sp1-OAHS2-sp2-CS wherein sp1 and sp2 are linking amino acid sequences with the following approximate sequence length sp1 43-47 amino acids
sp2 55-57 amino acids.

As further preferred partial amino acid sequences the may be mentioned c) the large binding pocket sequence "LBPS" which is formed by a sequence region corresponding to residues 12 to 17 of SEQ ID NO: 1 and which shows the following sequence pattern:

```
"LBPS"
IVP(P/S/A)(A/T/S/P)(A/N/G)    (SEQ ID NO: 16)
```

Specific examples of suitable partial sequences LBPS can be derived from FIG. 3 (b).

In particular, said structural elements CSS, OAH1S, OAH2S and LBPS may be arranged in the amino acid chain in the following sequential (N->C) order:

LBPS-sp3-OAHS1-sp1-OAHS2-sp2-CS wherein sp1, sp2 and sp3 are linking amino acid sequences with the following approximate sequence length sp1 43-47 amino acids
sp2 55-57 amino acids
sp3 57-62 amino acids.

A skilled reader will recognize that mutants of the specific decarboxylase enzymes as disclosed herein may be engineered in order to alter their substrate spectrum (substrate specificity) or improve their enzyme activity vis-á-vis a certain substrate (if compared to the parent enzyme). Said mutations (amino acid substitutions, additions, deletions, insertion, inversions) may also be performed within the structural elements as defined herein above. Particular mutants may comprise 1 to 10, in particular 1, 2, 3, 4 or 5 simultaneous mutations in one or more of said structural elements. Non-limiting examples of suitable mutations will be given below.

A skilled reader will also recognize that additional single or multiple mutations may be performed in regions of the amino acid sequence of a decarboxylase enzyme as disclosed herein, which are not related to said structural elements, and, therefore, do not contribute to the substrate pocket or catalytic site of the enzyme, and, therefore are less critical to enzyme activity or substrate specificity. Guided by the technical teaching of the present invention (as for example the sequence alignments presented herein) a skilled reader will easily identify such regions open to more extensive modifications. For example, a skilled reader will be enabled to perform 1 to 30, 2 to 20 or 5 to 10 simultaneous mutations in such regions without running an unforseeable risk of negatively affecting enzyme activity and/or substrate specificity.

A skilled reader will also recognize that additional single or multiple mutations may be performed in regions of the amino acid sequence of a decarboxylase enzyme as disclosed herein, which, although not building the substrate pocket or active site, may influence the shape of said regions, and, therefore, may influence enzyme activity and/or substrate specificity. Guided by the technical teaching of the present invention (as for example the sequence alignments presented herein) a skilled reader will easily identify such regions as well. For example, a skilled reader will be enabled to perform 1 to 30, 2 to 20 or 5 to 10 simultaneous mutations in such regions. As a non-limiting example of such an amino acid residue of the *Bordetella bronchiseptica* protein of SEQ ID NO: 2 is Leu191, which may be altered (replaced by any other amino acid residue) or deleted in order to influence the shape of active site and/or binding pocket of the enzyme.

According to a further embodiment of the method of the invention, the protein having AMDase or MDase activity is selected from the group consisting of
 a) a protein comprising amino acid residues 2 to 241 of SEQ ID NO: 4 and originating from *Mesorhizobium* sp. BNC1 (Blast database entry EAN08019.1);
 b) a protein comprising amino acid residues 2 to 240 of SEQ ID NO: 6 and originating from *Pyrcoccus horikoshii* OT3 (Blast database entry BAA30082.1);
 c) a protein comprising amino acid residues 2 to 267 of SEQ ID NO: 8 and originating from *Bordetella bronchiseptica* RB50 (Blast database entry NP_888076.1);
 d) a protein comprising amino acid residues 2 to 246 of SEQ ID NO: 10 and originating from *Alkaliphilus metalliredigenes* QYMF (Blast database entry ZP_00801202.1); and
 e) proteins having arylmalonate or malonate decarboxylase activity and having a sequence identity less than 100% to one of the sequences of a), b), c) or d).

Identifying novel proteins having arylmalonate decarboxylase activity from *Aquifex* and *Pyrococus* is very promising, since those organisms are thermophilic, thus the enzymes are expected to be also thermo stabile. Consequently, the present invention also provides novel thermo stabile proteins having arylmalonate or malonate decarboxylase activity and corresponding stabile proteins mutants and derivatives.

According to a further preferred embodiment the decarboxylation reaction is performed with isolated or purified, optionally immobilized decarboxylase as defined herein, or by culturing a microorganism expressing said decarboxylase enzyme activity in the presence of a compound of formula I.

The present invention also relates to a protein having a decarboxylase activity as defined herein, and showing a sequence identity of less than 99%, as for example less than 98, 97, 96 or 95%, but of at least 25%, as for example at least 30, 35, 40, 45, 50, 60, 70, 80 or 90% sequence identity, for example 25 to 98, 30 to 97, 30 to 95, 30 to 90 or 30 to 80 or 30 to 70 or 30 to 70% sequence identity to the *Bordetella bronchiseptica* protein comprising amino acid residues 1 to 240 of SEQ ID NO: 2.

The present invention also relates to a protein having a decarboxylase activity as defined herein, selected from
 a) a protein comprising amino acid residues 1 to 241 of SEQ ID NO: 4 and originating from *Mesorhizobium* sp. BNC1;
 b) a protein comprising amino acid residues 1 to 240 of SEQ ID NO: 6 and originating from *Pyrcoccus horikoshii* OT3;
 c) a protein comprising amino acid residues 1 to 267 of SEQ ID NO: 8 and originating from *Bordetella Bronchiseptica* RB50;
 d) a protein comprising amino acid residues 1 to 246 of SEQ ID NO: 10 and originating from *Aklaliphilus metalliredigenes* QYMF; and
 e) a protein comprising amino acid residues 1 to 256 of SEQ ID NO: 12 and originating from *Aquifex pyrophilus*.

as well as mutants thereof having a decarboxylase activity as defined herein, which mutant having a sequence identity less than 100% or less as for example less than 99%, as for example less than 98, 97, 96 or 95%, but of at least 25%, as for example at least 30, 35, 40, 45, 50, 60, 70, 80 or 90% sequence identity, for example 25 to 98, 30 to 97, 30 to 95, 30 to 90 or 30 to 80 or 30 to 70 or 30 to 70% sequence identity to the corresponding parent protein.

For example, a protein having the desired decarboxylase activity selected from the group consisting of a protein originating from *Mesorhizobium* sp. BNC1 and a protein originating from *Bordetella bronchiseptica* as defined hereinabove, may be used to decarboxylate compounds of the above-identified type wherein residue $R^1$ represents a linear or branched mono- or poly-unsaturated lower alkenyl group optionally substituted by a mono- or bicyclic, optionally substituted ring as defined above, and residue $R^2$ represents H, OH, SH, $NH_2$, lower alkoxy, lower alkylthio, lower alkyl, lower alkenyl, lower alkynyl or hydroxyl lower alkyl, in particular lower alkyl.

In particular said mutants of proteins of SEQ ID NO: 2, 4, 6, 8 and 10 still comprise part or all of the key amino acid residues and/or structural elements CSS, OAH1S, OAH2S and LBPS as defined above.

Non-limiting examples of further potentially applicable mutations are for example disclosed in WO2005/078111, FIG. 2 for proteins of SEQ ID NO:2, the disclosure of which document is herewith incorporated by reference. By aligning said sequence with structurally related, newly screened proteins with AMDase activity of the invention (see for example FIG. 3 (*a*)) a skilled reader will be enabled to deduce suitable mutants form newly obtained enzymes with AMDase activity as well. Such deduced mutants may either have substantially the same enzyme characteristics, as for example enzymatic activity, substrate specificity, stereo specificity, stability, solubility, as the corresponding non-mutated parent enzyme, or have modified enzyme characteristics, as for example modified, i.e. increased or diminished enzymatic activity, catalytic efficiency, stability, solubility, stereo specificity, and/or modified, i.e. broader or narrower substrate specificity.

With respect to the *Bordetella bronchiseptica* protein of SEQ ID NO: 2 non-limiting examples of key amino acid substitution are listed below.

| Structural portion | Key amino acid | Mutation |
|---|---|---|
| LBP1 | Pro14, | Gly, Ala, Val |
| | Pro15, | Gly, Ala, His |
| | Gly189, | Ala, Val, Del[1)] |
| | Gly190, | Ala, Val, Ser, Del[1)] |
| | Met104 | |
| LBP2 | Val13, | Gly, Ala |
| | Met73, | |
| | Pro21, | |
| | Ser212 | |
| SBP1 | Leu40, | Ala, Gly |
| | Val43, | Ala, Gly |
| | Tyr48, | |
| | Leu77, | |
| | Val156, | Ala |
| | Pro14, | Gly, Ala, Val |
| | Gly74 | Cys |
| SBP2 | Val156, | Ala |
| | Met159, | Gly, Ala, Val, Ser, Cys |
| | Val43 | Ala, Gly |
| OAH1 | Thr75 | |
| | Gly189, | Ala, Val, Del[1)] |
| OAH2 | Ser76, | |
| | Tyr126, | Lys |
| CS | Cys188 | Ser |
| residues infuencing shape of active site | Leu191 | Del |

[1)]Del = deletion of amino acid residue

Non-limiting examples of mutants are those comprising at least on mutation in positions selected from 13, 14, 15, 189, 190 and 191; or multiple mutations comprising a combination of mutations obtained by any permutation of these positions, as for example 13 and 14,
13 and 15,
14 and 15,
13, 14 and 15,
14, 15 and 189,
14, 15 and 190,
14, 15, 189 and 190,
13, 14, 15 and 189,
13, 14, 15 and 190,
13, 14, 15, 189 and 190
13, 14 and 191,
13, 15 and 191;
14, 15 and 191,
13, 14, 15 and 191,
14, 15, 189 and 191
14, 15, 190 and 191,
14, 15, 189, 190 and 191,
13, 14, 15, 189 and 191,
13, 14, 15, 190 and 191,
13, 14, 15, 189, 190 and 191 etc.

Performing mutations in these positions allows improving the binding affinity of the enzyme to non-aromatic, non-cyclic malonates of formula (I), as for example those carrying an alkenyl substituent. Specific examples of amino acid mutations in this context are Val13Aly or Gly;
Pro14Val, Ala or Gly;
Pro15His, or Gly;
Gly189Ala or Del;
Gly190Ala, Ser or Del;
Leu191 Del.

The mutations Pro14Val and Pro15H is may provide for better binding of small unsaturated aliphatic substrates. Adding Gly190Ala to such a double mutant might provide even better results. After adding a fourth mutation such as Gly189Ala the enzyme might be capable of accepting only unsaturated aliphatic substrates and no more aromatic ones. Mutations of Val13 and Pro14 to smaller amino acids such as Gly/Ala and deletion of one of the residues Gly189 or 190 should make the enzyme to better accept branched substrates. The above explanation shall not be considered as limiting.

In analogy a skilled reader will be able to define suitable mutants for the structurally related enzymes, i.e. from a) a protein comprising amino acid residues 2 to 241 of SEQ ID NO: 4 and origi from *Mesorhizobium* sp. BNCI;
b) a protein comprising amino acid residues 2 to 240 of SEQ ID NO: 6 and originating from *Pyrcoccus horikoshii* OT3;
c) a protein comprising amino acid residues 2 to 267 of SEQ ID NO: 8 and originating from *Bordetella Bronchiseptica* RB50; and
d) a protein comprising amino acid residues 2 to 246 of SEQ ID NO: 10 and originating from *Aklaliphilus metalliredigenes* QYMF;

The present invention also relates to a nucleic acid encoding a protein having decarboxylase activity as defined herein.

The present invention also relates to an expression cassette, comprising a nucleic acid as defined above, operably linked with at least one regulatory nucleic acid sequence.

The present invention also relates to a recombinant expression vector comprising at least one expression cassette or nucleic acid as defined above.

The present invention also relates to a recombinant microorganism, carrying at least one expression vector as defined above.

The present invention also relates to a bioreactor comprising at least one protein having decarboxylase activity as defined herein or a recombinant microorganism as defined above, optionally in immobilized form.

The present invention also relates to a method of preparing an enzyme with decarboxylase activity as defined herein, which method comprises cultivating a recombinant microorganism as defined above and optionally isolating the said decarboxylase from the culture.

The present invention also relates to a crystalline form of a protein having decarboxylase activity as defined herein, in particular those forms, wherein the protein having arylmalonate decarboxylase activity is as defined above.

A preferable crystalline form is obtained from the *Bordetella bronchiseptica* protein of SEQ ID NO: 2 (Blast database entry BAA02419.1), the crystals of which belong to the $P2_1$ space group with a unit cell having the constants a=38.7, b=65.6, c=42.2 Å (Angström), and β=110.8°.

The present invention also relates to a method of preparing a crystalline form of a protein having decarboxylase activity as defined herein, which method comprises adding to a solution containing said protein (in a concentration of about 1 to 50 or 5 to 20 mg/ml) a crystallization agent having a pH in the range of 8.3 to 8.7, as for example 8.5, preferably buffered with Tris buffer, and a polyalkylene glycol, like polyethylene glycol, in particular PEG 4000 to 8000, like PEG 6000.

The present invention also relates to a screening method for candidate enzymes having decarboxylase activity as defined herein, which method comprises identifying a sequence motif (pattern) characteristic for an enzyme with decarboxylase activity as defined herein and screening known amino acid sequences, as for example amino acid sequence data bases, for sequences partially or fully matching with said sequence motif. Preferably said sequence motif is derived from a the crystalline structure of the crystalline form of a protein having decarboxylase activity as defined by SEQ ID NO: 2, 4, 6, 8, 9, 10 or 12.

The present invention also relates to a method of preparing a candidate enzymes having decarboxylase activity as defined herein, screened by a method of as defined above, which method comprised obtaining a coding nucleotide sequence of the candidate enzyme, expressing said sequence in a recombinant microorganism and isolating said expression product. Finally, the present invention also relates to the use of an expression product as prepared by said method in a decarboxylation reaction decarboxylating a compound of formula I as defined above.

2. Explanation of Particular Terms

"AMDase" (EC 4.1.1.76) refers to enzymes having aryl malonate dehydrogenase activity and catalyze the enantioselective mono-decarboxylation of alpha-arylmalonates, like alpha-aryl-alpha-methylmalonate to give optically pure arylpropionate. The enzyme does not require biotin or any other co-factors for activity. In addition, decarboxylation does not involve formation of a malonyl thioester-enzyme intermediate.

An "enzymes having aryl malonate dehydrogenase (AMDase) activity" catalyzes the mono-decarboxylation, i.e. replacement of one carboxyl group by hydrogen, of at least one substrate of the general formula I as defined herein, in particular a substrate of formula I carrying at least one aromatic substituent in alpha position of malonate.

As decarboxylase enzymes or mutants disclosed herein, also may either show an extended substrate specificity (if compared to a non-mutated reference enzyme as herein described), according to which not only cyclic or aryl group-containing malonates are decarboxylated, but also non-aromatic, non-cyclic malonates are decarboxylated, or may prefer as a substrate such non-cyclic, non-aromatic malonates, the term "MDase" or "enzyme having MDase activity" as used herein more generally refers to those decarboxylase enzyme with extended substrate specificity and/or to those decarboxylase enzymes with altered or modified substrate preference or substrate specificity. Said MDases catalyze the mono-decarboxylation, i.e. replacement of one carboxyl group by hydrogen, of at least one substrate of the general formula I as defined herein, in particular also or exclusively those substrates of formula I carrying no cyclic or no aromatic substituent in alpha position of malonate. The MDase enzyme does not require biotin or any other co-factors for activity. In addition, decarboxylation does not involve formation of a malonyl thioester-enzyme intermediate.

An "extended substrate specificity" refers to enzymes which, if compared to a reference enzyme, convert additional structurally different substrates.

An "altered/modified substrate specificity" refers to enzymes which, if compared to a reference enzyme, convert a partially or completely different set of substrate molecules. Thus, the term "altered substrate specificity" may describes a situation where a decarboxylase enzyme, for example effected by mutation, is better adapted for the decarboxylation of a specific substrate molecule than a reference enzyme (as for example the non-mutated enzyme). For example, a higher preference or specificity may be caused by a higher substrate affinity of the binding pocked formed by the enzyme variants.

An "altered/modified enzyme activity" refers to enzymes which, if compared to a reference enzyme, show for at least one common substrate molecule a faster or slower conversion kinetics.

The term "decarboxylase" or "enzyme having decarboxylase activity" as used herein, unless otherwise stated, generically refers to AMDase and/or MDase enzymes as defined herein.

Due to the reversibility of enzymatic reaction the present invention also relates to the corresponding reverse (i.e. monocarboxylation) reaction of the biocatalytic decarboxylation reactions described herein.

The term "biocatalytic method" refers to any method performed in the presence of catalytic activity of a decarboxylase enzyme (AMDase or MDase) as defined herein, i.e. in the presence of isolated pure or crude enzyme or entire microbial cells containing or expression such enzyme activity.

The term "stereospecific" means that one of several enantiomers is formed by the enzyme in high enantiomeric excess or purity, of at least 90% ee, preferably at least 95% ee, in particular at least 98% ee, or at least 99% ee. the ee % value is calculated according to the following formula $$ee\% = [X_A - X_B]/[X_A + X_B] * 100,$$

wherein $X_A$ and $X_B$ refer to the molar fraction of enantiomer A or B, respectively.

The "substrate pocket" of an AMDase, MDase or decarboxylase enzyme as defined herein, or its "reactivity centre" harbours during the reaction to be catalyzed a substrate molecule of formula I and converts it to a product of formula II. Said substrate pocket is composed of certain "structural elements" i.e. portions of said substrate pocket with different function. Said structural elements are in "functional arrangement" to each other, i.e. they cooperate during the reaction to be catalyzed.

A "sequence motif" or "pattern" represents a characteristic arrangement or "fingerprint" of a plurality of amino acid residues which are either adjacent to each other within a specific amino acid sequence or are separated from each other in a defined manner, i.e. by intermediate spacer sequences of characteristic length.

As regards substrates of formula I and products of formula II the following meanings are preferred:

A "salt form" refers to an ammonium salt or an alkali or alkaline earth metal salt, as for example $Na^+$, $K^+$ or $Ca^{2+}$ salts.

"Lower alkyl" refers to $C_1$-$C_8$-alkyl radicals which are linear or branched radicals having from 1 to 8, preferably 1, 2, 3 or 4 carbon atoms. Examples thereof are the $C_1$-$C_4$-alkyl radicals methyl, ethyl, n-propyl, isopropyl, n-butyl, 2-butyl, isobutyl or tert-butyl; and additionally residues with more than 4 carbon atoms like pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, heptyl, octyl and their constitutional isomers such as 2-ethylhexyl "Lower alkoxy" preferably refers to the $C_1$-$C_8$-alkoxy analogues of the above-mentioned lower alkyl radicals.

"Lower alkylthio" preferably refers to the $C_1$-$C_8$-alkthio analogues of the above-mentioned lower alkyl radicals. Examples are methylthio, ethylthio, propylthio, isopropylthio, butylthio, sec-butylthio, isobutylthio and tert-butylthio.

"Lower alkenyl" comprises $C_2$-$C_8$-alkenyl radicals which are monounsaturated linear or branched hydrocarbon radicals having from 2 to 8, preferably 2 to 4, carbon atoms, as for example ethenyl, 1- or 2-propenyl, 1-, 2- and 3-butenyl, 2-methylpropen-3-yl, 2-methylpropen-1-yl, 1-, 2-, 3- and 4-pentenyl, 1-, 2-, 3-, 4- and 5-hexenyl, 1-, 2-, 3-, 4-, 5- and 6-heptenyl 1-, 2-, 3-, 4-, 5-, 6- and 7-octenyl and also their constitutional isomers.

"Lower alkynyl" comprises the alkynyl homologues of the above "lower alkeny" radicals.

The term "hydroxy lower-alkyl" refers to $C_1$-$C_8$-hydroxyalkyl which is a linear or branched alkyl radical having from 1 to 8, in particular from 1 to 4 carbon atoms, in which at least one hydrogen atom, for example for 2 of the hydrogen atoms, is/are replaced by a hydroxyl group. Examples thereof are, hydroxymethyl, 2-hydroxy-1-ethyl, 2- and 3-hydroxy-1-propyl, 2-, 3- and 4-hydroxy-1-butyl, 2-, 3-, 4- and 5-hydroxy-1-pentyl, 2-, 3-, 4-, 5- and 6-hydroxy-1-hexyl, 2-, 3-, 4-, 5-, 6- and 7-hydroxy-1-heptyl, 2-, 3-, 4-, 5-, 6-, 7- and 8-hydroxy-1-octyl, 2,3-dihydroxy-1-propyl and their constitutional isomers.

The term "cyloalkylidene" represents ring structures comprising 4 to 7 ring carbon atoms, linked via a double bond to the residual structure of a molecule. As examples there may be mentioned cyclopentylidene, cyclohexylidene and cycloheptylidene.

As examples for "mono- or bicyclic ring" residues there may be mentioned carbo- or heterocyclic, optionally condensed, non-aromatic or preferably aromatic or heteroaromatic rings, having 3 to 12 ring carbon atoms and optionally 1 to 4 heteroatoms, like N, S and O. As examples there may be mentioned cyclopropyl, cyclobutyl, cyclopenty, cyclohexyl, cycloheptyl, as well as the mono- or polyunsaturated analogues thereof, as for example cyclobutenyl, cyclopentenyl, cyclohexenyl, cycloheptenyl, cyclohexadienyl, cycloheptadienyl, as well as naphthyl and phenyl; as well as 5- to 7-membered saturated on mono- or polyunsaturated heterocyclic radicals having 1 to 4 heteroatoms, selected from O, N and S, and wherein the heterocyclic ring may be further condensed with another heterocyclic or carbocyclic ring. Example of heterocyclic residues are those derived from pyrrolidine, tetrahydrofurane, piperidine, morpholine, pyrrole, furane, thiophene, pyrazole, imidazole, oxazole, thiazole, pyridine, pyrane, pyrimidine, pyridazine, pyrazine, coumarone, indole and quinoline. A "monocyclic" ring also comprises the above-mentioned cycloalkylidene structures.

As "optional substituents" there may be mentioned $NH_2$, OH, SH, halogen, like F, Cl, Br, J; lower alkoxy, lower alkylthio, lower alkyl, lower alkenyl, lower alkynyl or hydroxyl-lower alkyl, as defined above. "Optional substituents" also comprises the above-mentioned cycloalkylidene residues, which may be considered as being formed by two of such substituents.

3. Other Embodiments of the Invention

3.1 Proteins According to the Invention

The present invention is not limited to the specifically disclosed "proteins with AMDase activity", or "proteins with MDase activity" but also extends to functional equivalents thereof.

"Functional equivalents" or analogs of the concretely disclosed enzymes are, within the scope of the present invention, various polypeptides thereof, which moreover possess the desired biological function or activity, e.g. enzyme activity.

For example, "functional equivalents" means enzymes, which, in a test used for enzymatic activity, display at least a 1 to 10%, or at least 20%, or at least 50%, or at least 75%, or at least 90% higher or lower activity of an enzyme, as defined herein.

"Functional equivalents", according to the invention, also means in particular mutants, which, in at least one sequence position of the amino acid sequences stated above, have an amino acid that is different from that concretely stated, but nevertheless possess one of the aforementioned biological activities. "Functional equivalents" thus comprise the mutants obtainable by one or more amino acid additions, substitutions, insertions, deletions and/or inversions, where the stated changes can occur in any sequence position, provided they lead to a mutant with the profile of properties according to the invention. Functional equivalence is in particular also provided if the reactivity patterns coincide qualitatively between the mutant and the unchanged polypeptide, i.e. if for example the same substrates are converted at a different rate. Examples of suitable amino acid substitutions are shown in the following table:

| Original residue | Examples of substitution |
|---|---|
| Ala | Ser |
| Arg | Lys |
| Asn | Gln; His |
| Asp | Glu |
| Cys | Ser |
| Gln | Asn |
| Glu | Asp |
| Gly | Pro |
| His | Asn; Gln |
| Ile | Leu; Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

"Functional equivalents" in the above sense are also "precursors" of the polypeptides described, as well as "functional derivatives" and "salts" of the polypeptides.

"Precursors" are in that case natural or synthetic precursors of the polypeptides with or without the desired biological activity.

The expression "salts" means salts of carboxyl groups as well as salts of acid addition of amino groups of the protein molecules according to the invention. Salts of carboxyl groups can be produced in a known way and comprise inorganic salts, for example sodium, calcium, ammonium, iron and zinc salts, and salts with organic bases, for example amines, such as triethanolamine, arginine, lysine, piperidine and the like. Salts of acid addition, for example salts with inorganic acids, such as hydrochloric acid or sulfuric acid and salts with organic acids, such as acetic acid and oxalic acid, are also covered by the invention.

"Functional derivatives" of polypeptides according to the invention can also be produced on functional amino acid side groups or at their N-terminal or C-terminal end using known techniques. Such derivatives comprise for example aliphatic esters of carboxylic acid groups, amides of carboxylic acid groups, obtainable by reaction with ammonia or with a primary or secondary amine; N-acyl derivatives of free amino groups, produced by reaction with acyl groups; or O-acyl derivatives of free hydroxy groups, produced by reaction with acyl groups.

"Functional equivalents" naturally also comprise polypeptides that can be obtained from other organisms, as well as naturally occurring variants. For example, areas of homologous sequence regions can be established by sequence comparison, and equivalent enzymes can be determined on the basis of the concrete parameters of the invention.

"Functional equivalents" also comprise fragments, preferably individual domains or sequence motifs, of the polypeptides according to the invention, which for example display the desired biological function.

"Functional equivalents" are, moreover, fusion proteins, which have one of the polypeptide sequences stated above or functional equivalents derived there from and at least one further, functionally different, heterologous sequence in functional N-terminal or C-terminal association (i.e. without substantial mutual functional impairment of the fusion protein parts). Non-limiting examples of these heterologous sequences are e.g. signal peptides, histidine anchors or enzymes.

"Functional equivalents" that are also included according to the invention are homologues of the concretely disclosed proteins. These possess percent identity values as stated above. Said values refer to the identity with the concretely disclosed amino acid sequences, and may be calculated according to the algorithm of Pearson and Lipman, Proc. Natl. Acad, Sci. (USA) 85(8), 1988, 2444-2448.

The % identity values may also be calculated from BLAST alignments, algorithm blastp (protein-protein BLAST) or by applying the Clustal setting as given below.

A percentage identity of a homologous polypeptide according to the invention means in particular the percentage identity of the amino acid residues relative to the total length of one of the amino acid sequences concretely described herein.

In the case of a possible protein glycosylation, "functional equivalents" according to the invention comprise proteins of the type designated above in deglycosylated or glycosylated form as well as modified forms that can be obtained by altering the glycosylation pattern.

Such functional equivalents or homologues of the proteins or polypeptides according to the invention can be produced by mutagenesis, e.g. by point mutation, lengthening or shortening of the protein.

Such functional equivalents or homologues of the proteins according to the invention can be identified by screening combinatorial databases of mutants, for example shortening mutants. For example, a variegated database of protein variants can be produced by combinatorial mutagenesis at the nucleic acid level, e.g. by enzymatic ligation of a mixture of synthetic oligonucleotides. There are a great many methods that can be used for the production of databases of potential homologues from a degenerated oligonucleotide sequence. Chemical synthesis of a degenerated gene sequence can be carried out in an automatic DNA synthesizer, and the synthetic gene can then be ligated in a suitable expression vector. The use of a degenerated genome makes it possible to supply all sequences in a mixture, which code for the desired set of potential protein sequences. Methods of synthesis of degenerated oligonucleotides are known to a person skilled in the art (e.g. Narang, S. A. (1983) Tetrahedron 39:3; Itakura et al. (1984) Annu. Rev. Biochem. 53:323; Itakura et al., (1984) Science 198:1056; Ike et al. (1983) Nucleic Acids Res. 11:477).

In the prior art, several techniques are known for the screening of gene products of combinatorial databases, which were produced by point mutations or shortening, and for the screening of cDNA libraries for gene products with a selected property. These techniques can be adapted for the rapid screening of the gene banks that were produced by combinatorial mutagenesis of homologues according to the invention. The techniques most frequently used for the screening of large gene banks, which are based on a high-throughput analysis, comprise cloning of the gene bank in expression vectors that can be replicated, transformation of the suitable cells with the resultant vector database and expression of the combinatorial genes in conditions in which detection of the desired activity facilitates isolation of the vector that codes for the gene whose product was detected. Recursive Ensemble Mutagenesis (REM), a technique that increases the frequency of functional mutants in the databases, can be used in combination with the screening tests, in order to identify homologues (Arkin and Yourvan (1992) PNAS 89:7811-7815; Delgrave et al. (1993) Protein Engineering 6(3):327-331).

3.2 Coding Nucleic Acid Sequences

The invention also relates to nucleic acid sequences that code for enzymes as defined herein.

The present invention also relates to nucleic acids with a certain degree of "identity" to the sequences specifically disclosed herein. "Identity" between two nucleic acids means identity of the nucleotides, in each case over the entire length of the nucleic acid.

For example the identity may be calculated by means of the Vector NTI Suite 7.1 program of the company Informax (USA) employing the Clustal Method (Higgins D G, Sharp P M. Fast and sensitive multiple sequence alignments on a microcomputer. Comput Appl. Biosci. 1989 April; 5(2):151-1) with the following settings:

Multiple Alignment Parameter:

| | |
|---|---|
| Gap opening penalty | 10 |
| Gap extension penalty | 10 |
| Gap separation penalty range | 8 |
| Gap separation penalty | off |
| % identity for alignment delay | 40 |
| Residue specific gaps | off |
| Hydrophilic residue gap | off |
| Transition weighing | 0 |

Pairwise Alignment Parameter:

| | |
|---|---|
| FAST algorithm | on |
| K-tuple size | 1 |
| Gap penalty | 3 |
| Window size | 5 |
| Number of best diagonals | 5 |

Alternatively the identity may be determined according to Chema, Ramu, Sugawara, Hideaki, Koike, Tadashi, Lopez, Rodrigo, Gibson, Toby J, Higgins, Desmond G, Thompson, Julie D. Multiple sequence alignment with the Clustal series of programs. (2003) Nucleic Acids Res 31 (13):3497-500, the web page: ebi.ac.uk/Tools/clustalw/index.html# and the following settings

| | |
|---|---|
| DNA Gap Open Penalty | 15.0 |
| DNA Gap Extension Penalty | 6.66 |
| DNA Matrix | Identity |
| Protein Gap Open Penalty | 10.0 |
| Protein Gap Extension Penalty | 0.2 |
| Protein matrix | Gonnet |
| Protein/DNA ENDGAP | −1 |
| Protein/DNA GAPDIST | 4 |

All the nucleic acid sequences mentioned herein (single-stranded and double-stranded DNA and RNA sequences, for example cDNA and mRNA) can be produced in a known way by chemical synthesis from the nucleotide building blocks, e.g. by fragment condensation of individual overlapping, complementary nucleic acid building blocks of the double helix. Chemical synthesis of oligonucleotides can, for example, be performed in a known way, by the phosphoamidite method (Voet, Voet, 2nd edition, Wiley Press, New York, pages 896-897). The accumulation of synthetic oligonucleotides and filling of gaps by means of the Klenow fragment of DNA polymerase and ligation reactions as well as general cloning techniques are described in Sambrook et al. (1989), see below.

The invention also relates to nucleic acid sequences (single-stranded and double-stranded DNA and RNA sequences, e.g. cDNA and mRNA), coding for one of the above polypeptides and their functional equivalents, which can be obtained for example using artificial nucleotide analogs.

The invention relates both to isolated nucleic acid molecules, which code for polypeptides or proteins according to the invention or biologically active segments thereof, and to nucleic acid fragments, which can be used for example as hybridization probes or primers for identifying or amplifying coding nucleic acids according to the invention.

The nucleic acid molecules according to the invention can in addition contain non-translated sequences from the 3' and/or 5' end of the coding genetic region.

The invention further relates to the nucleic acid molecules that are complementary to the concretely described nucleotide sequences or a segment thereof.

The nucleotide sequences according to the invention make possible the production of probes and primers that can be used for the identification and/or cloning of homologous sequences in other cellular types and organisms. Such probes or primers generally comprise a nucleotide sequence region which hybridizes under "stringent" conditions (see below) on at least about 12, preferably at least about 25, for example about 40, 50 or 75 successive nucleotides of a sense strand of a nucleic acid sequence according to the invention or of a corresponding antisense strand.

An "isolated" nucleic acid molecule is separated from other nucleic acid molecules that are present in the natural source of the nucleic acid and can moreover be substantially free from other cellular material or culture medium, if it is being produced by recombinant techniques, or can be free from chemical precursors or other chemicals, if it is being synthesized chemically.

A nucleic acid molecule according to the invention can be isolated by means of standard techniques of molecular biology and the sequence information supplied according to the invention. For example, cDNA can be isolated from a suitable cDNA library, using one of the concretely disclosed complete sequences or a segment thereof as hybridization probe and standard hybridization techniques (as described for example in Sambrook, J., Fritsch, E. F. and Maniatis, T. Molecular Cloning: A Laboratory Manual. 2nd edition, Cold Spring Harbor Laboratory, Cold Spring Harbor Laboratory Press, Cold Spring Harbor, N.Y., 1989). In addition, a nucleic acid molecule comprising one of the disclosed sequences or a segment thereof, can be isolated by the polymerase chain reaction, using the oligonucleotide primers that were constructed on the basis of this sequence. The nucleic acid amplified in this way can be cloned in a suitable vector and can be characterized by DNA sequencing. The oligonucleotides according to the invention can also be produced by standard methods of synthesis, e.g. using an automatic DNA synthesizer.

Nucleic acid sequences according to the invention or derivatives thereof, homologues or parts of these sequences, can for example be isolated by usual hybridization techniques or the PCR technique from other bacteria, e.g. via genomic or cDNA libraries. These DNA sequences hybridize in standard conditions with the sequences according to the invention.

"Hybridize" means the ability of a polynucleotide or oligonucleotide to bind to an almost complementary sequence in standard conditions, whereas nonspecific binding does not occur between non-complementary partners in these conditions. For this, the sequences can be 90-100% complementary. The property of complementary sequences of being able to bind specifically to one another is utilized for example in Northern Blotting or Southern Blotting or in primer binding in PCR or RT-PCR.

Short oligonucleotides of the conserved regions are used advantageously for hybridization. However, it is also possible to use longer fragments of the nucleic acids according to the invention or the complete sequences for the hybridization. These standard conditions vary depending on the nucleic acid used (oligonucleotide, longer fragment or complete sequence) or depending on which type of nucleic acid—DNA or RNA—is used for hybridization. For example, the melting temperatures for DNA:DNA hybrids are approx. 10° C. lower than those of DNA:RNA hybrids of the same length.

For example, depending on the particular nucleic acid, standard conditions mean temperatures between 42 and 58° C. in an aqueous buffer solution with a concentration between 0.1 to 5×SSC (1×SSC=0.15 M NaCl, 15 mM sodium citrate, pH 7.2) or additionally in the presence of 50% formamide, for example 42° C. in 5×SSC, 50% formamide. Advantageously, the hybridization conditions for DNA:DNA hybrids are 0.1× SSC and temperatures between about 20° C. to 45° C., preferably between about 30° C. to 45° C. For DNA:RNA hybrids the hybridization conditions are advantageously 0.1×SSC and temperatures between about 30° C. to 55° C., preferably between about 45° C. to 55° C. These stated temperatures for hybridization are examples of calculated melting temperature values for a nucleic acid with a length of approx. 100 nucleotides and a G+C content of 50% in the absence of formamide. The experimental conditions for DNA hybridization are described in relevant genetics textbooks, for example Sambrook et al., 1989, and can be calculated using formulae that are known by a person skilled in the art, for example depending on the length of the nucleic acids, the type of hybrids or the G+C content. A person skilled in the art can obtain further information on hybridization from the following textbooks: Ausubel et al. (eds), 1985, Current Protocols in Molecular Biology, John Wiley & Sons, New York; Hames and Higgins (eds), 1985, Nucleic Acids Hybridization: A Practical Approach, IRL Press at Oxford University Press, Oxford; Brown (ed), 1991, Essential Molecular Biology: A Practical Approach, IRL Press at Oxford University Press, Oxford.

"Hybridization" can in particular be carried out under stringent conditions. Such hybridization conditions are for example described in Sambrook, J., Fritsch, E. F., Maniatis, T., in: Molecular Cloning (A Laboratory Manual), 2nd edition, Cold Spring Harbor Laboratory Press, 1989, pages 9.31-9.57 or in Current Protocols in Molecular Biology, John Wiley & Sons, N.Y. (1989), 6.3.1-6.3.6.

"Stringent" hybridization conditions mean in particular: Incubation at 42° C. overnight in a solution consisting of 50% formamide, 5×SSC (750 mM NaCl, 75 mM trisodium citrate), 50 mM sodium phosphate (pH 7.6), 5×Denhardt Solution, 10% dextran sulfate and 20 g/ml denatured, sheared salmon sperm DNA, followed by washing of the filters with 0.1×SSC at 65° C.

The invention also relates to derivatives of the concretely disclosed or derivable nucleic acid sequences.

Thus, further nucleic acid sequences according to the invention can be derived from the sequences specifically disclosed herein and can differ from it by addition, substitution, insertion or deletion of individual or several nucleotides, and furthermore code for polypeptides with the desired profile of properties.

The invention also encompasses nucleic acid sequences that comprise so-called silent mutations or have been altered, in comparison with a concretely stated sequence, according to the codon usage of a special original or host organism, as well as naturally occurring variants, e.g. splicing variants or allelic variants, thereof.

It also relates to sequences that can be obtained by conservative nucleotide substitutions (i.e. the amino acid in question is replaced by an amino acid of the same charge, size, polarity and/or solubility).

The invention also relates to the molecules derived from the concretely disclosed nucleic acids by sequence polymorphisms. These genetic polymorphisms can exist between individuals within a population owing to natural variation. These natural variations usually produce a variance of 1 to 5% in the nucleotide sequence of a gene.

Derivatives of nucleic acid sequences according to the invention mean for example allelic variants, having at least 60% homology at the level of the derived amino acid, preferably at least 80% homology, quite especially preferably at least 90% homology over the entire sequence range (regarding homology at the amino acid level, reference should be made to the details given above for the polypeptides). Advantageously, the homologies can be higher over partial regions of the sequences.

Furthermore, derivatives are also to be understood to be homologues of the nucleic acid sequences according to the invention, for example animal, plant, fungal or bacterial homologues, shortened sequences, single-stranded DNA or RNA of the coding and noncoding DNA sequence. For example, homologues have, at the DNA level, a homology of at least 40%, preferably of at least 60%, especially preferably of at least 70%, quite especially preferably of at least 80% over the entire DNA region given in a sequence specifically disclosed herein.

Moreover, derivatives are to be understood to be, for example, fusions with promoters. The promoters that are added to the stated nucleotide sequences can be modified by at least one nucleotide exchange, at least one insertion, inversion and/or deletion, though without impairing the functionality or efficacy of the promoters. Moreover, the efficacy of the promoters can be increased by altering their sequence or can be exchanged completely with more effective promoters even of organisms of a different genus.

3.3 Constructs According to the Invention

The invention also relates to expression constructs, containing, under the genetic control of regulatory nucleic acid sequences, a nucleic acid sequence coding for a polypeptide or fusion protein according to the invention; as well as vectors comprising at least one of these expression constructs.

"Expression unit" means, according to the invention, a nucleic acid with expression activity, which comprises a promoter as defined herein and, after functional association with a nucleic acid that is to be expressed or a gene, regulates the expression, i.e. the transcription and the translation of this nucleic acid or of this gene. In this context, therefore, it is also called a "regulatory nucleic acid sequence". In addition to the promoter, other regulatory elements may be present, e.g. enhancers.

"Expression cassette" or "expression construct" means, according to the invention, an expression unit, which is functionally associated with the nucleic acid that is to be expressed or the gene that is to be expressed. In contrast to an expression unit, an expression cassette thus comprises not only nucleic acid sequences which regulate transcription and translation, but also the nucleic acid sequences which should be expressed as protein as a result of the transcription and translation.

The terms "expression" or "overexpression" describe, in the context of the invention, the production or increase of intracellular activity of one or more enzymes in a microorganism, which are encoded by the corresponding DNA. For this, it is possible for example to insert a gene in an organism, replace an existing gene by another gene, increase the number of copies of the gene or genes, use a strong promoter or use a gene that codes for a corresponding enzyme with a high activity, and optionally these measures can be combined.

Preferably such constructs according to the invention comprise a promoter 5'-upstream from the respective coding sequence, and a terminator sequence 3'-downstream, and optionally further usual regulatory elements, in each case functionally associated with the coding sequence.

A "promoter", a "nucleic acid with promoter activity" or a "promoter sequence" mean, according to the invention, a nucleic acid which, functionally associated with a nucleic acid that is to be transcribed, regulates the transcription of this nucleic acid.

"Functional" or "operative" association means, in this context, for example the sequential arrangement of one of the nucleic acids with promoter activity and of a nucleic acid sequence that is to be transcribed and optionally further regulatory elements, for example nucleic acid sequences that enable the transcription of nucleic acids, and for example a terminator, in such a way that each of the regulatory elements can fulfill its function in the transcription of the nucleic acid sequence. This does not necessarily require a direct association in the chemical sense. Genetic control sequences, such as enhancer sequences, can also exert their function on the target sequence from more remote positions or even from other DNA molecules. Arrangements are preferred in which the nucleic acid sequence that is to be transcribed is positioned behind (i.e. at the 3' end) the promoter sequence, so that the two sequences are bound covalently to one another. The distance between the promoter sequence and the nucleic acid sequence that is to be expressed transgenically can be less than 200 bp (base pairs), or less than 100 bp or less than 50 bp.

Apart from promoters and terminators, examples of other regulatory elements that may be mentioned are targeting sequences, enhancers, polyadenylation signals, selectable markers, amplification signals, replication origins and the like. Suitable regulatory sequences are described for example in Goeddel, Gene Expression Technology: Methods in Enzymology 185, Academic Press, San Diego, Calif. (1990).

Nucleic acid constructs according to the invention comprise in particular sequences selected from those, specifically mentioned herein or derivatives and homologues thereof, as well as the nucleic acid sequences that can be derived from amino acid sequences specifically mentioned herein which are advantageously associated operatively or functionally with one or more regulating signal for controlling, e.g. increasing, gene expression.

In addition to these regulatory sequences, the natural regulation of these sequences can still be present in front of the actual structural genes and optionally can have been altered genetically, so that natural regulation is switched off and the expression of the genes has been increased. The nucleic acid construct can also be of a simpler design, i.e. without any additional regulatory signals being inserted in front of the coding sequence and without removing the natural promoter with its regulation. Instead, the natural regulatory sequence is silenced so that regulation no longer takes place and gene expression is increased.

A preferred nucleic acid construct advantageously also contains one or more of the aforementioned enhancer sequences, functionally associated with the promoter, which permit increased expression of the nucleic acid sequence. Additional advantageous sequences, such as other regulatory elements or terminators, can also be inserted at the 3' end of the DNA sequences. One or more copies of the nucleic acids according to the invention can be contained in the construct. The construct can also contain other markers, such as antibiotic resistances or auxotrophy-complementing genes, optionally for selection on the construct.

Examples of suitable regulatory sequences are contained in promoters such as cos-, tac-, trp-, tet-, trp-tet-, lpp-, lac-, lpp-lac-, lacI$^{q-}$, T7-, T5-, T3-, gal-, trc-, ara-, rhaP (rhaP$_{BAD}$) SP6-, lambda-P$_R$- or in the lambda-P$_L$ promoter, which find application advantageously in Gram-negative bacteria. Other advantageous regulatory sequences are contained for example in the Gram-positive promoters ace, amy and SPO2, in the yeast or fungal promoters ADC1, MFalpha, AC, P-60, CYC1, GAPDH, TEF, rp28, ADH. Artificial promoters can also be used for regulation.

For expression, the nucleic acid construct is inserted in a host organism advantageously in a vector, for example a plasmid or a phage, which permits optimum expression of the genes in the host. In addition to plasmids and phages, vectors are also to be understood as meaning all other vectors known to a person skilled in the art, e.g. viruses, such as SV40, CMV, baculovirus and adenovirus, transposons, IS elements, phasmids, cosmids, and linear or circular DNA. These vectors can be replicated autonomously in the host organism or can be replicated chromosomally. These vectors represent a further embodiment of the invention.

Suitable plasmids are, for example in *E. coli*, pLG338, pACYC184, pBR322, pUC18, pUC19, pKC30, pRep4, pHS1, pKK223-3, pDHE19.2, pHS2, pPLc236, pMBL24, pLG200, pUR290, pIN-III[113]-B1, λgt11 or pBdCl; in nocardioform actinomycetes pJAM2; in *Streptomyces* pIJ101, pIJ364, pIJ702 or pIJ361; in *bacillus* pUB110, pC194 or pBD214; in *Corynebacterium* pSA77 or pAJ667; in fungi pALS1, pIL2 or pBB116; in yeasts 2alphaM, pAG-1, YEp6, YEp13 or pEMBLYe23 or in plants pLGV23, pGHlac$^+$, pBIN19, pAK2004 or pDH51. The aforementioned plasmids represent a small selection of the possible plasmids. Other plasmids are well known to a person skilled in the art and will be found for example in the book Cloning Vectors (Eds. Pouwels P. H. et al. Elsevier, Amsterdam-New York-Oxford, 1985, ISBN 0 444 904018).

In a further embodiment of the vector, the vector containing the nucleic acid construct according to the invention or the nucleic acid according to the invention can be inserted advantageously in the form of a linear DNA in the microorganisms and integrated into the genome of the host organism through heterologous or homologous recombination. This linear DNA can comprise a linearized vector such as plasmid or just the nucleic acid construct or the nucleic acid according to the invention.

For optimum expression of heterologous genes in organisms, it is advantageous to alter the nucleic acid sequences in accordance with the specific codon usage employed in the organism. The codon usage can easily be determined on the basis of computer evaluations of other, known genes of the organism in question.

The production of an expression cassette according to the invention is based on fusion of a suitable promoter with a suitable coding nucleotide sequence and a terminator signal or polyadenylation signal. Common recombination and cloning techniques are used for this, as described for example in T. Maniatis, E. F. Fritsch and J. Sambrook, Molecular Cloning: A Laboratory Manual, Cold Spring Harbor Laboratory, Cold Spring Harbor, N.Y. (1989) as well as in T. J. Silhavy, M. L. Berman and L. W. Enquist, Experiments with Gene Fusions, Cold Spring Harbor Laboratory, Cold Spring Harbor, N.Y. (1984) and in Ausubel, F. M. et al., Current Protocols in Molecular Biology, Greene Publishing Assoc. and Wiley Interscience (1987).

The recombinant nucleic acid construct or gene construct is inserted advantageously in a host-specific vector for expression in a suitable host organism, to permit optimum expression of the genes in the host. Vectors are well known to a person skilled in the art and will be found for example in "Cloning Vectors" (Pouwels P. H. et al., Publ. Elsevier, Amsterdam-New York-Oxford, 1985).

3.4 Hosts that can be Used According to the Invention

Depending on the context, the term "microorganism" means the starting microorganism (wild-type) or a genetically modified microorganism according to the invention, or both.

The term "wild-type" means, according to the invention, the corresponding starting microorganism, and need not necessarily correspond to a naturally occurring organism.

By means of the vectors according to the invention, recombinant microorganisms can be produced, which have been transformed for example with at least one vector according to the invention and can be used for production of the polypeptides according to the invention. Advantageously, the recombinant constructs according to the invention, described above, are inserted in a suitable host system and expressed. Preferably, common cloning and transfection methods that are familiar to a person skilled in the art are used, for example co-precipitation, protoplast fusion, electroporation, retroviral transfection and the like, in order to secure expression of the stated nucleic acids in the respective expression system. Suitable systems are described for ex-, ample in Current Protocols in Molecular Biology, F. Ausubel et al., Publ. Wiley Interscience, New York 1997, or Sambrook et al. Molecular Cloning: A Laboratory Manual. 2nd edition, Cold Spring Harbor Laboratory, Cold Spring Harbor Laboratory Press, Cold Spring Harbor, N.Y., 1989.

In principle, all prokaryotic organisms can be considered as recombinant host organisms for the nucleic acid according to the invention or the nucleic acid construct. Bacteria are used advantageously as host organisms. Preferably they are selected from native or recombinant bacteria having the ability to produce inclusion bodies of the PHA-, TAG- or WE-type, as in particular the TAG-producing nocardioform actinomycetes, in particular of the genus *Rhodococcus, Mycobacterium, Nocardia, Gordonia, Skermania* and *Tsukamurella*; as well as TAG-producing Streptomycetes; WE-producing genera *Acinetobacter* and *Alcanivorax*; as well as recombinant strains of the genus *Escherichia*, especially *E. coli, Corynebacterium*, especially *C. glutamicum* and *Bacillus*, especially *B. subtilis*.

The host organism or host organisms according to the invention then preferably contain at least one of the nucleic acid sequences, nucleic acid constructs or vectors described in this invention, which code for an enzyme activity according to the above definition.

The organisms used in the method according to the invention are grown or bred in a manner familiar to a person skilled in the art, depending on the host organism. As a rule, microorganisms are grown in a liquid medium, which contains a source of carbon, generally in the form of sugars, a source of nitrogen generally in the form of organic sources of nitrogen such as yeast extract or salts such as ammonium sulfate, trace elements such as iron, manganese and magnesium salts and optionally vitamins, at temperatures between 0° C. and 100° C., preferably between 10° C. to 60° C. with oxygen aeration. The pH of the liquid nutrient medium can be maintained at a fixed value, i.e. regulated or not regulated during growing. Growing can be carried out batchwise, semi-batchwise or continuously. Nutrients can be supplied at the start of fermentation or can be supplied subsequently, either semi-continuously or continuously.

3.5 Recombinant Production Proteins with Decarboxylase Activity

The invention also relates to methods for production of proteins according to the invention by cultivating a microorganism which expresses said protein, and isolating the desired product from the culture.

The microorganisms as used according to the invention can be cultivated continuously or discontinuously in the batch process or in the fed batch or repeated fed batch process. A review of known methods of cultivation will be found in the textbook by Chmiel (Bioprocesstechnik 1. Einführung in die Bioverfahrenstechnik (Gustav Fischer Verlag, Stuttgart, 1991)) or in the textbook by Storhas (Bioreaktoren and periphere Einrichtungen (Vieweg Verlag, Braunschweig/Wiesbaden, 1994)).

The culture medium that is to be used must satisfy the requirements of the particular strains in an appropriate manner. Descriptions of culture media for various microorganisms are given in the handbook "Manual of Methods for General Bacteriology" of the American Society for Bacteriology (Washington D.C., USA, 1981).

These media that can be used according to the invention generally comprise one or more sources of carbon, sources of nitrogen, inorganic salts, vitamins and/or trace elements.

Preferred sources of carbon are sugars, such as mono-, di- or polysaccharides. Very good sources of carbon are for example glucose, fructose, mannose, galactose, ribose, sorbose, ribulose, lactose, maltose, sucrose, raffinose, starch or cellulose. Sugars can also be added to the media via complex compounds, such as molasses, or other by-products from sugar refining. It may also be advantageous to add mixtures of various sources of carbon. Other possible sources of carbon are oils and fats such as soybean oil, sunflower oil, peanut oil and coconut oil, fatty acids such as palmitic acid, stearic acid or linoleic acid, alcohols such as glycerol, methanol or ethanol and organic acids such as acetic acid or lactic acid.

Sources of nitrogen are usually organic or inorganic nitrogen compounds or materials containing these compounds. Examples of sources of nitrogen include ammonia gas or ammonium salts, such as ammonium sulfate, ammonium chloride, ammonium phosphate, ammonium carbonate or ammonium nitrate, nitrates, urea, amino acids or complex sources of nitrogen, such as corn-steep liquor, soybean flour, soybean protein, yeast extract, meat extract and others. The sources of nitrogen can be used separately or as a mixture.

Inorganic salt compounds that may be present in the media comprise the chloride, phosphate or sulfate salts of calcium, magnesium, sodium, cobalt, molybdenum, potassium, manganese, zinc, copper and iron.

Inorganic sulfur-containing compounds, for example sulfates, sulfites, dithionites, tetrathionates, thiosulfates, sulfides, but also organic sulfur compounds, such as mercaptans and thiols, can be used as sources of sulfur.

Phosphoric acid, potassium dihydrogenphosphate or dipotassium hydrogenphosphate or the corresponding sodium-containing salts can be used as sources of phosphorus.

Chelating agents can be added to the medium, in order to keep the metal ions in solution. Especially suitable chelating agents comprise dihydroxyphenols, such as catechol or protocatechuate, or organic acids, such as citric acid.

The fermentation media used according to the invention may also contain other growth factors, such as vitamins or growth promoters, which include for example biotin, riboflavin, thiamine, folic acid, nicotinic acid, pantothenate and pyridoxine. Growth factors and salts often come from complex components of the media, such as yeast extract, molasses, corn-steep liquor and the like. In addition, suitable precursors can be added to the culture medium. The precise composition of the compounds in the medium is strongly dependent on the particular experiment and must be decided individually for each specific case. Information on media optimization can be found in the textbook "Applied Microbiol. Physiology, A Practical Approach" (Publ. P. M. Rhodes, P. F. Stanbury, IRL Press (1997) p. 53-73, ISBN 0 19 963577 3). Growing media can also be obtained from commercial suppliers, such as Standard 1 (Merck) or BHI (Brain heart infusion, DIFCO) etc.

All components of the medium are sterilized, either by heating (20 min at 1.5 bar and 121° C.) or by sterile filtration. The components can be sterilized either together, or if necessary separately. All the components of the medium can be present at the start of growing, or optionally can be added continuously or by batch feed.

The temperature of the culture is normally between 15° C. and 45° C., preferably 25° C. to 40° C. and can be kept constant or can be varied during the experiment. The pH value of the medium should be in the range from 5 to 8.5, preferably around 7.0. The pH value for growing can be controlled during growing by adding basic compounds such as sodium hydroxide, potassium hydroxide, ammonia or ammonia water or acid compounds such as phosphoric acid or sulfuric acid. Antifoaming agents, e.g. fatty acid polyglycol esters, can be used for controlling foaming. To maintain the stability of plasmids, suitable substances with selective action, e.g. antibiotics, can be added to the medium. Oxygen or oxygen-containing gas mixtures, e.g. the ambient air, are fed into the culture in order to maintain aerobic conditions. The temperature of the culture is normally from 20° C. to 45° C. Culture is continued until a maximum of the desired product has formed. This is normally achieved within 10 hours to 160 hours.

The cells can be disrupted optionally by high-frequency ultrasound, by high pressure, e.g. in a French pressure cell, by osmolysis, by the action of detergents, lytic enzymes or organic solvents, by means of homogenizers or by a combination of several of the methods listed.

The following examples only serve to illustrate the invention. The numerous possible variations that are obvious to a person skilled in the art also fall within the scope of the invention.

EXPERIMENTAL PART

1. General Information a) Instruments and Material

All chemicals (if not indicated otherwise) were purchased from Sigma-Aldrich. XhoI and NdeI restriction enzymes were purchased from Roche and T4 ligase from New England Biolabs. $^1$H NMR analysis was performed on Bruker 200 or 400 MHz spectrometers. ESI-MS analysis was carried out on a Bruker Esquire 3000$^+$ ion trap MS, equipped with an electrospray ionisation source run in positive mode. Samples of protein for ESI-MS analysis were desalted by dialysis for 4 h in ddH$_2$O.

b) Sequence Similarity Searches and Identification of New AMDases.

In order to find new malonate decarboxylases the protein sequence of AMDase from *Bordetella bronchiseptica* was aligned with sequences of known proteins from public databases, using the Basic Local Alignment Search Tool (BLAST). During the searches the following parameters were used: database—non-redundant protein sequences, algorithm—blastp (protein-protein BLAST).

From the list of hits of the most similar proteins to AMDase from *B. bronchiseptica* the following bacterial enzymes were selected:
protein EAN08019.1 from *Mesorhizobium* sp. BNC1,
protein BAA30082.1 from *Pyrococcus horikoshii* OT3,
protein NP_888076.1 from *Bordetella bronchiseptica* RB50 and
protein ZP_00801202.1 from *Alkaliphilus metalliredigenes* QYMF.

c) Sub-Cloning of AMDases and Other Enzymes

Genes coding for the following enzymes:
AMDase from *Bordetella bronchiseptica*,
protein EAN08019.1 from *Mesorhizobium* sp. BNC1,
protein BAA30082.1 from *Pyrococcus horikoshii* OT3,
protein NP_888076.1 from *Bordetella bronchiseptica* RB50 and
protein ZP_00801202.1 from *Alkaliphilus metalliredigenes* QYMF and
the glutamate racemase (AAF25672) from *Aquifex pyrophilus*
were optimized for expression in *E. coli*, synthesised and cloned into the pGA4 vector, containing the ampicillin resistance gene (GENEART AG., Germany). The genes were then sub-cloned into pET30b vector (Novagen, Cat. No. 69910-3, EMD Chemicals, Inc., San Diego, USA); containing the kanamycin resistance gene, using XhoI and NdeI restriction sites. The ligation product was transformed into BL21(DE3) electrocompetent *E. coli* cells, which were plated out on Kan50-LB-Agar plates. Plasmids were then isolated from the cells and successful sub-cloning was confirmed by sequencing. This sub-cloning allowed easy expression and purification (proteins were 6×His-Tagged) of targeted enzymes in *E. coli*. After sub-cloning into pET30b vector, the sequence of all enzymes at the C-terminus was extended by the following amino acids: Leu-Glu-His-His-His-His-His-His.

Nucleotide sequences according to SEQ ID NO: 1, 3, 5, 7, 9, and 11 represent those optimized sequences coding for his-tagged enzymes.

d) Expression and Purification of His$_6$-Fusion Proteins

Plasmids encoding AMDases, containing a T7 RNA polymerase promoter and a kanamycin resistance gene were transformed into electrocompetent *E. coli* strain BL21 (DE3). Bacteria were initially incubated in growing medium (1% tryptone, 0.5% yeast extract, 1% sodium chloride, 0.4% glucose, 0.20×M9 buffer (for 1 liter: KH$_2$PO$_4$ 3 g, Na$_2$HPO$_4$ 6 g, NaCl 5 g, MgSO$_4$ (1M) 1 ml, dH2O up to 1 liter), 50 mg/mL kanamycin) for approximately 4 h at a temperature of 37° C. to achieve OD$_{600}$=1. Addition of isopropyl-β-D-thiogalactopyranoside (1 mM, final concentration) induced protein expression. After overnight incubation at 30° C. the cells were pelleted (4500 rpm for 15 minutes, 4° C.) and lysed at room temperature after the addition of hen egg white lysozyme (0.1 mg/1 mL of buffer) in 50 mM TRIS buffer (pH 8) containing 25 mM NaCl, 2 mM EDTA, 0.2 mM DTT and the protease inhibitor—phenylmethanesulfonyl fluoride (10 μg/mL). After lysis, nucleic acids were precipitated by the addition of 2% streptomycin-sulfate followed by centrifugation (4500 rpm for 20 minutes, 4° C.). The supernatant, containing crude AMDase, was dialyzed (Spectra/Por 2, MWCO: 12-14 000) overnight against 25 mM TRIS buffer (pH 8) containing 25 mM NaCl, resulting in His$_6$ fusion proteins that were easily purified by FPLC on a GE Healthcare Bio-Science HiTrap Chelating 5 mL column. Elution of proteins was achieved by the use of a step gradient of sodium phosphate buffer (0.02 M, pH 7.4), NaCl (0.5 M) and imidazol (25, 60 & 250 mM). The target protein was eluted at 250 mM concentration of imidazol. This procedure yielded up to 15 mg of protein per 250 mL of culture and was typically 95% pure by SDS-PAGE. The final protein concentration was calculated by using either Bradford assay or spectrophotometrical reading at OD$_{280}$.

e) Site-Directed Mutagenesis of AMDase from *Bordetella bronchiseptica*

Site-directed mutagenesis was carried out using the Pfu Turbo polymerase (Stratagene) following the manufacturer instructions for the Stratagene QuikChange® Site-directed mutagenesis kit. PCR machine conditions were as follows: 1 segment cycle: 95° C. for 2 min; 2 segment cycle (repeated 30 times): 95° C. for 30 s, 55° C. for 30 s, and 72° C. for 5.5 min; 3 segment cycle: 4° C. for 10 min. After PCR, Dpn I restriction enzyme was added to digest the non-mutated plasmid. Mutated DNA was transferred into *E. coli* BL21 (DE3) and proteins were expressed following the procedure presented above for the wild type. Mutagenesis of other decarboxylase enzymes of the invention can be performed in analogy.

f) In Vivo Plate Assay to Determine AMDase Activity.

Test Petri dishes were prepared using following medium: 1% tryptone, 0.5% yeast extract, 1% sodium chloride, 1% agar, 0.025% bromothymol blue (BTB). Then pH was adjusted to 6.5 and the medium autoclaved. When medium temperature reached 50-60° C. isopropyl-β-D-thiogalactopyranoside (1 mM, final concentration), kanamycin (40 mg/mL, final concentration) and phenylmalonic acid (0.36%, final concentration) were added. 100 μl of liquid bacterial culture containing AMDase was plated on test Petri dishes. After 2-3 days of incubation at 37° C. the colonies and surrounding area changed colour to green-blue indicating AMDase activity.

g) Determination of Kinetic Constants

This method involves measuring spectrophotometrically at 620 nm the change of yellow colour to green/blue of pH indicator—BTB with increasing concentration of [OH$^-$] formed during the decarboxylation reaction. To ensure that the increase of colour is linear with the increase of pH the measurement should be done around the pKa of the pH indicator (pKa of BTB=7.3).[17] We found that 5 mM (and/or 10 mM) MOPS buffer pH 7.2 was suitable. More concentrated buffer (10 mM) gives better results with higher concentration of enzyme or quicker reactions since changes of colour are slower due to higher buffer capacity.

All kinetics assays were performed on an Anthos Zenyth 3100 96-well microplate reader. 10 μl of 20-500 mM phenylmalonate or methyl-phenylmalonate solution (pH adjusted to 7.2) was added to 180 μl of 5-10 mM MOPS buffer pH 7.2 containing 0.0186 mM bromothymol blue. The reaction was initiated by addition of 10 μl of decarboxylase solution (0.002-0.02 mM, final concentration). The sensitivity of the reaction depends on the concentration of buffer, lower concentrations give higher sensitivity. The values of $K_M$ and $k_{cat}$ were calculated from spectophotometrical measurements at 620 nm of the resulting blue solution using Lineweaver-Burk plot and the following equations:

$$\text{rate of reaction} = \frac{dA}{dt} * Q * \text{reaction volume}$$

where $$Q = \frac{C_{MOPS\ buffer}}{C_{BTB\ indicator}} * \frac{1}{\Delta\varepsilon_{620nm} * l} \text{ and } \Delta\varepsilon_{616nm} = 15703.79 \text{ M}^{-1}\text{cm}^{-1}.^{17,18}$$

h) In Vitro Decarboxylation of 2-methyl-2-phenylmalonate to 2-phenylpropanoic Acid by AMDase from *Bordetella bronchiseptica* and Asp/Glu Racemase from *Mesorhizobium* sp. BNC1.

To 400 μl of 0.1 M TRIS buffer pH 8, 100 μl of 0.5 M water solution (after adjusting pH to 8) of 2-methyl-2-phenylmalonic acid was added. Then 20 μl of an AMDase solution (10 mg/mL) was added and the reaction was stirred at 30° C. for 8 h. Products were extracted with diethyl ether after acidifying with 1 M HCl and methylated with TMS-diazomethane. The reaction was analyzed by GC (conversion up to 95%) and 2-phenylpropanoic acid formation confirmed by GC-MS, $^1$H NMR. Both enzyme products (after methylation) had the same configuration (the same peak on GC with chiral column, ee>99%). Thus according to the literature[7] absolute configuration of the product was R.

i) Substrates for Enzymatic Reactions

Phenylmalonate (1) was purchased from Sigma-Aldrich

2-Ethyl-2-phenylmalonate was a kind gift from BASF SE. Diethyl 2-methyl-2-phenylmalonate (2a) was synthesized from diethyl phenylmalonate in reaction with iodomethane. 10 g (42.3 mmol) of diethyl phenylmalonate was stirred for an hour under reflux in sodium ethanolate solution prepared by dissolving 1.6 g (69.5 mmol) metallic sodium in 60 mL of absolute ethanol. Then 6 mL (96.4 mmol) of MeI was added and the resulting mixture was stirred under reflux for another hour. After reaction the solvent was removed under vacuum and the remaining residue was dissolved in diethyl ether and dried over anhydrous magnesium sulphate. Diethyl ether was evaporated and the final product (pale oil) was obtained with a yield of 98% and purity of 99% according to NMR analysis.

2-Methyl-2-phenylmalonic acid (2) was synthesized from diethyl 2-methyl-2-phenylmalonate (2a) by hydrolysis in sodium hydroxide. 4 g (16 mmol) of diethyl 2-methyl-2-phenylmalonate was dissolved in 100 mL of ethanol and 50 mL of 3.25 M aqueous solution of sodium hydroxide was added. The reaction was stirred overnight at room temperature. Ethanol was then evaporated under vacuum and the resulting white powder was dissolved in 10 mL of water, cooled on ice and acidified with 5 M HCl to pH 1. The product was extracted with 2×100 mL of diethyl ether and dried over anhydrous magnesium sulphate. Ether was evaporated to give the final product (white powder) with a yield of 97% and purity of 99% as assayed by $^1$H NMR.

Diethyl 2-propylidenemalonate (4a), diethyl 2-butylidenemalonate (5a) and diethyl 2-(2-methylpropylidene)malonate (6a) were prepared by reaction of diethyl malonate with propionaldehyde, butyraldehyde and isobutyraldehyde respectively. 16 g (0.1 mol) of diethylmalonate was stirred together with 0.4 ml of piperidine and 1.2 ml of glacial acetic acid in 50 ml of toluene for 20 minutes. Then 0.12 mol of appropriate aldehyde was added and reaction was refluxed under Dean-Stark conditions for 4 h. 100 ml of water acidified with hydrochloric acid was added to the reaction mixture and product was extracted with diethyl ether. Organic layer was washed few times with brine solution and dried over magnesium sulphate. All product were purified by flash column chromatography. Products were obtained with yield up to 80% as colourless oils.

Diethyl 2-ethylidenemalonate (3a) was purchased from Sigma-Aldrich.

Diethyl 2-methyl-2-vinylmalonate (3b), diethyl 2-methyl-2-((E)-prop-1-enyl)malonate (4b), diethyl 2-methyl-2-((E)-but-1-enyl)malonate (5b) and diethyl 2-methyl-2-(2-methylprop-1-enyl)malonate (6b) were obtained the same manner as shown below in diethyl 2-methyl-2-vinylmalonate (3b) synthesis.

2.4 ml of diisopropylamine in 15 ml anhydrous THF was cooled to −78° C. and 10.5 ml of BuLi (2.5M) in hexane was added dropwise. After 20 minutes 7.5 ml of DMPU and 2.8 g (0.014 mol) of diethyl 2-ethylidenemalonate (3a) was added. Reaction was stirred at −78° C. for 45 minutes and then 3.8 g of iodomethane was added. Reaction was left stirring to reach RT within 1 h and then was refluxed for 30 minutes. 70 ml of water acidified with hydrochloric acid was added to the reaction mixture and product was extracted with diethyl ether. Product was purified by flash column chromatography. Final ester was obtained as a colourless oil with 30% of yield. 2-methyl-2-vinylmalonic acid (3), diethyl 2-methyl-2-((E)-prop-1-enyl)malonic acid (4), diethyl 2-methyl-2-((E)-but-1-enyl)malonic acid (5) and diethyl 2-methyl-2-(2-methylprop-1-enyl)malonic acid (6) were synthesised from esters the same manner as described for 2-methyl-2-phenyl malonic acid (2) above.

k) $^{18}$O Labelling Experiments.

Step I: 10 μl (40 μmol) of diethyl 2-methyl-2-phenylmalonate (5) was mixed with 10 μl of DMSO and suspended in 500 μl of phosphate buffer pH 7 (for H$_2$$^{18}$O experiment: 0.5 mL buffer was evaporated to dryness and the remaining powder re-dissolved in 0.5 mL of H$_2$$^{18}$O and "labelled" buffer used for reaction) containing 5 mg of porcine liver esterase (15 units/mg lyophilized powder, Sigma-Aldrich). The reaction was stirred overnight at 30° C. Then the reaction was cooled down to 4° C., acidified with 1M HCl to pH 1 and the product extracted with diethyl ether. Monoethyl 2-methyl-2-phenylmalonate was identified by $^1$H NMR and after methylation with TMS-diazomethane, by GC-MS (with isotopes analysis). The enantioselectivity of monoethyl 2-methyl-2-phenylmalonate was confirmed by HPLC-analysis on a chiral column Chiracel-OD. The separation of enantiomer peaks was achieved with a flow of 0.25 mL/min at 260 nm, by using a mixture of hexane-iso-propanol-trifluoroacetic acid (93:7:1.5) The formed product had configuration R according to literature data.[14]

Step II: Product from step I was dissolved in 150 µl of dry ethanol and 55 µl of 8.75 M NaOH was added (for $H_2^{18}O$ experiment: 100 mg of metallic sodium was dissolved in 55 µl of $H_2^{18}O$, obtained $Na^{18}OH$ was used for reaction). The reaction was stirred for 2.5 h at 30° C. The reaction was evaporated to dryness and dissolved in cold (4° C.) 0.1 M TRIS buffer pH 8 (400 and pH µl) and pH was adjusted with 1M HCl to 8. ⅓ of the mixture was acidified with 1M HCl to pH 1 and the product extracted with diethyl ether. 2-methyl-2-phenylmalonic was identified by $^1$H NMR and after methylation with TMS-diazomethane, by GC-MS (with isotopes analysis).

Step III: To the remaining solution from step II, 20 µl of an AMDase solution (10 mg/mL) was added and the reaction mixture was stirred for 4.5 h (overnight for AMDase from *Mesorhisobium* sp.) at 30° C. After this period the mixture was cooled down to 4° C. acidified with 1M HCl to pH 1 and the final product extracted with diethyl ether. 2-phenylpropanoic acid was identified by $^1$H NMR and, after methylation with TMS-diazomethane, by GC-MS (with isotopes analysis). The enantioselectivity (ee>99%) of the product (after methylation) was confirmed by GC with a chiral column.

2. Examples

Example 1

Overproduction and Activity of the *B. bronchiseptica* AMDase

A synthetic gene encoding the *B. bronchiseptica* AMDase with codon optimization for expression in *E. coli*, was subcloned into the pET30b vector. Expression in *E. coli* BL21 (DE3) strain following induction with IPTG resulted in the AMDase as a C-terminal $His_6$-fusion protein. The enzyme was then purified by Ni-affinity chromatography to greater than 95% purity as evidenced by SDS-PAGE and the molecular weight was confirmed by ESI-MS (m/z found 25 799, calc'd 25 800 Da)

Arylmalonate decarboxylase activity was first tested with intact *E. coli* cells possessing the AMDase expression vector using a modification of a procedure reported in the literature,[4] which uses bromothymol blue (BTB) as a pH indicator and phenylmalonate 1 as a substrate. In the presence of IPTG decarboxylation of the substrate by the AMDase was evident by a clear change in colour from yellow to blue. A similar colour change was noted with 2-methyl-2-phenylmalonate 2 as the substrates. The in vitro kinetic parameters of the decarboxylases were determined using a modification of a known UV spectrophotometric assay which relies on the change in absorption at 620 nm of BTB with increasing concentration of hyroxide ion[4] following decarboxylation. From this, apparent kinetic parameters were determined with phenylmalonate and 2-methyl-2-phenylmalonate 2 as substrates (Table 1). Overall the kinetic constants agree with those determined for the native enzyme and suggest that the $His_6$-tag has little effect on the activity of the AMDase. However, $k_{cat}$ for 2-methyl-2-phenylmalonate was higher than reported previously.[6]

TABLE 1

Kinetic constants for tested enzymes using phenylmalonate and 2-methyl-2-phenylmalonate as substrates (determined with BTB spectrophotometrical method).

| Protein | 2-phenylmalonic acid (1) | | | 2-methyl-2-phenylmalonic acid (2) | | |
|---|---|---|---|---|---|---|
| | $K_m$ [M] | $k_{cat}$ [$s^{-1}$] | $k_{cat}/K_m$ [$s^{-1}*M^{-1}$] | $K_m$ [M] | $k_{cat}$ [$s^{-1}$] | $k_{cat}/K_m$ [$s^{-1}*M^{-1}$] |
| AMDase from *Bordetella bronchiseptica* | $10.7*10^{-3}$ $(13.9*10^{-3})^a$ | 316.1 $(353)^a$ | 29630 $(25390)^a$ | $26.9*10^{-3}$ $(25.5*10^{-3})^a$ | 278.9 $(29.8)^a$ | 10370 $(1160)^a$ |
| protein EAN08019.1 from *Mesorhizobium* sp. BNC1 | $9.6*10^{-3}$ | 118 | 17100 | $22.2*10^{-3}$ | 55.8 | 2510 |
| protein NP_888076.1 from *Bordetella bronchiseptica* RB50] | $10*10^{-3}$ | 12.4 | 1240 | No reaction | | |
| glutamate racemase from *Aquifex pyrophilus* | $3.1*10^{-3}$ $(0.21*10^{-3})^b$ | 0.24 $(3.3)^b$ | 77 $(15710)^b$ | No reaction | | |
| protein BAA30082.1 from *Pyrococcus horikoshii* OT3 | $41.7*10^{-3}$ | 0.09 | 2.2 | No reaction | | |
| protein ZP_00801202.1 from *Alkaliphilus metalliredigenes* QYMF | $123*10^{-3}$ | 0.26 | 2.1 | No reaction | | |

$^a$literature data for AMDase from *Bordetella bronchiseptica*,[6]
$^b$glutamate racemase (kinetic constants for racemase activity) from *Aquifex pyrophilus*[10]

Example 2

Structure of the *B. bronchiseptica* AMDase a) AMDase Crystallization by the Sitting Prop Technique

*B. bronchisepticus* AMDase as obtained according to example 1 was concentrated to 10 mg/mL and sitting drops were prepared using 2 µL mixed with 2 µL of mother liquor consisting of Tris (0.1 M, pH 8.5) and PEG 6000 (30%). Trays were incubated at 21° C. and small crystals appeared after 1 week. Crystals belong to the $P2_1$ space group with unit cell a=38.7, b=65.6, c=42.2 Å, β=110.8° and solvent content of ~34%. A complete data set to 1.5 Å could be collected on a single crystal flash-cooled to 100K after addition of 10% PEG 200 as a cryo-protectant (see Table 2). Diffraction images were analyzed and data scaled using Crystal Clear.

The phosphate anion, which binds in the active site of AMDase, as revealed by crystal structure analysis, derives from the FPLC purification process, where phosphate buffer was used as an eluting buffer.

The position of heavy atom sites for two isomorphous lead chloride derivatives was found by manual interpretation of the difference Patterson functions. The sites located were used to run r resolve to generate experimental MIRAS phases, followed by autobuilding of a partial AMDase model using Arp/Warp. The resultant model was completed and refined using Coot and Refmac 5.

TABLE 2

Crystallography data of AMDase from *B. bronchisepticus*
Crystallography data

| | |
|---|---|
| Wavelength (Å) | 1.0 |
| Resolution (Å) | 20-1.50 (1.55-1.50) |
| Total reflections | 102017 |
| Unique reflections | 30804 |
| Data completeness (%) | 97.2 (91.1) |
| Average redundancy | 3.3 (3.1) |
| I/o/I) | 8.5 (2.7) |
| $R_{merge}$ | 0.093 (0.292) |
| $R_{fac}/R_{free}$ | 15.3/19.2 |
| Overall B-factors (Å$^2$) | |
| Protein | 11.9 |
| Water molecules | 24.6 |
| PO$_4$ | 12.1 |
| Rmsd | |
| Bond Length (Å) | 0.011 |
| Bond Angle (°) | 1.421 | b) Determination of AMDase Structure

The AMDase structure was solved to a nominal resolution of 1.45 Å using multiple isomorphous replacement with anomalous scattering (MIRAS) with two lead chloride derivatives. The structure reveals overall similarity with the crystal structures of Asp/Glu racemases,[10,12] despite the apparent differences in catalytic functionality. The crystals were relatively small, but due to the unusually low solvent content (approx 22%) diffraction was very strong. The structure is clearly a tightly folded monomer, which surprisingly possesses a single phosphate molecule bound near the active site Cys188, at the centre of a solvent accessible channel between the ends of β-sheets (FIG. 4(a)). The phosphate presumably mimics the carboxylate group of the proposed enolate intermediate, with two out of four oxygens bound by a classic oxy-anion hole arrangement (FIG. 4(b)). Single isolated oxyanion holes have been described in many protein structures, (Robertus, J. D., Kraut, J., Alden, R. A. & Birktoft, J. J. Subtilisin; a stereochemical mechanism involving transition-state stabilization. Biochemistry 11, 4293-4303 (1972)). However the presence of two of these in the form of the dioxyanion hole predicted to stabilize high-energy enediolate type intermediates has not been described before.

$O_1$ is bound by the side chain of Tyr126, and by both the amide backbone and hydroxyl side chain of Ser76. $O_2$ on the other hand is bound by the amide backbone of Gly189 in addition to both the hydroxyl and amide backbone of Thr75. It cannot be established from hydrogen bonding patterns alone whether either or both O atoms are deprotonated. In addition, the phosphate $O_3$ is hydrogen bonded to the Cys188 side chain. However, very little additional direct contacts are made between the phosphate molecule and the remaining residues of the AMDase.

Whilst the true biological substrate for this enzyme is not known, the prochiral 2-methyl-2-phenylmalonate 2 has been widely used as the model substrate. Initially therefore the proposed enolate intermediate derived from the decarboxylation of this substrate was modelled in to the active site of the structure (FIG. 5). The model uses the coordinates of the $O_1$—P—$O_2$ atoms of the original phosphate group, in order to position the carboxylate group of the enolate into the oxy-anion hole. In the original structure, the active site cavity volume is predominantly hydrophobic in nature and extends above the $O_1$—P—$O_2$ atoms. There is relatively little space available directly above the $O_1$ group, while in comparison a large cavity extending into the solvent area is available directly above $O_2$. The large cavity is also ideally shaped for binding of aromatic groups, with the Pro14 side chain positioned approximately 8 Å away from the Gly189-Gly190 amide bond, allowing for ideal VDW stacking of a flat aromatic system in between. From the available active site volume, it seems the enzyme will be able to accommodate relatively bulky ortho-, meta- and para-groups including a 2-naphthyl substituent, which is in line with the previously determined substrate specificity of this enzyme.[6,13] The fact that there is little space available above $O_1$ clearly indicates that this is most likely to accommodate the smaller methyl substituent. The model of the proposed intermediate, bound in this way (FIG. 5), positions the Cys188 thiol in close contact to si-face of the enolate, which is consistent with a subsequent protonation step leading to the R-configured 2-phenyl propionate product.

Example 3

Active Site Modifications

Further analysis of the crystal structure, with the proposed enolate intermediate docked in the active site, revealed the amino acid residues Leu40, Val43, Val156, Tyr48 and Met159 (situated on the opposite side to the carboxylate that is lost) make up the smaller hydrophobic binding pocket that might accommodate the methyl substituent (FIG. 5).

Accordingly three individual single mutants Leu40Ala, Val43Ala and Val156Ala were generated by site-directed mutagenesis.

The following primers (forward and reverse) were used for each site directed mutagenesis (obtained from SigmaAldrich)

```
L40A_F
GAGCGGCCTGGGCGCGGGTAGCGTTAC    (SEQ ID NO: 17)

L40A_R
GTAACGCTACCCGCGCCCAGGCCGCTC    (SEQ ID NO: 18)

V43A_F
CCTGGGTAGCGCAACCCCGGAAGGC      (SEQ ID NO: 19)

V43A_R
GCCTTCCGGGGTTGCGCTACCCAGG      (SEQ ID NO: 20)

V156A_F
GCATTACCGGCGCGGAAGCGATGGC      (SEQ ID NO: 21)

V156A_R
GCCATCGCTTCCGCGCCGGTAATGC      (SEQ ID NO: 22)
```

While the preparation of mutants of the present invention is exemplified for said three specific single mutants of one specific AMDase (BAA02419.1), a skilled reader will be enabled to introduce by means of substantially identical processes mutations at any position of the amino acid sequence in order to modify the activity profile of enzyme of the invention.
Selected Site-Directed Mutagenesis Primers:

```
Pro14Ala_F
                                       (SEQ ID NO: 23)
CATTGGCATGATTGTGGCGCCGGCAGCGGGTC
```

-continued

```
Pro14Ala_R
                                          (SEQ ID NO: 24)
GACCCGCTGCCGGCGCCACAATCATGCCAATG

P14G_F
                                          (SEQ ID NO: 25)
CATTGGCATGATTGTGGGTCCGGCAGCGGGTCTG

P14G_R
                                          (SEQ ID NO: 26)
CAGACCCGCTGCCGGACCCACAATCATGCCAATG

G189A_F
                                          (SEQ ID NO: 27)
CTGCTGTCTTGCGCGGGTCTGCTGACC

G189A_R
                                          (SEQ ID NO: 28)
GGTCAGCAGACCCGCGCAAGACAGCAG

G190A_F
                                          (SEQ ID NO: 29)
CTGCTGTCTTGCGGCGCGCTGCTGACCCTGGATG

G190A_R
                                          (SEQ ID NO: 30)
CATCCAGGGTCAGCAGCGCGCCGCAAGACAGCAG

G189A + G190A_F
                                          (SEQ ID NO: 31)
CATTCTGCTGTCTTGCGCGGCGCTGCTGACCCTGGATG

G189A + G190A_R
                                          (SEQ ID NO: 32)
CATCCAGGGTCAGCAGCGCCGCGCAAGACAGCAGAATG
```

Selected Site-Directed Saturated Mutagenesis Primers:

```
VAL13 + PRO14(SAT)_F
                                          (SEQ ID NO: 33)
CCCCGACCATTGGCATGATTNDTNDTCCGGCAGCGGGTCTGGTTC

VAL13 + PRO14(SAT)_R
                                          (SEQ ID NO: 34)
GAACCAGACCCGCTGCCGGAHNAHNAATCATGCCAATGGTCGGGG

PRO14 + PRO15(SAT)_F
                                          (SEQ ID NO: 35)
CGACCATTGGCATGATTGTGNDTNDTGCAGCGGGTCTGGTTCCGG

PRO14 + PRO15(SAT)_R
                                          (SEQ ID NO: 36)
CCGGAACCAGACCCGCTGCAHNAHNCACAATCATGCCAATGGTCG
```

Preparation of the mutants is performed as described above.

Example 4

Substrate Orientation and Mechanism of Decarboxylation

In order to further explore the possibility that hydrophobic interactions are important in decarboxylation, it was necessary to establish the likely orientation of the substrate in the active site. To do this, $^{18}O$ labelling experiments were carried out to establish the stereochemical course of the reaction and thus identify which of the two prochiral carboxylate groups of the 2-methyl-2-phenylmalonate 2 substrate is lost during decarboxylation, and which one is bound to the oxy-anion hole (FIG. 8). Accordingly, pig liver esterase (PLE) was used to catalyse the enatioselective hydrolysis of 2-methyl-2-phenylmalonate diethyl ester to give the (R)-monoester 6 in 98% e.e. in agreement with the literature.[14] This was then hydrolysed with $Na^{18}OH$ in $H_2{}^{18}O$ to give 2-methyl-2-phenylmalonic acids with an $^{18}O$ label in the pro-R carboxylate 7. Similarly the diester 5 was hydrolysed first with PLE in 98% $H_2{}^{18}O$ to give 8 and then subjected to saponification with unlabelled NaOH leading to 2-methyl-2-phenylmalonic acid with an $^{18}O$ label in the pro-S carboxylate 9. The chiral $^{18}O$ labelled malonates 7 and 9 were separately incubated with the AMDase. The products of the decarboxylation were then methylated with TMS-diazomethane and analysed by GC-MS. From this it was clear that the product (2-phenyl propanoate methyl ester) resulting from the (R)-malonate 7 (path A) had lost the $^{18}O$ label (m/z 164), whilst the product from (S)-malonate 9 (path B) had retained the $^{18}O$ label (m/z 166). This confirms that decarboxylation occurs, through the loss of the pro-R carboxylate with overall inversion of configuration.[15]

Figure 1:
FIG. 1: (a) Decarboxylation reaction catalysed by AMDase; (b) proposed mechanism of decarboxylation reaction catalysed by AMDase from B. bronchiseptica.
Figure 1:
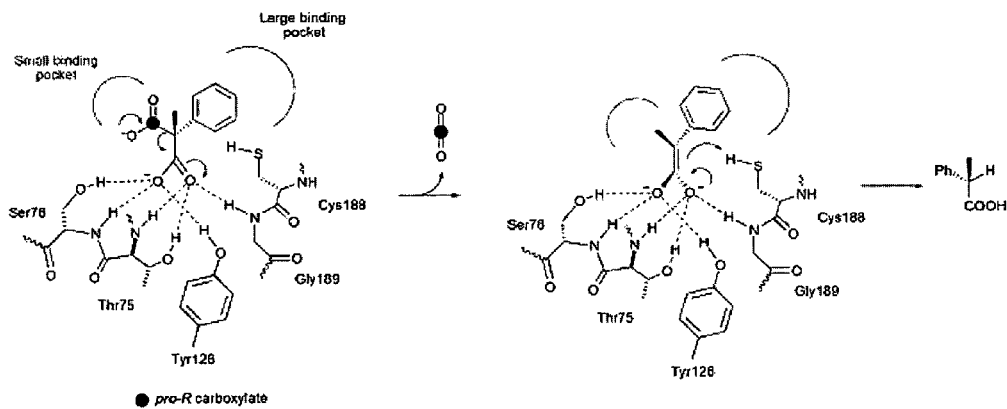

With the stereochemical course of the reaction established it was possible to position the substrate 2-methyl-2-phenylmalonate in the active site of the AMDase structure (FIG. 6). With the position of the pro-S carboxylate determined by the oxy-anion hole and phenyl substituent located in the solvent exposed pocket it is clear that the pro-S carboxylate occupies the opposite side of the active site to the Cys188 residue and is indeed tightly bound by the Leu40, Val43, Val156, Tyr48 hydrophobic pocket (FIG. 7). Indeed, from the model it is possible to conclude that mutation of Leu40Ala would serve to create sufficient space for at least one water molecule to bind and stabilise the pro-R carboxylate, thus retarding decarboxylation. The fact that Leu40 is essential for decarboxylase activity, whilst Val43, Val156 are apparently required for correct folding of the protein indicates the importance of these residues for the enzyme to adopt the correct functional conformation. Furthermore, these findings suggest that hydrophobic destabilisation of the pro-R carboxylate of the malonate substrate is a driving force for decarboxylation, resulting in delocalisation of electron density into the pro-S carboxylate of the enolate intermediate stabilised by the oxy-anion hole (FIG. 1(b)). Thus the enzyme is able to effect efficient decarboxylation without co-factors or prior activation as an electron-withdrawing thioester, simply by orientating the malonate substrate such that one carboxyl group is stabilised by an extensive network of H-bonding, whilst the other carboxylate is deprived of any such stabilising interactions.

Example 5

Identification and Catalytic Properties of Other AMDase Related Enzymes

Despite the significant promise of the AMDases for applications in biocatalysis, only one such enzyme has been isolated and characterised to date. However, searches in the protein databases reveal that there are many proteins, most of unknown function, that share sequence similarity to the B. bronchiseptica AMDase. Four protein sequences which show moderate to high similarity to the AMDase (FIG. 3 (a),(b)) and which contain a cysteine at the same relative position as the Cys188 in the B. bronchiseptica enzyme, were selected for investigation (Table 3).

TABLE 3

Enzymes selected for the search of arylmalonate decarboxylase activity and their molecular weights determined by ESI-MS.

| No. from BLAST database | Microorganism | Proposed function | No of amino acid in 6xHis-Tagged proteins | Identity to AMDase [%] (no. of overlapped amino acids) | Mw [D] found | Mw [D] calculated |
|---|---|---|---|---|---|---|
| BAA02419.1 | Bordetella bronchiseptica | Arylmalonate decarboxylase | 248 | 100 (240) | 25 799 | 25800 |
| EAN08019.1 | Mesorhizobium sp. BNC1 | Asp/Glu racemase | 248 | 52 (219) | 25770 | 25771 |
| NP_888076.1 | Bordetella bronchiseptica RB50 | Putative decarboxylase | 273 | 36 (237) | 29953 | 29950 |
| ZP_00801202.1 | Alkaliphilus metalliredigenes QYMF | Asp/Glu racemase | 251 | 34 (183) | 27413 | 27410 |
| BAA30082.1 | Pyrococcus horikoshii OT3 | Hypothetical arylmalonate decarboxylase | 246 | 30 (214) | 27816 | 27818 |
| AAF25672 | Aquifex pyrophilus | Glutamate racemase | 262 | — | 29060 | 29058 |

Accordingly genes encoding these proteins were synthesised with codons optimised for *E. coli*. The synthetic genes were cloned, over-expressed in *E. coli*. and purified as His$_6$-fusion proteins as described above. SDS-PAGE confirmed that all the proteins were of greater than 95% purity and ESI mass spectroscopy of all the proteins agreed with the calculated values (Table 3). In addition to this, a known glutamate racemase from *Aquifex pyrophilus* was overproduced and purified. The sequence of this glutamate racemase has little similarity, to the sequence of the AMDase from *B. bronchiseptica*. However it's structure[10] and mechanism which is based on the formation of an intermediate enolate with two cysteines serving in general acid-base catalysis is well established.[10,16] These facts made this enzyme an interesting candidate to study in order to establish if a native racemase could also demonstrate promiscuous decarboxylase activity.

The activity of the new enzymes was initially measured in vivo on plates (see FIGS. 9 and 10) with BTB and phenylmalonate as a substrate. Surprisingly all of the transformed colonies became blue after extended periods of incubation, whilst transformants with no gene inserted did not give rise to a colour change. This suggests that all of these enzymes can catalyse the decarboxylation reaction to some extent. Subsequently, apparent kinetic constants for the purified enzymes were established (Table 1). Notably the enzyme from *Mesorhizobium* sp. BNC1, which shows highest similarity to the *B. bronchiseptica* AMDase, showed very efficient decarboxylase activity with both phenylmalonate 1 and 2-methyl-2-phenylmalonate 2 as substrates. The *Bordetella bronchiseptica* RB50 enzyme shows moderate activity with phenylmalonate, whilst the enzymes from *Pyrococcus horikoshii* OT3 and *Alkaliphilus metalliredigenes* QYMF show very low levels of activity with phenylmalonate, which is in line with in vivo assay which indicated only slow development of colour for transformants possessing these enzymes. Interestingly the known glutamate racemase from *Aquifex pyrophilus* is able to catalyse the decarboxylation of phenylmalonate albeit with 196 fold lower activity than the native glutamate racemase activity. It is possible to rationalise these results through protein sequence alignments (FIG. 3(*a*)(*b*)). All enzymes possess oxy-anion hole, however only the *B. bronchiseptica* and the enzyme from *Mesorhizobium* sp. have the putative hydrophobic carboxylate binding pocket which is required to destabilise the $CO_2$ group that is lost on decarboxylation. The conclusion from this is that tight binding of one carboxylate into the oxy-anion hole is sufficient for decarboxylation, however for efficient decarboxylation the carboxylate group that is lost must be destabilised through hydrophobic contacts with the enzyme active site. These results indicate that decarboxylation of aryl malonates can be accomplished by a number of different enzymes, and this offers a number of possible starting points for engineering new decarboxylases with improved substrate specificities and biocatalytic activities.

Example 6

Structure and Mechanism of the AMDase from *Mesorhizobium* sp. BNC1

From the pool of new enzymes only the decarboxylase, from *Mesorhizobium* sp. BNC1, was proficient in decarboxylating the 2-methyl-2-phenylmalonate 2. In this case the 2-phenylpropionate product obtained after 2-methyl-decarboxylation was shown to possess the same R-configuration (ee>99%) as the decarboxylation product resulting from the AMDase from *Bordetella bronchiseptica*. Moreover $^{18}O$ labelling studies with (R)- and (S)-malonate 7 and 9 also indicate that the *Mesorhizobium* sp. BNC1 AMDase operates with the same stereochemistry as the *B. bronchiseptica* enzyme, loosing the pro-R carboxylate with overall inversion of configuration. Given the apparent mechanistic and sequence similarity to the *B. bronchiseptica* AMDase it was possible to generate a model of the *Mesorhizobium* sp. BNC1 AMDase active site (FIG. 6(*b* with the substrate 2-methyl-2-phenylmalonate 2 bound. This shows a very similar active site structure with oxy-anion hole accommodating the pro-S carboxylate group and a conserved hydrophobic pocket serving to destabilise the pro-R carboxylate. In addition a solvent accessible pocket exists which would ideally accommodate the phenyl group of the substrate. Taken together this confirms that this enzyme possesses a similar mechanism and structure as the *B. bronchiseptica* AMDase. In addition to proving valuable information for the design of new decarboxylases, these observations raise some interesting questions as to why these quite different organisms possess similar enzymes with no obvious function in primary or secondary metabolism. Clearly it remains to be seen what physiological role this class of enzymes might fulfil in nature.

Example 7

Activity of the *B. bronchiseptica* KU 1201 and *Mesorhizobium* sp BNC1 AMDases for Different Alkenyl-Substituted Substrates of Formula I A BTB activity assay was performed as described above. Compounds of formula I, wherein $R^2$ is methyl and $R^1$ is phenyl, ethenyl, propen-1-yl, buten-1-yl or 2-methylpropen-1-yl were tested as substrates. The results are summarized in following Table 4:

TABLE 4

Kinetic constants for different compound of formula I at 30° C. determined by BTB assay.

| | Substrate Compound of formula I $R_1$ = methyl | | | | | |
|---|---|---|---|---|---|---|
| | AMDase from *Bordetella bronchiseptica* KU1201 | | | AMDase from *Mesorhizobium* sp. BNC1 | | |
| $R_2=$ | $K_m$ (mM) | $k_{cat}$ (s$^{-1}$) | $k_{cat}/K_m$ (s$^{-1}$*mM$^{-1}$) | $K_m$ (mM) | $k_{cat}$ (s$^{-1}$) | $k_{cat}/K_m$ (s$^{-1}$*mM$^{-1}$) |
| ethenyl (3) | 7.8 | 42.8 | 5.5 | 19.4 | 8.9 | 0.46 |
| propen-1-yl (4) | 12.8 | 46.2 | 3.6 | 29.0 | 10.2 | 0.35 |
| n-buten-1-yl (5) | 14.4 | 23.9 | 1.6 | 32.5 | 7.7 | 0.24 |
| 2-methyl-propen-1-yl (6) | 3.5 | 5.2 | 1.5 | 6.3 | 0.7 | 0.11 |

The data show that each of the tested alkenyl-substituted, non-aromatic compounds is decarboxylated by each of said two different AMDase enzymes. For non-aromatic residues $R^1$ the fastest reaction was observed for $R^1$=entenyl

Example 8

Determination of Optical Purity and Absolute Configuration of Monoacids Formed by of the *B. bronchiseptica* KU 1201 and *Mesorhizobium* sp BNC1 AMDases for Different Alkenyl-Substituted Substrates of Formula I Different non-aromatic substrates were decarboxylated by the AMDases from *Bordetella bronchiseptica* KU1201 and *Mesorhizobium* sp. BNC1 as shown I the subsequent scheme:

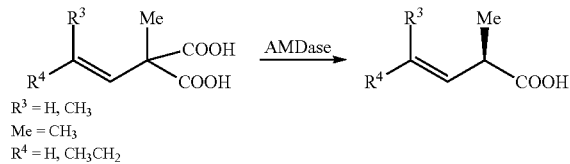

$R^3$ = H, CH$_3$
Me = CH$_3$
$R^4$ = H, CH$_3$CH$_2$

The conditions of said enzymatic reactions are the same as described for aryl-malonates (see above) just the reaction time is longer. Usually after 24 h all the substrate has been converted.

The reaction of said unsaturated aliphatic malonates goes to the completion (>99% of conversion). The product can be recovered in pure form (as determined by NMR) by extraction with diethyl ether from an acidified aqueous layer after termination of the enzymatic reaction. Usually, no additional step of purification is required.

Reactions were performed on a 200 mg scale, and the observed yields of pure recovered product were around 90-95%.

In order to analyze the reaction product the obtained monoacids were derivatised with diazomethane to the corresponding methyl esters. The ee values of said methyl esters were then determined by means of gas chromatography applying a chiral column Varian Chirasil-Dex CB (25 m×250 μm×0.26 μm) under the following temperature conditions: hold at 50° C. for 30 min., then gradient 10° C./min until temperature reaches 200° C., then hold for 5 min at 200° C.

Retention Time Values:
methyl 2-methylbut-3-enoate: 12.286 min (enantiomer (R)) and 12.350 min (S),
methyl (E)-2-methylpent-3-enoate: 24.984 min (S) and 27.823 min (R);
methyl (E)-2-methylhex-3-enoate: 34.324 min (S) and 34.885 min (R);
methyl 2,4-dimethylpent-3-enoate: 33.679 min (R) and 34.254 min (S).

Monoacids were obtained with ee>99% for each of the two AMDase enzymes from *Bordetella bronchiseptica* KU1201 and *Mesorhizobium* sp. BNC1.

The absolute configuration of the obtained monoacids is (R), the same as for arylmalonates. Absolute configuration was determined by the comparison of measured optical rotatory power with corresponding literature data.

Corresponding non-aromatic HO-substituted substrates (wherein Me is replaced by hydroxy) are decarboxylated as well as assayed by colorimetric screening methods (data not shown).

Concluding General Remarks on the Present Invention

The first X-ray crystal structure of a co-factor independent aryl malonate decarboxylase (AMDase), from *Bordetella bronchiseptica*, has been presented with phosphate bound to the active site. This reveals the presence of oxy-anion hole, which are required to bind one of the substrate carboxylate and stabilise the formation of a putative enolate intermediate. In addition a solvent accessible cavity is evident which can accommodate the large aryl substituent of typical substrates, whilst a tight hydrophobic pocket restricts the size of the additional aliphatic malonate substituents. Using $^{18}O$ labelling studies it was possible to establish that the decarboxylation of the model substrate 2-methyl-2-phenylmalonate occurs with inversion of stereochemistry and loss of the pro-R carboxylate, this allows a model of the substrate bound to the active site to be generated. This model shows that the pro-R carboxylate of the substrate lost during decarboxylation is tightly bound by the hydrophobic pocket, which is postulated to destabilise the negative charge on the carboxylate, providing the necessary driving force for decarboxylation in the absence of co-factors or acyl enzyme intermediates. The structural and mechanistic importance of this hydrophobic pocket is exemplified by site-directed mutagenesis of the hydrophobic residues to Ala, which either results in misfolding or complete loss of activity. Following decarboxylation the resulting enolate, which is stabilised by the oxy-anion hole, is then protonated from the si-face by the active site Cys188 residue leading to (2R)-phenyl propionic acid.

In addition to this, four new enzymes that exhibit similarity to the *B. bronchiseptica* AMDase, are shown to catalyse decarboxylation of aryl malonate substrates. One of these enzymes from *Mesorhizobium* sp. BNC1, was found to possess similar substrate specificity, catalytic efficiency and stereochemistry as the original *B. bronchiseptica* AMDase. Moreover the sequence similarity between the two enzymes allowed a structural model of the AMDase from *Mesorhizobium* to be generated, which supports the hypothesis that the two AMDases share a common mechanism. Furthermore the known glutamate racemase, from *Aquifex pyrophilus*, which is predicted to possess a similar catalytic mechanism, was also shown to possess promiscuous aryl malonate decarboxylase activity despite exhibiting little sequence similarity to the AMDase.

Overall these combined results provide the key structural and mechanistic insight that is necessary for engineering new decarboxylase enzymes, either by rational mutagenesis or directed evolution. Said techniques are for example disclosed in 1) Roberto A Chica, Nicolas Doucet and Joelle N Pelletier, Semi-rational approaches to engineering enzyme activity: combining the benefits of directed evolution and rational design, *Current Opinion in Biotechnology*, 16, 4, 2005, 378-384,
2) Enzyme functionality: Design, engineering, and screening edited by Allan Svendsen, Marcel Dekker, Inc., New York, Basel 2003
3) Paul A. Dalby Engineering Enzymes for Biocatalysis *Recent Patents on Biotechnology* 2007, 1, 1-9

This is an important improvement as the high stereoselectivity afforded by the AMDases enables the preparation of valuable homochiral carboxylic acids from cheap accessible malonate precursors.

Documents cited herein are incorporated by reference.

REFERENCES

1. Dimroth, P., Hilbi, H., Enzymic and genetic basis for bacterial growth on malonate. *Mol. Microbiol.* 1997, 25, (1), 3-10.
2. Hoenke, S., Wild, M. R., Dimroth, P., Biosynthesis of triphosphoribosyl-dephospho-coenzyme A, the precursor of the prosthetic group of malonate decarboxylase. *Biochemistry* 2000, 39, (43), 13223-32.
3. Miyamoto, K., Ohta, H., Asymmetric decarboxylation of disubstituted malonic acid by *Alcaligenes bronchisepticus* KU1201. *Biocatalysis* 1991, 5, 49-60.
4. Miyamoto, K., Ohta, H., Cloning and heterologous expression of a novel arylmalonate decarboxylase gene from *Alcaligenes bronchisepticus* KU 1201. *Appl Microbiol Biotechnol* 1992, 38, 234-238.
5. Miyamoto, K., Ohta, H., Enzyme-mediated asymmetric decarboxylation of disubstituted malonic acids. *J Am Chem Soc* 1990, 112, 4077-4078
6. Miyamoto, K., Ohta, H., Purification and properties of a novel arylmalonate decarboxylase from *Alcaligenes bronchisepticus* KU 1201. *European Journal of Biochemistry* 1992, 210, (2), 475-81.
7. Terao, Y., Miyamoto, K., Ohta, H., Introduction of single mutation changes arylmalonate decarboxylase to racemase. *Chemical Communications* 2006, 34, 3600-3602.
8. Matoishi, K., Ueda, M., Miyamoto, K., Ohta, H., Mechanism of asymmetric decarboxylation of α-aryl-α-methyl-malonate catalyzed by arylmalonate decarboxylase originated from *Alcaligenes bronchisepticus*. *Journal of Molecular Catalysis B: Enzymatic* 2004, 27, (4-6), 161-168.
9. Glavas, S., Tanner, M. E., Active site residues of glutamate racemase. *Biochemistry* 2001, 40, (21), 6199-6204
10. Hwang, K. Y., Cho, C. S., Kim, S. S., Sung, H. C., Yu, Y. G., Cho, Y., Structure and mechanism of glutamate racemase from *Aquifex pyrophilus*. *Nature structural biology* 1999, 6, (5), 422-426.
11. Terao, Y., Ijima, Y., Miyamoto, K., Ohta, H., Inversion of enantioselectivity of arylmalonate decarboxylase via site-directed mutation based on the proposed reaction mechanism. *Journal of Molecular Catalysis B: Enzymatic* 2007, 45, (1-2), 15-20
12. Liu, L., Iwata, K., Kita, A., Kawarabayasi, Y., Yohda, M., Miki, K., Crystal structure of aspartate racemase from *Pyrococcus horikoshii* OT3 and its implications for molecular mechanism of PLP-independent racemization. *J. Mol. Biol.* 2002, 319, 479-489.
13. Miyamoto, K., Ohta, H., Osamura, Y., Effect of Conformation of the Substrate on Enzymatic Decarboxylation of a-Arylmalonic Acid. *Bioorganic and Medicinal Chemisby* 1994, 2, (6), 469-475.
14. Dominguez de Maria, P., Kossmann, B., Potgrave, N., Buchholz, S., Trauthwein, H., May, O., Groeger, H., Improved process for the enantioselective hydrolysis of prochiral diethyl malonates catalyzed by pig liver esterase. *Synlett* 2005, 11, 1746-1748.
15. Miyamoto, K., Tsutsumi, T., Terao, Y., Ohta, H., Stereochemistry of Decarboxylation of Arylmalonate Catalyzed by Mutant Enzymes. *Chemistry Letters* 2007, 36, (5), 656-657.
16. Handa, S., Koo, J. H., Kim, Y. S., Floss, H. G., Stereochemical Course of BiotinIndependentMalonate Decarboxylase Catalysis. *Archives of Biochemistry and Biophysics* 1999, 370, (1), 93-96.
17. Janes, L. E., Lowendahl, A. Ch., Kazlauskas, R. J., Quantitative screening of hydrolase libraries using pH indicators: identifying active and enantioselective hydrolases. *Chemistry-A European Journal* 1998, 4, (11), 2324-2331.
18. Banerjee, A., Kaul, P., Sharma, R., Banerjee, U. C., A high-throughput amenable colorimetric assay for enantioselective screening of nitrilase-producing microorganisms using pH sensitive indicators. *Journal of Biomolecular Screening* 2003, 8, (5), 559-565.

SEQUENCE LISTING

<160> NUMBER OF SEQ ID NOS: 36

<210> SEQ ID NO 1
<211> LENGTH: 744
<212> TYPE: DNA
<213> ORGANISM: Bordetella bronchiseptica
<220> FEATURE:
<221> NAME/KEY: CDS
<222> LOCATION: (1)..(744)

<400> SEQUENCE: 1

```
atg cag cag gcg agc acc ccg acc att ggc atg att gtg ccg ccg gca      48
Met Gln Gln Ala Ser Thr Pro Thr Ile Gly Met Ile Val Pro Pro Ala
1               5                  10                  15 gcg ggt ctg gtt ccg gcg gat ggc gcg cgt ctg tat ccg gat ctg ccg      96
Ala Gly Leu Val Pro Ala Asp Gly Ala Arg Leu Tyr Pro Asp Leu Pro
            20                  25                  30 ttt att gcg agc ggc ctg ggc ctg ggt agc gtt acc ccg gaa ggc tat     144
Phe Ile Ala Ser Gly Leu Gly Leu Gly Ser Val Thr Pro Glu Gly Tyr
        35                  40                  45 gat gcg gtg att gaa agc gtg gtg gat cat gcg cgt cgt ctg cag aaa     192
Asp Ala Val Ile Glu Ser Val Val Asp His Ala Arg Arg Leu Gln Lys
50                  55                  60 cag ggt gcg gcg gtg gtg agc ctg atg ggc acc agc ctg agc ttt tat     240
Gln Gly Ala Ala Val Val Ser Leu Met Gly Thr Ser Leu Ser Phe Tyr
65                  70                  75                  80 cgt ggt gcg gcg ttt aac gcg gcg ctg acc gtg gcg atg cgt gaa gcg     288
Arg Gly Ala Ala Phe Asn Ala Ala Leu Thr Val Ala Met Arg Glu Ala
                85                  90                  95 acc ggt ctg ccg tgc acc acc atg tct acc gcg gtg ctg aat ggt ctg     336
Thr Gly Leu Pro Cys Thr Thr Met Ser Thr Ala Val Leu Asn Gly Leu
            100                 105                 110 cgt gcg ctg ggt gtg cgt cgt gtt gcg ctg gcc acc gcg tat atc gat     384
Arg Ala Leu Gly Val Arg Arg Val Ala Leu Ala Thr Ala Tyr Ile Asp
        115                 120                 125 gat gtg aac gaa cgt ctg gcc gcg ttt ctg gcc gaa gaa agc ctg gtg     432
Asp Val Asn Glu Arg Leu Ala Ala Phe Leu Ala Glu Glu Ser Leu Val
130                 135                 140 ccg acc ggt tgt cgt agc ctg ggc att acc ggc gtg gaa gcg atg gcg     480
Pro Thr Gly Cys Arg Ser Leu Gly Ile Thr Gly Val Glu Ala Met Ala
145                 150                 155                 160 cgt gtg gat acc gcg acc ctg gtg gat ctg tgc gtg cgt gcg ttt gaa     528
Arg Val Asp Thr Ala Thr Leu Val Asp Leu Cys Val Arg Ala Phe Glu
                165                 170                 175 gcg gca ccg gat agc gat ggc att ctg ctg tct tgc ggc ggt ctg ctg     576
Ala Ala Pro Asp Ser Asp Gly Ile Leu Leu Ser Cys Gly Gly Leu Leu
            180                 185                 190 acc ctg gat gcg att ccg gaa gtg gaa cgt cgt ctg ggc gtg ccg gtg     624
Thr Leu Asp Ala Ile Pro Glu Val Glu Arg Arg Leu Gly Val Pro Val
        195                 200                 205 gtt agc agc agc ccg gca ggc ttt tgg gat gcg gtg cgt ctg gcc ggt     672
Val Ser Ser Ser Pro Ala Gly Phe Trp Asp Ala Val Arg Leu Ala Gly
210                 215                 220 ggt ggt gcg aaa gcg cgt ccg ggc tat ggc cgt ctg ttt gat gaa agc     720
Gly Gly Ala Lys Ala Arg Pro Gly Tyr Gly Arg Leu Phe Asp Glu Ser
225                 230                 235                 240 ctc gag cac cac cac cac cac cac                                     744
Leu Glu His His His His His His
                245
```

<210> SEQ ID NO 2

<211> LENGTH: 248
<212> TYPE: PRT
<213> ORGANISM: Bordetella bronchiseptica

<400> SEQUENCE: 2

```
Met Gln Gln Ala Ser Thr Pro Thr Ile Gly Met Ile Val Pro Pro Ala
1               5                   10                  15

Ala Gly Leu Val Pro Ala Asp Gly Ala Arg Leu Tyr Pro Asp Leu Pro
            20                  25                  30

Phe Ile Ala Ser Gly Leu Gly Leu Gly Ser Val Thr Pro Glu Gly Tyr
        35                  40                  45

Asp Ala Val Ile Glu Ser Val Val Asp His Ala Arg Arg Leu Gln Lys
    50                  55                  60

Gln Gly Ala Ala Val Val Ser Leu Met Gly Thr Ser Leu Ser Phe Tyr
65                  70                  75                  80

Arg Gly Ala Ala Phe Asn Ala Ala Leu Thr Val Ala Met Arg Glu Ala
                85                  90                  95

Thr Gly Leu Pro Cys Thr Thr Met Ser Thr Ala Val Leu Asn Gly Leu
            100                 105                 110

Arg Ala Leu Gly Val Arg Arg Val Ala Leu Ala Thr Ala Tyr Ile Asp
        115                 120                 125

Asp Val Asn Glu Arg Leu Ala Ala Phe Leu Ala Glu Glu Ser Leu Val
    130                 135                 140

Pro Thr Gly Cys Arg Ser Leu Gly Ile Thr Gly Val Glu Ala Met Ala
145                 150                 155                 160

Arg Val Asp Thr Ala Thr Leu Val Asp Leu Cys Val Arg Ala Phe Glu
                165                 170                 175

Ala Ala Pro Asp Ser Asp Gly Ile Leu Leu Ser Cys Gly Gly Leu Leu
            180                 185                 190

Thr Leu Asp Ala Ile Pro Glu Val Glu Arg Arg Leu Gly Val Pro Val
        195                 200                 205

Val Ser Ser Ser Pro Ala Gly Phe Trp Asp Ala Val Arg Leu Ala Gly
    210                 215                 220

Gly Gly Ala Lys Ala Arg Pro Gly Tyr Gly Arg Leu Phe Asp Glu Ser
225                 230                 235                 240

Leu Glu His His His His His His
                245
```

<210> SEQ ID NO 3
<211> LENGTH: 747
<212> TYPE: DNA
<213> ORGANISM: Mesorhizobium sp.
<220> FEATURE:
<221> NAME/KEY: CDS
<222> LOCATION: (1)..(747)

<400> SEQUENCE: 3

```
atg agc gcg gaa gat ccg gtg att ggc ctg att gtt ccg ccg gca gca      48
Met Ser Ala Glu Asp Pro Val Ile Gly Leu Ile Val Pro Pro Ala Ala
1               5                   10                  15 ggt ctg gtt ccg ccg gaa gcg gtg gcg atg tat ccg gaa gtg acc ttt      96
Gly Leu Val Pro Pro Glu Ala Val Ala Met Tyr Pro Glu Val Thr Phe
            20                  25                  30 cat gcg agc ggc ctg ggc ctg aaa gaa atg acc ccg tgc ggc tat gcg     144
His Ala Ser Gly Leu Gly Leu Lys Glu Met Thr Pro Cys Gly Tyr Ala
        35                  40                  45 ggc gtg att gat ctg gtg ggc gat cat gcg gaa cgt cat gcg cag gcg     192
Gly Val Ile Asp Leu Val Gly Asp His Ala Glu Arg His Ala Gln Ala
```

```
                 50                  55                  60
ggt gcg cag gcg gtg gcg ctg atg ggc acc agc ctg agc ttt ttt cgt      240
Gly Ala Gln Ala Val Ala Leu Met Gly Thr Ser Leu Ser Phe Phe Arg
 65                  70                  75                  80 ggt gcg gcg ttt aac gcg gaa ctg att acc cac atg agc aac cgt agc      288
Gly Ala Ala Phe Asn Ala Glu Leu Ile Thr His Met Ser Asn Arg Ser
                     85                  90                  95 ggt ctg ccg gcg acc acc atg agc cag gcg gtg gtg gat gaa ctg aaa      336
Gly Leu Pro Ala Thr Thr Met Ser Gln Ala Val Val Asp Glu Leu Lys
                 100                 105                 110 agc cat ggc gcg cgt cgt att gcg gtg gtg acc gcg tat cgc cag gat      384
Ser His Gly Ala Arg Arg Ile Ala Val Val Thr Ala Tyr Arg Gln Asp
             115                 120                 125 gtg aac aac ctg ctg gcc gcg ttt ctg aac gaa cat ggc att gaa gcg      432
Val Asn Asn Leu Leu Ala Ala Phe Leu Asn Glu His Gly Ile Glu Ala
         130                 135                 140 cgt agc ctg aaa agc ctg ggc att acc agc gtg gcg gat gtt gcg ggc      480
Arg Ser Leu Lys Ser Leu Gly Ile Thr Ser Val Ala Asp Val Ala Gly
145                 150                 155                 160 acc ccg gcg aaa cgt ctg ctg cag ctg tgc aaa gaa gcg gtg cat gat      528
Thr Pro Ala Lys Arg Leu Leu Gln Leu Cys Lys Glu Ala Val His Asp
                 165                 170                 175 gcg ggt ccg gtg gat gcg gtg ctg att agc tgc ggt ggt ctg cat acc      576
Ala Gly Pro Val Asp Ala Val Leu Ile Ser Cys Gly Gly Leu His Thr
             180                 185                 190 ctg gat gtg att gtg gat gtg gaa atc agc acc ggc ctg ccg gtt gtt      624
Leu Asp Val Ile Val Asp Val Glu Ile Ser Thr Gly Leu Pro Val Val
         195                 200                 205 acc agc gcg acc gcg ggt gtg cgt ggt gcg gtg ggc ctg ctg aaa cgt      672
Thr Ser Ala Thr Ala Gly Val Arg Gly Ala Val Gly Leu Leu Lys Arg
210                 215                 220 agc gcg gaa acc gcg gaa cat gcg acc agc aaa ttt ctg acc ggc cgt      720
Ser Ala Glu Thr Ala Glu His Ala Thr Ser Lys Phe Leu Thr Gly Arg
225                 230                 235                 240 gcg ctc gag cac cac cac cac cac cac                                  747
Ala Leu Glu His His His His His His
                 245

<210> SEQ ID NO 4
<211> LENGTH: 249
<212> TYPE: PRT
<213> ORGANISM: Mesorhizobium sp.

<400> SEQUENCE: 4

Met Ser Ala Glu Asp Pro Val Ile Gly Leu Ile Val Pro Pro Ala
 1               5                  10                  15

Gly Leu Val Pro Pro Glu Ala Val Ala Met Tyr Pro Glu Val Thr Phe
                 20                  25                  30

His Ala Ser Gly Leu Gly Leu Lys Glu Met Thr Pro Cys Gly Tyr Ala
             35                  40                  45

Gly Val Ile Asp Leu Val Gly Asp His Ala Glu Arg His Ala Gln Ala
         50                  55                  60

Gly Ala Gln Ala Val Ala Leu Met Gly Thr Ser Leu Ser Phe Phe Arg
 65                  70                  75                  80

Gly Ala Ala Phe Asn Ala Glu Leu Ile Thr His Met Ser Asn Arg Ser
                     85                  90                  95

Gly Leu Pro Ala Thr Thr Met Ser Gln Ala Val Val Asp Glu Leu Lys
                 100                 105                 110
```

-continued

| | | | | | | | | | | | | |
|---|---|---|---|---|---|---|---|---|---|---|---|---|
| Ser | His | Gly | Ala | Arg | Arg | Ile | Ala | Val | Val | Thr | Ala | Tyr | Arg | Gln | Asp |
| | | 115 | | | | 120 | | | | 125 | | |

Val Asn Asn Leu Leu Ala Ala Phe Leu Asn Glu His Gly Ile Glu Ala
       130                 135                 140

Arg Ser Leu Lys Ser Leu Gly Ile Thr Ser Val Ala Asp Val Ala Gly
145                 150                 155                 160

Thr Pro Ala Lys Arg Leu Leu Gln Leu Cys Lys Glu Ala Val His Asp
                165                 170                 175

Ala Gly Pro Val Asp Ala Val Leu Ile Ser Cys Gly Gly Leu His Thr
            180                 185                 190

Leu Asp Val Ile Val Asp Val Glu Ile Ser Thr Gly Leu Pro Val Val
        195                 200                 205

Thr Ser Ala Thr Ala Gly Val Arg Gly Ala Val Gly Leu Leu Lys Arg
    210                 215                 220

Ser Ala Glu Thr Ala Glu His Ala Thr Ser Lys Phe Leu Thr Gly Arg
225                 230                 235                 240

Ala Leu Glu His His His His His His
                245

<210> SEQ ID NO 5
<211> LENGTH: 738
<212> TYPE: DNA
<213> ORGANISM: Pyrococcus horikoshii
<220> FEATURE:
<221> NAME/KEY: CDS
<222> LOCATION: (1)..(738)

<400> SEQUENCE: 5

```
atg tat ggc tgg cgt cgt cgt att ggc ctg att gtg ccg agc agc aac      48
Met Tyr Gly Trp Arg Arg Arg Ile Gly Leu Ile Val Pro Ser Ser Asn
1               5                   10                  15 acc acc atg gaa ccg gaa ttt tgg aaa atg gcg ccg gaa ggc gtg agc      96
Thr Thr Met Glu Pro Glu Phe Trp Lys Met Ala Pro Glu Gly Val Ser
                20                  25                  30 att cat acc gcg cgt atg cgt ctg cgt gaa gtg acc gaa gaa agc ctg     144
Ile His Thr Ala Arg Met Arg Leu Arg Glu Val Thr Glu Glu Ser Leu
            35                  40                  45 ctg gaa atg gaa cgt cat gcg aaa gat gcg gcg ctg gaa ctg gcc gat     192
Leu Glu Met Glu Arg His Ala Lys Asp Ala Ala Leu Glu Leu Ala Asp
    50                  55                  60 gcg gaa gtg gat gtg att gtg tat ggc tgc acc agc ggc agc ctg att     240
Ala Glu Val Asp Val Ile Val Tyr Gly Cys Thr Ser Gly Ser Leu Ile
65                  70                  75                  80 aaa ggc aaa ggc tat gat aaa gaa atc gcg aaa aac ctg gaa gaa gcg     288
Lys Gly Lys Gly Tyr Asp Lys Glu Ile Ala Lys Asn Leu Glu Glu Ala
                85                  90                  95 agc ggc att aaa acc att acc acc tct acc gcg gtt ctg aac gcg ctg     336
Ser Gly Ile Lys Thr Ile Thr Thr Ser Thr Ala Val Leu Asn Ala Leu
            100                 105                 110 aac acc ctg gat att cag aaa gtg gtg gtg gcg acc ccg tat att gat     384
Asn Thr Leu Asp Ile Gln Lys Val Val Val Ala Thr Pro Tyr Ile Asp
    115                 120                 125 agc gtg aac gaa cgc gaa aaa gaa ttt ctg gaa gcg aac ggc att gaa     432
Ser Val Asn Glu Arg Glu Lys Glu Phe Leu Glu Ala Asn Gly Ile Glu
                130                 135                 140 gtg ctg cgt att aaa ggc ctg ggc att gtg aaa aac acc gaa att ggc     480
Val Leu Arg Ile Lys Gly Leu Gly Ile Val Lys Asn Thr Glu Ile Gly
145                 150                 155                 160 cgt cag gaa ccg tgg gtt gcg tat aaa ctg gcc ctg gaa gtg tat acc     528
Arg Gln Glu Pro Trp Val Ala Tyr Lys Leu Ala Leu Glu Val Tyr Thr
```

```
            Arg Gln Glu Pro Trp Val Ala Tyr Lys Leu Ala Leu Glu Val Tyr Thr
                            165                 170                 175 ccg gaa gcg gat ggc ctg ttt att agc tgc acc aac ttt cgc acc att       576
Pro Glu Ala Asp Gly Leu Phe Ile Ser Cys Thr Asn Phe Arg Thr Ile
            180                 185                 190 gaa atc atc gat aaa ctg gaa gtg gaa ctg ggc gtg ccg gtg gtg acc       624
Glu Ile Ile Asp Lys Leu Glu Val Glu Leu Gly Val Pro Val Val Thr
        195                 200                 205 agc aac cag gcg acc atg tgg tat gcg ctg aaa acc atg aaa gtg aaa       672
Ser Asn Gln Ala Thr Met Trp Tyr Ala Leu Lys Thr Met Lys Val Lys
    210                 215                 220 gaa aaa tat gat atg tac ggc acc ctg ctg aaa gaa aaa ctc ctc gag       720
Glu Lys Tyr Asp Met Tyr Gly Thr Leu Leu Lys Glu Lys Leu Leu Glu
225                 230                 235                 240 cac cac cac cac cac cac                                               738
His His His His His His
                245

<210> SEQ ID NO 6
<211> LENGTH: 246
<212> TYPE: PRT
<213> ORGANISM: Pyrococcus horikoshii

<400> SEQUENCE: 6

Met Tyr Gly Trp Arg Arg Ile Gly Leu Ile Val Pro Ser Ser Asn
1               5                   10                  15

Thr Thr Met Glu Pro Glu Phe Trp Lys Met Ala Pro Glu Gly Val Ser
                20                  25                  30

Ile His Thr Ala Arg Met Arg Leu Arg Glu Val Thr Glu Ser Leu
            35                  40                  45

Leu Glu Met Glu Arg His Ala Lys Asp Ala Ala Leu Glu Leu Ala Asp
    50                  55                  60

Ala Glu Val Asp Val Ile Val Tyr Gly Cys Thr Ser Gly Ser Leu Ile
65                  70                  75                  80

Lys Gly Lys Gly Tyr Asp Lys Glu Ile Ala Lys Asn Leu Glu Glu Ala
                85                  90                  95

Ser Gly Ile Lys Thr Ile Thr Thr Ser Thr Ala Val Leu Asn Ala Leu
            100                 105                 110

Asn Thr Leu Asp Ile Gln Lys Val Val Val Ala Thr Pro Tyr Ile Asp
    115                 120                 125

Ser Val Asn Glu Arg Glu Lys Glu Phe Leu Glu Ala Asn Gly Ile Glu
130                 135                 140

Val Leu Arg Ile Lys Gly Leu Gly Ile Val Lys Asn Thr Glu Ile Gly
145                 150                 155                 160

Arg Gln Glu Pro Trp Val Ala Tyr Lys Leu Ala Leu Glu Val Tyr Thr
                165                 170                 175

Pro Glu Ala Asp Gly Leu Phe Ile Ser Cys Thr Asn Phe Arg Thr Ile
            180                 185                 190

Glu Ile Ile Asp Lys Leu Glu Val Glu Leu Gly Val Pro Val Val Thr
    195                 200                 205

Ser Asn Gln Ala Thr Met Trp Tyr Ala Leu Lys Thr Met Lys Val Lys
210                 215                 220

Glu Lys Tyr Asp Met Tyr Gly Thr Leu Leu Lys Glu Lys Leu Leu Glu
225                 230                 235                 240

His His His His His His
                245
```

<210> SEQ ID NO 7
<211> LENGTH: 819
<212> TYPE: DNA
<213> ORGANISM: Bordetella bronchiseptica
<220> FEATURE:
<221> NAME/KEY: CDS
<222> LOCATION: (1)..(819)

<400> SEQUENCE: 7

```
atg ccg acc ccg acc cag atg aaa acc acc gcg cgt tat cgt ccg tat    48
Met Pro Thr Pro Thr Gln Met Lys Thr Thr Ala Arg Tyr Arg Pro Tyr
1               5                  10                  15 gcg tgg cgt gcg aaa gtg ggc ctg att gtg ccg agc acc aac acc att    96
Ala Trp Arg Ala Lys Val Gly Leu Ile Val Pro Ser Thr Asn Thr Ile
            20                  25                  30 aac gaa ccg gaa ttc tat cgt ctg gcc ccg gat ggc gtg acc att cat   144
Asn Glu Pro Glu Phe Tyr Arg Leu Ala Pro Asp Gly Val Thr Ile His
        35                  40                  45 acc ggc cgt gcg att aat gcg ggt ccg gcg acc caa gaa aac tat gat   192
Thr Gly Arg Ala Ile Asn Ala Gly Pro Ala Thr Gln Glu Asn Tyr Asp
    50                  55                  60 cgt atg gcg cgt ggc gtt ctg gaa gcg gcg gat ctg att aaa acc gcg   240
Arg Met Ala Arg Gly Val Leu Glu Ala Ala Asp Leu Ile Lys Thr Ala
65                  70                  75                  80 gaa gtg gat gtg gtg gcg tat ggc tgc acc agc ggc agc att gtg tgc   288
Glu Val Asp Val Val Ala Tyr Gly Cys Thr Ser Gly Ser Ile Val Cys
                85                  90                  95 agc ctg gat gaa ctg tgc gat ggc atg agc gaa cgt gtg ggc gtt ccg   336
Ser Leu Asp Glu Leu Cys Asp Gly Met Ser Glu Arg Val Gly Val Pro
            100                 105                 110 gcg att gcg acc gcg ggt gcg gtt gtt gcg gcg ctg cgt gcg ctg ggt   384
Ala Ile Ala Thr Ala Gly Ala Val Val Ala Ala Leu Arg Ala Leu Gly
        115                 120                 125 gtt cgt cgt gtg gcg gtg ggc acc ccg tat att gat ttt gtg aac cag   432
Val Arg Arg Val Ala Val Gly Thr Pro Tyr Ile Asp Phe Val Asn Gln
    130                 135                 140 cgt gaa cgt gaa ttt ctg gaa cag tat ggc ttt gaa gtg gtg agc att   480
Arg Glu Arg Glu Phe Leu Glu Gln Tyr Gly Phe Glu Val Val Ser Ile
145                 150                 155                 160 gaa ggc atg gat ctg ggc cat acg cag gaa gaa cgt cgc gat att ggc   528
Glu Gly Met Asp Leu Gly His Thr Gln Glu Glu Arg Arg Asp Ile Gly
                165                 170                 175 cgt gtg ccg ccg cag agc acc ttt cag ctg gcc cgt gat att gat cgt   576
Arg Val Pro Pro Gln Ser Thr Phe Gln Leu Ala Arg Asp Ile Asp Arg
            180                 185                 190 ccg cag gcg gaa gcg att ttt ctg agc tgc acc aac ctg gcc acc ctg   624
Pro Gln Ala Glu Ala Ile Phe Leu Ser Cys Thr Asn Leu Ala Thr Leu
        195                 200                 205 gat atg att gaa cgc atc gaa aac gaa ctg ggc aaa ccg gtg gtg acc   672
Asp Met Ile Glu Arg Ile Glu Asn Glu Leu Gly Lys Pro Val Val Thr
    210                 215                 220 agc aac cag gcg acc ttt tgg gcg tgc ctg cgt ctg ctg ggt ctg agc   720
Ser Asn Gln Ala Thr Phe Trp Ala Cys Leu Arg Leu Leu Gly Leu Ser
225                 230                 235                 240 tgc gcg att ccg ggc tat ggc cgt ctg ctg acc gat tgc ctg gcc ccg   768
Cys Ala Ile Pro Gly Tyr Gly Arg Leu Leu Thr Asp Cys Leu Ala Pro
                245                 250                 255 att acc cgt gcg agc tat gcg ctg gcc ctc gag cac cac cac cac cac   816
Ile Thr Arg Ala Ser Tyr Ala Leu Ala Leu Glu His His His His His
            260                 265                 270
```

```
cac                                                                      819
His
```

<210> SEQ ID NO 8
<211> LENGTH: 273
<212> TYPE: PRT
<213> ORGANISM: Bordetella bronchiseptica

<400> SEQUENCE: 8

```
Met Pro Thr Pro Thr Gln Met Lys Thr Thr Ala Arg Tyr Arg Pro Tyr
1               5                   10                  15

Ala Trp Arg Ala Lys Val Gly Leu Ile Val Pro Ser Thr Asn Thr Ile
            20                  25                  30

Asn Glu Pro Glu Phe Tyr Arg Leu Ala Pro Asp Gly Val Thr Ile His
        35                  40                  45

Thr Gly Arg Ala Ile Asn Ala Gly Pro Ala Thr Gln Glu Asn Tyr Asp
    50                  55                  60

Arg Met Ala Arg Gly Val Leu Glu Ala Ala Asp Leu Ile Lys Thr Ala
65                  70                  75                  80

Glu Val Asp Val Val Ala Tyr Gly Cys Thr Ser Gly Ser Ile Val Cys
                85                  90                  95

Ser Leu Asp Glu Leu Cys Asp Gly Met Ser Glu Arg Val Gly Val Pro
            100                 105                 110

Ala Ile Ala Thr Ala Gly Ala Val Val Ala Ala Leu Arg Ala Leu Gly
        115                 120                 125

Val Arg Arg Val Ala Val Gly Thr Pro Tyr Ile Asp Phe Val Asn Gln
    130                 135                 140

Arg Glu Arg Glu Phe Leu Glu Gln Tyr Gly Phe Glu Val Val Ser Ile
145                 150                 155                 160

Glu Gly Met Asp Leu Gly His Thr Gln Glu Glu Arg Arg Asp Ile Gly
                165                 170                 175

Arg Val Pro Pro Gln Ser Thr Phe Gln Leu Ala Arg Asp Ile Asp Arg
            180                 185                 190

Pro Gln Ala Glu Ala Ile Phe Leu Ser Cys Thr Asn Leu Ala Thr Leu
        195                 200                 205

Asp Met Ile Glu Arg Ile Glu Asn Glu Leu Gly Lys Pro Val Val Thr
    210                 215                 220

Ser Asn Gln Ala Thr Phe Trp Ala Cys Leu Arg Leu Leu Gly Leu Ser
225                 230                 235                 240

Cys Ala Ile Pro Gly Tyr Gly Arg Leu Leu Thr Asp Cys Leu Ala Pro
                245                 250                 255

Ile Thr Arg Ala Ser Tyr Ala Leu Ala Leu Glu His His His His His
            260                 265                 270

His
```

<210> SEQ ID NO 9
<211> LENGTH: 756
<212> TYPE: DNA
<213> ORGANISM: Alkaliphilus metalliredigenes
<220> FEATURE:
<221> NAME/KEY: CDS
<222> LOCATION: (1)..(756)

<400> SEQUENCE: 9

```
atg agc gat ttt agc tat ggc ggc cgt gcg aaa att ggc ctg att tat     48
Met Ser Asp Phe Ser Tyr Gly Gly Arg Ala Lys Ile Gly Leu Ile Tyr
1               5                   10                  15
```

| | | |
|---|---|---|
| ccg gca ccg ggc tgg gtt atg gaa ccg gaa ttc tat ctg atg gcg ccg<br>Pro Ala Pro Gly Trp Val Met Glu Pro Glu Phe Tyr Leu Met Ala Pro<br>20          25              30 | | 96 |
| tgg ggc gtg agc acc tat acc acc cgt att agc ctg aaa cat gtg aac<br>Trp Gly Val Ser Thr Tyr Thr Thr Arg Ile Ser Leu Lys His Val Asn<br>    35              40              45 | | 144 |
| gtg gcg gaa ctg cgt aaa ctg ggc gat cag agc gtg gaa gcg gcg gaa<br>Val Ala Glu Leu Arg Lys Leu Gly Asp Gln Ser Val Glu Ala Ala Glu<br>50              55              60 | | 192 |
| ctg ctg gcc cag gcg ccg ctg gat gtg att gcg ctg ggc tgc acc agc<br>Leu Leu Ala Gln Ala Pro Leu Asp Val Ile Ala Leu Gly Cys Thr Ser<br>65              70              75              80 | | 240 |
| ggc agc ttc gtg aac ggc agc cgt tat gat caa gaa ctg atc gaa aaa<br>Gly Ser Phe Val Asn Gly Ser Arg Tyr Asp Gln Glu Leu Ile Glu Lys<br>            85              90              95 | | 288 |
| atg gaa ggc gtg agc ggc ggt att ccg tgc acc acc acc tct acc gcg<br>Met Glu Gly Val Ser Gly Gly Ile Pro Cys Thr Thr Thr Ser Thr Ala<br>100             105             110 | | 336 |
| gtt gtg gcg gcg ctg aaa gcg ctg cat gtg acc aaa att gcg gtg gcg<br>Val Val Ala Ala Leu Lys Ala Leu His Val Thr Lys Ile Ala Val Ala<br>        115             120             125 | | 384 |
| acc ccg tat atc gat gaa gtg aac ctg aaa gcg aaa aac ttt ctg gaa<br>Thr Pro Tyr Ile Asp Glu Val Asn Leu Lys Ala Lys Asn Phe Leu Glu<br>130             135             140 | | 432 |
| gcg gaa ggc ctg gat gtg gtg aac att aaa ggc ctg ggc ctg ctg cag<br>Ala Glu Gly Leu Asp Val Val Asn Ile Lys Gly Leu Gly Leu Leu Gln<br>145             150             155             160 | | 480 |
| gat att gaa att gat cgc cag gat atg gaa acc gtg tat cgt ctg gcc<br>Asp Ile Glu Ile Asp Arg Gln Asp Met Glu Thr Val Tyr Arg Leu Ala<br>                165             170             175 | | 528 |
| aaa gaa gtg gat cac gtt gaa gcg cag gcg att gtg att ctg tgc acc<br>Lys Glu Val Asp His Val Glu Ala Gln Ala Ile Val Ile Leu Cys Thr<br>            180             185             190 | | 576 |
| ggc ctg cgt agc gtg ccg att att gaa gcg ctg gaa aac gat ctg ggc<br>Gly Leu Arg Ser Val Pro Ile Ile Glu Ala Leu Glu Asn Asp Leu Gly<br>        195             200             205 | | 624 |
| aaa ccg gtg att agc gcg att cag gcg acc ttt tgg cat tgc ctg cgt<br>Lys Pro Val Ile Ser Ala Ile Gln Ala Thr Phe Trp His Cys Leu Arg<br>210             215             220 | | 672 |
| ctg agc ggc gtg cgt gaa aac gtg gaa ggc tat ggc agc ctg ctg cgt<br>Leu Ser Gly Val Arg Glu Asn Val Glu Gly Tyr Gly Ser Leu Leu Arg<br>225             230             235             240 | | 720 |
| att gaa ggc ctg ctc gag cac cac cac cac cac cac<br>Ile Glu Gly Leu Leu Glu His His His His His His<br>                245             250 | | 756 |

<210> SEQ ID NO 10
<211> LENGTH: 252
<212> TYPE: PRT
<213> ORGANISM: Alkaliphilus metalliredigenes

<400> SEQUENCE: 10

Met Ser Asp Phe Ser Tyr Gly Gly Arg Ala Lys Ile Gly Leu Ile Tyr
1               5                   10                  15

Pro Ala Pro Gly Trp Val Met Glu Pro Glu Phe Tyr Leu Met Ala Pro
            20                  25                  30

Trp Gly Val Ser Thr Tyr Thr Thr Arg Ile Ser Leu Lys His Val Asn
        35                  40                  45

Val Ala Glu Leu Arg Lys Leu Gly Asp Gln Ser Val Glu Ala Ala Glu
    50                  55                  60

```
Leu Leu Ala Gln Ala Pro Leu Asp Val Ile Ala Leu Gly Cys Thr Ser
 65                  70                  75                  80

Gly Ser Phe Val Asn Gly Ser Arg Tyr Asp Gln Glu Leu Ile Glu Lys
                 85                  90                  95

Met Glu Gly Val Ser Gly Gly Ile Pro Cys Thr Thr Thr Ser Thr Ala
            100                 105                 110

Val Val Ala Ala Leu Lys Ala Leu His Val Thr Lys Ile Ala Val Ala
        115                 120                 125

Thr Pro Tyr Ile Asp Glu Val Asn Leu Lys Ala Lys Asn Phe Leu Glu
130                 135                 140

Ala Glu Gly Leu Asp Val Val Asn Ile Lys Gly Leu Gly Leu Leu Gln
145                 150                 155                 160

Asp Ile Glu Ile Asp Arg Gln Asp Met Glu Thr Val Tyr Arg Leu Ala
                165                 170                 175

Lys Glu Val Asp His Val Glu Ala Gln Ala Ile Val Ile Leu Cys Thr
            180                 185                 190

Gly Leu Arg Ser Val Pro Ile Ile Glu Ala Leu Glu Asn Asp Leu Gly
        195                 200                 205

Lys Pro Val Ile Ser Ala Ile Gln Ala Thr Phe Trp His Cys Leu Arg
210                 215                 220

Leu Ser Gly Val Arg Glu Asn Val Glu Gly Tyr Gly Ser Leu Leu Arg
225                 230                 235                 240

Ile Glu Gly Leu Leu Glu His His His His His His
                245                 250

<210> SEQ ID NO 11
<211> LENGTH: 786
<212> TYPE: DNA
<213> ORGANISM: Aquifex pyrophilus
<220> FEATURE:
<221> NAME/KEY: CDS
<222> LOCATION: (1)..(786)

<400> SEQUENCE: 11 atg aaa atc ggc att ttt gat agc ggc gtg ggc ggt ctg acc gtg ctg      48
Met Lys Ile Gly Ile Phe Asp Ser Gly Val Gly Gly Leu Thr Val Leu
 1               5                  10                  15 aaa gcg att cgt aac cgt tat cgc aaa gtg gat att gtg tat ctg ggc      96
Lys Ala Ile Arg Asn Arg Tyr Arg Lys Val Asp Ile Val Tyr Leu Gly
            20                  25                  30 gat acc gcg cgt gtg ccg tat ggc att cgt agc aaa gat acc att atc     144
Asp Thr Ala Arg Val Pro Tyr Gly Ile Arg Ser Lys Asp Thr Ile Ile
        35                  40                  45 cgc tat agc ctg gaa tgc gcg ggc ttt ctg aaa gat aaa ggc gtg gat     192
Arg Tyr Ser Leu Glu Cys Ala Gly Phe Leu Lys Asp Lys Gly Val Asp
 50                  55                  60 att att gtg gtg gcg tgt aac acc gcg agc gcg tat gcg ctg gaa cgt     240
Ile Ile Val Val Ala Cys Asn Thr Ala Ser Ala Tyr Ala Leu Glu Arg
 65                  70                  75                  80 ctg aaa aaa gag atc aac gtt ccg gtt ttt ggc gtg att gaa ccg ggc     288
Leu Lys Lys Glu Ile Asn Val Pro Val Phe Gly Val Ile Glu Pro Gly
                 85                  90                  95 gtg aaa gaa gcg ctg aaa aaa agc cgc aac aaa aaa att ggt gtg att     336
Val Lys Glu Ala Leu Lys Lys Ser Arg Asn Lys Lys Ile Gly Val Ile
            100                 105                 110 ggc acc ccg gcg acc gtt aaa agc ggc gcg tat cag cgt aaa ctg gaa     384
Gly Thr Pro Ala Thr Val Lys Ser Gly Ala Tyr Gln Arg Lys Leu Glu
        115                 120                 125
```

```
gaa ggc ggt gcg gat gtt ttt gcg aaa gcg tgc ccg ctg ttt gtg ccg      432
Glu Gly Gly Ala Asp Val Phe Ala Lys Ala Cys Pro Leu Phe Val Pro
130                 135                 140 ctg gcc gaa gaa ggc ctg ctg gaa ggc gaa att acc cgt aaa gtg gtg      480
Leu Ala Glu Glu Gly Leu Leu Glu Gly Glu Ile Thr Arg Lys Val Val
145                 150                 155                 160 gaa cac tat ctg aaa gaa ttc aaa ggc aaa atc gat acc ctg att ctg      528
Glu His Tyr Leu Lys Glu Phe Lys Gly Lys Ile Asp Thr Leu Ile Leu
                165                 170                 175 ggc tgc acg cac tat ccg ctg ctg aaa aaa gaa atc aaa aaa ttc ctg      576
Gly Cys Thr His Tyr Pro Leu Leu Lys Lys Glu Ile Lys Lys Phe Leu
            180                 185                 190 ggc gat gtg gaa gtg gtg gat agc agc gaa gcc ctg agc ctg agc ctg      624
Gly Asp Val Glu Val Val Asp Ser Ser Glu Ala Leu Ser Leu Ser Leu
        195                 200                 205 cat aac ttc att aaa gat gat ggc agc agc agc ctg gaa ctg ttt ttt      672
His Asn Phe Ile Lys Asp Asp Gly Ser Ser Ser Leu Glu Leu Phe Phe
    210                 215                 220 acc gat ctg agc ccg aac ctg cag ttt ctg att aaa ctg att ctg ggt      720
Thr Asp Leu Ser Pro Asn Leu Gln Phe Leu Ile Lys Leu Ile Leu Gly
225                 230                 235                 240 cgt gat tat ccg gtg aaa ctg gcc gaa ggc gtg ttt acc cat ctc gag      768
Arg Asp Tyr Pro Val Lys Leu Ala Glu Gly Val Phe Thr His Leu Glu
                245                 250                 255 cac cac cac cac cac cac                                              786
His His His His His His
                260
```

<210> SEQ ID NO 12
<211> LENGTH: 262
<212> TYPE: PRT
<213> ORGANISM: Aquifex pyrophilus

<400> SEQUENCE: 12

```
Met Lys Ile Gly Ile Phe Asp Ser Gly Val Gly Gly Leu Thr Val Leu
1               5                   10                  15

Lys Ala Ile Arg Asn Arg Tyr Arg Lys Val Asp Ile Val Tyr Leu Gly
            20                  25                  30

Asp Thr Ala Arg Val Pro Tyr Gly Ile Arg Ser Lys Asp Thr Ile Ile
        35                  40                  45

Arg Tyr Ser Leu Glu Cys Ala Gly Phe Leu Lys Asp Lys Gly Val Asp
    50                  55                  60

Ile Ile Val Val Ala Cys Asn Thr Ala Ser Ala Tyr Ala Leu Glu Arg
65                  70                  75                  80

Leu Lys Lys Glu Ile Asn Val Pro Val Phe Gly Val Ile Glu Pro Gly
                85                  90                  95

Val Lys Glu Ala Leu Lys Lys Ser Arg Asn Lys Lys Ile Gly Val Ile
            100                 105                 110

Gly Thr Pro Ala Thr Val Lys Ser Gly Ala Tyr Gln Arg Lys Leu Glu
        115                 120                 125

Glu Gly Gly Ala Asp Val Phe Ala Lys Ala Cys Pro Leu Phe Val Pro
    130                 135                 140

Leu Ala Glu Glu Gly Leu Leu Glu Gly Glu Ile Thr Arg Lys Val Val
145                 150                 155                 160

Glu His Tyr Leu Lys Glu Phe Lys Gly Lys Ile Asp Thr Leu Ile Leu
                165                 170                 175

Gly Cys Thr His Tyr Pro Leu Leu Lys Lys Glu Ile Lys Lys Phe Leu
```

```
                    180                 185                 190
Gly Asp Val Glu Val Val Asp Ser Ser Glu Ala Leu Ser Leu Ser Leu
            195                 200                 205

His Asn Phe Ile Lys Asp Asp Gly Ser Ser Ser Leu Glu Leu Phe Phe
        210                 215                 220

Thr Asp Leu Ser Pro Asn Leu Gln Phe Leu Ile Lys Leu Ile Leu Gly
225                 230                 235                 240

Arg Asp Tyr Pro Val Lys Leu Ala Glu Gly Val Phe Thr His Leu Glu
                245                 250                 255

His His His His His His
        260

<210> SEQ ID NO 13
<211> LENGTH: 4
<212> TYPE: PRT
<213> ORGANISM: Artificial sequence
<220> FEATURE:
<223> OTHER INFORMATION: CS sequence pattern
<220> FEATURE:
<221> NAME/KEY: MISC_FEATURE
<222> LOCATION: (1)..(1)
<223> OTHER INFORMATION: Xaa is  Ser or Leu
<220> FEATURE:
<221> NAME/KEY: MISC_FEATURE
<222> LOCATION: (3)..(3)
<223> OTHER INFORMATION: Xaa is  Gly or Thr
<220> FEATURE:
<221> NAME/KEY: MISC_FEATURE
<222> LOCATION: (4)..(4)
<223> OTHER INFORMATION: Xaa is  Gyl or Asn

<400> SEQUENCE: 13

Xaa Cys Xaa Xaa
1

<210> SEQ ID NO 14
<211> LENGTH: 5
<212> TYPE: PRT
<213> ORGANISM: Artificial sequence
<220> FEATURE:
<223> OTHER INFORMATION: OAH1 sequence pattern
<220> FEATURE:
<221> NAME/KEY: MISC_FEATURE
<222> LOCATION: (1)..(1)
<223> OTHER INFORMATION: Xaa is Met or Gly
<220> FEATURE:
<221> NAME/KEY: MISC_FEATURE
<222> LOCATION: (2)..(2)
<223> OTHER INFORMATION: Xaa is Cys or Gly
<220> FEATURE:
<221> NAME/KEY: MISC_FEATURE
<222> LOCATION: (5)..(5)
<223> OTHER INFORMATION: Xaa is Leu or Gly

<400> SEQUENCE: 14

Xaa Xaa Thr Ser Xaa
1               5

<210> SEQ ID NO 15
<211> LENGTH: 5
<212> TYPE: PRT
<213> ORGANISM: Artificial sequence
<220> FEATURE:
<223> OTHER INFORMATION: OAH2 sequence pattern
<220> FEATURE:
<221> NAME/KEY: MISC_FEATURE
<222> LOCATION: (1)..(1)
<223> OTHER INFORMATION: Thr is optionally missing
<220> FEATURE:
```

```
<221> NAME/KEY: MISC_FEATURE
<222> LOCATION: (2)..(2)
<223> OTHER INFORMATION: Xaa is Ala or Pro
<220> FEATURE:
<221> NAME/KEY: MISC_FEATURE
<222> LOCATION: (4)..(4)
<223> OTHER INFORMATION: Xaa is Ile or Arg
<220> FEATURE:
<221> NAME/KEY: MISC_FEATURE
<222> LOCATION: (5)..(5)
<223> OTHER INFORMATION: Xaa is Asp or Gln or missing

<400> SEQUENCE: 15

Thr Xaa Tyr Xaa Xaa
1               5

<210> SEQ ID NO 16
<211> LENGTH: 6
<212> TYPE: PRT
<213> ORGANISM: Artificial sequence
<220> FEATURE:
<223> OTHER INFORMATION: LBP sequence pattern
<220> FEATURE:
<221> NAME/KEY: MISC_FEATURE
<222> LOCATION: (4)..(4)
<223> OTHER INFORMATION: Xaa is Phe, Ser or Ala
<220> FEATURE:
<221> NAME/KEY: MISC_FEATURE
<222> LOCATION: (5)..(5)
<223> OTHER INFORMATION: Xaa is Phe, Ser, Thr or Ala
<220> FEATURE:
<221> NAME/KEY: MISC_FEATURE
<222> LOCATION: (6)..(6)
<223> OTHER INFORMATION: Xaa is Ala, Asn or Gly

<400> SEQUENCE: 16

Ile Val Pro Xaa Xaa Xaa
1               5

<210> SEQ ID NO 17
<211> LENGTH: 27
<212> TYPE: DNA
<213> ORGANISM: Artificial sequence
<220> FEATURE:
<223> OTHER INFORMATION: forward primer

<400> SEQUENCE: 17
gagcggcctg ggcgcgggta gcgttac                                    27

<210> SEQ ID NO 18
<211> LENGTH: 27
<212> TYPE: DNA
<213> ORGANISM: Artificial sequence
<220> FEATURE:
<223> OTHER INFORMATION: Reverse Primer

<400> SEQUENCE: 18
gtaacgctac ccgcgcccag gccgctc                                    27

<210> SEQ ID NO 19
<211> LENGTH: 25
<212> TYPE: DNA
<213> ORGANISM: Artificial sequence
<220> FEATURE:
<223> OTHER INFORMATION: Forward Primer

<400> SEQUENCE: 19
cctgggtagc gcaaccccgg aaggc                                      25
```

```
<210> SEQ ID NO 20
<211> LENGTH: 25
<212> TYPE: DNA
<213> ORGANISM: Artificial sequence
<220> FEATURE:
<223> OTHER INFORMATION: Reverse Primer

<400> SEQUENCE: 20
gccttccggg gttgcgctac ccagg                                          25

<210> SEQ ID NO 21
<211> LENGTH: 25
<212> TYPE: DNA
<213> ORGANISM: Artificial sequence
<220> FEATURE:
<223> OTHER INFORMATION: Forward Primer

<400> SEQUENCE: 21
gcattaccgg cgcggaagcg atggc                                          25

<210> SEQ ID NO 22
<211> LENGTH: 25
<212> TYPE: DNA
<213> ORGANISM: Artificial sequence
<220> FEATURE:
<223> OTHER INFORMATION: Reverse Primer

<400> SEQUENCE: 22
gccatcgctt ccgcgccggt aatgc                                          25

<210> SEQ ID NO 23
<211> LENGTH: 32
<212> TYPE: DNA
<213> ORGANISM: Artificial sequence
<220> FEATURE:
<223> OTHER INFORMATION: PCR Primer

<400> SEQUENCE: 23
cattggcatg attgtggcgc cggcagcggg tc                                  32

<210> SEQ ID NO 24
<211> LENGTH: 32
<212> TYPE: DNA
<213> ORGANISM: Artificial sequence
<220> FEATURE:
<223> OTHER INFORMATION: PCR Primer

<400> SEQUENCE: 24
gacccgctgc cggcgccaca atcatgccaa tg                                  32

<210> SEQ ID NO 25
<211> LENGTH: 34
<212> TYPE: DNA
<213> ORGANISM: Artificial sequence
<220> FEATURE:
<223> OTHER INFORMATION: PCR primer

<400> SEQUENCE: 25
cattggcatg attgtgggtc cggcagcggg tctg                                34

<210> SEQ ID NO 26
<211> LENGTH: 34
<212> TYPE: DNA
<213> ORGANISM: Artificial sequence
<220> FEATURE:
<223> OTHER INFORMATION: PCR Primer
```

```
<400> SEQUENCE: 26
cagacccgct gccggaccca caatcatgcc aatg                                34

<210> SEQ ID NO 27
<211> LENGTH: 27
<212> TYPE: DNA
<213> ORGANISM: Artificial sequence
<220> FEATURE:
<223> OTHER INFORMATION: PCR primer

<400> SEQUENCE: 27
ctgctgtctt gcgcgggtct gctgacc                                        27

<210> SEQ ID NO 28
<211> LENGTH: 27
<212> TYPE: DNA
<213> ORGANISM: Artificial sequence
<220> FEATURE:
<223> OTHER INFORMATION: PCR primer

<400> SEQUENCE: 28
ggtcagcaga cccgcgcaag acagcag                                        27

<210> SEQ ID NO 29
<211> LENGTH: 34
<212> TYPE: DNA
<213> ORGANISM: Artificial sequence
<220> FEATURE:
<223> OTHER INFORMATION: PCR primer

<400> SEQUENCE: 29
ctgctgtctt gcggcgcgct gctgaccctg gatg                                34

<210> SEQ ID NO 30
<211> LENGTH: 34
<212> TYPE: DNA
<213> ORGANISM: Artificial sequence
<220> FEATURE:
<223> OTHER INFORMATION: PCR primer

<400> SEQUENCE: 30
catccagggt cagcagcgcg ccgcaagaca gcag                                34

<210> SEQ ID NO 31
<211> LENGTH: 38
<212> TYPE: DNA
<213> ORGANISM: Artificial sequence
<220> FEATURE:
<223> OTHER INFORMATION: PCR primer

<400> SEQUENCE: 31
cattctgctg tcttgcgcgg cgctgctgac cctggatg                            38

<210> SEQ ID NO 32
<211> LENGTH: 38
<212> TYPE: DNA
<213> ORGANISM: Artificial sequence
<220> FEATURE:
<223> OTHER INFORMATION: PCR primer

<400> SEQUENCE: 32
catccagggt cagcagcgcc gcgcaagaca gcagaatg                            38

<210> SEQ ID NO 33
<211> LENGTH: 45
```

```
<212> TYPE: DNA
<213> ORGANISM: Artificial sequence
<220> FEATURE:
<223> OTHER INFORMATION: PCR primer
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t

<400> SEQUENCE: 33
ccccgaccat tggcatgatt ndtndtccgg cagcgggtct ggttc          45

<210> SEQ ID NO 34
<211> LENGTH: 45
<212> TYPE: DNA
<213> ORGANISM: Artificial sequence
<220> FEATURE:
<223> OTHER INFORMATION: PCR primer
<220> FEATURE:
<221> NAME/KEY: misc_feature
<222> LOCATION: (22)..(22)
<223> OTHER INFORMATION: n is a, c, g, or t
<220> FEATURE:
<221> NAME/KEY: misc_feature
<222> LOCATION: (25)..(25)
<223> OTHER INFORMATION: n is a, c, g, or t

<400> SEQUENCE: 34
gaaccagacc cgctgccgga hnahnaatca tgccaatggt cgggg          45

<210> SEQ ID NO 35
<211> LENGTH: 45
<212> TYPE: DNA
<213> ORGANISM: Artificial sequence
<220> FEATURE:
<223> OTHER INFORMATION: PCR primer
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t

<400> SEQUENCE: 35
cgaccattgg catgattgtg ndtndtgcag cgggtctggt tccgg          45

<210> SEQ ID NO 36
<211> LENGTH: 45
<212> TYPE: DNA
<213> ORGANISM: Artificial sequence
<220> FEATURE:
<223> OTHER INFORMATION: PCR primer
<220> FEATURE:
<221> NAME/KEY: misc_feature
<222> LOCATION: (22)..(22)
<223> OTHER INFORMATION: n is a, c, g, or t
<220> FEATURE:
<221> NAME/KEY: misc_feature
<222> LOCATION: (25)..(25)
<223> OTHER INFORMATION: n is a, c, g, or t

<400> SEQUENCE: 36
ccggaaccag acccgctgca hnahncacaa tcatgccaat ggtcg          45
```

The invention claimed is:

1. A method for decarboxylating a compound of formula I $$HOOC-C(R^1)(R^2)-COOH \quad (I)$$

or a salt form thereof,
wherein $R^1$ represents a linear or branched, mono-unsaturated $C_2$-$C_8$-alkenyl group; and
$R^2$ represents H, OH, SH, $NH_2$, $C_1$-$C_8$-alkoxy, $C_1$-$C_8$-alkylthio, $C_1$-$C_8$-alkyl, $C_2$-$C_8$-alkenyl, $C_2$-$C_8$-alkynyl or hydroxyl $C_1$-$C_8$-alkyl, comprising
a) contacting the compound of formula I with a protein having decarboxylase activity; and
b) isolating a decarboxylation product of the compound of the formula I,
wherein the protein having decarboxylase activity comprises an amino acid sequence having at least 95% sequence identity to residues 1 to 240 of the *Bordetella bronchiseptica* polypeptide of SEQ ID NO: 2 and comprises a functional mutation in one of the amino acid sequence positions 14, 189 and 190 of the polypeptide of SEQ ID NO: 2.

2. The method of claim 1, wherein said decarboxylase activity is a stereo-selective mono-decarboxylase activity.

3. The method of claim 2, wherein said decarboxylation product is an optically pure compound of formula II $$HC(R^1)(R^2)-COOH \quad (II)$$

or a salt form thereof,
wherein $R^1$ represents a linear or branched, mono-unsaturated $C_2$-$C_8$-alkenyl group; and
$R^2$ represents H, OH, SH, $NH_2$, $C_1$-$C_8$-alkoxy, $C_1$-$C_8$-alkylthio, $C_1$-$C_8$-alkyl, $C_2$-$C_8$-alkenyl, $C_2$-$C_8$-alkynyl or hydroxyl $C_1$-$C_8$-alkyl.

4. The method of claim 1, wherein said decarboxylation is performed with the decarboxylase in isolated or purified, and, optionally, immobilized form, or by culturing a microorganism expressing the decarboxylase activity in the presence of a compound of the formula I.

5. The method of claim 1, wherein $R^1$ represents a linear or branched mono-unsaturated $C_2$-$C_8$-alkenyl group and $R^2$ is a $C_1$-$C_8$-alkyl group.

6. The method of claim 5, wherein $R^1$ represents a linear $C_1$-$C_6$-alken-1-yl group and $R^2$ is a $C_1$-$C_6$-alkyl group.

7. The method of claim 6, wherein $R^1$ represents, ethenyl, or propen-1-yl, buten-1-yl.

8. A method for the biocatalytic decarboxylation of a compound of formula I, $$HOOC-C(R^1)(R^2)-COOH \quad (I)$$

or a salt form thereof,
wherein $R^1$ represents a linear or branched, mono-unsaturated $C_2$-$C_8$-alkenyl group; and
$R^2$ represents H, OH, SH, $NH_2$, $C_1$-$C_8$-alkoxy, $C_1$-$C_8$-alkylthio, $C_1$-$C_8$-alkyl, $C_2$-$C_8$-alkenyl, $C_2$-$C_8$-alkynyl or hydroxyl $C_1$-$C_8$-alkyl,
wherein the method comprises
a) contacting a compound of the formula I with a protein having decarboxylase activity and comprising an amino acid sequence having at least 95% sequence identity to residues 1 to 240 of the *Bordetella bronchiseptica* polypeptide of SEQ ID NO: 2; and
b) isolating a decarboxylation product of a compound of the formula I,
wherein the amino acid sequence comprises a functional mutation in at least one amino acid position selected from the group consisting of positions 13, 14, 21, 40, 43, 48, 104, 126, 156, 159, 188, 189, 190, 191 and 212 of the polypeptide of SEQ ID NO: 2.

9. The method of claim 8, wherein said decarboxylase activity is a stereo-selective mono-decarboxylase activity.

10. The method of claim 9, wherein said decarboxylation product is an optically pure compound of formula II $$HC(R^1)(R^2)-COOH \quad (II)$$

or a salt form thereof,
wherein $R^1$ represents a linear or branched, mono-unsaturated $C_2$-$C_8$-alkenyl group; and
$R^2$ represents H, OH, SH, $NH_2$, $C_1$-$C_8$-alkoxy, $C_1$-$C_8$-alkylthio, $C_1$-$C_8$-alkyl, $C_2$-$C_8$-alkenyl, $C_2$-$C_8$-alkynyl or hydroxyl $C_1$-$C_8$-alkyl.

11. The method of claim 8, wherein said decarboxylation is performed with the decarboxylase in isolated or purified, and, optionally, immobilized form, or by culturing a microorganism expressing the decarboxylase activity in the presence of a compound of the formula I.

12. The method of claim 8, wherein $R^1$ represents a linear or branched mono-unsaturated $C_2$-$C_8$-alkenyl group and $R^2$ is a $C_1$-$C_8$-alkyl group.

13. The method of claim 12, wherein $R^1$ represents a linear $C_1$-$C_6$-alken-1-yl group and $R^2$ is a $C_1$-$C_6$-alkyl group.

14. The method of claim 13, wherein $R^1$ represents, ethenyl, or propen-1-yl, buten-1-yl.

15. A method for the biocatalytic decarboxylation of a compound of formula I, $$HOOC-C(R^1)(R^2)-COOH \quad (I)$$

or a salt form thereof,
wherein $R^1$ represents a linear or branched, mono-unsaturated $C_2$-$C_8$-alkenyl group; and
$R^2$ represents H, OH, SH, $NH_2$, $C_1$-$C_8$-alkoxy, $C_1$-$C_8$-alkylthio, $C_1$-$C_8$-alkyl, $C_2$-$C_8$-alkenyl, $C_2$-$C_8$-alkynyl or hydroxyl $C_1$-$C_8$-alkyl,
wherein the method comprises
a) contacting a compound of the formula I with a protein having decarboxylase activity and comprising an amino acid sequence having at least 95% sequence identity to residues 1 to 240 of the *Bordetella bronchiseptica* polypeptide of SEQ ID NO: 2; and
b) isolating a decarboxylation product of a compound of the formula I,
wherein the amino acid sequence comprises mutations in a combination of amino acid positions of the polypeptide of SEQ ID NO: 2 selected from the group consisting of positions:
13 and 14,
13 and 15,
14 and 15,
13, 14 and 15,
14, 15 and 189,
14, 15 and 190,
14, 15, 189 and 190,
13, 14, 15 and 189,
13, 14, 15 and 190,
13, 14, 15, 189 and 190
13, 14 and 191,
13, 15 and 191;
14, 15 and 191,
13, 14, 15 and 191,
14, 15, 189 and 191,
14, 15, 190 and 191,
14, 15, 189, 190 and 191,
13, 14, 15, 189 and 191,
13, 14, 15, 190 and 191, and
13, 14, 15, 189, 190 and 191.

16. The method of claim 15, wherein said decarboxylase activity is a stereo-selective mono-decarboxylase activity.

17. The method of claim 16, wherein said decarboxylation product is an optically pure compound of formula II $$HC(R^1)(R^2)-COOH \qquad (II)$$

or a salt form thereof, wherein $R^1$ represents a linear or branched, mono-unsaturated $C_2$-$C_8$-alkenyl group; and $R^2$ represents H, OH, SH, $NH_2$, $C_1$-$C_8$-alkoxy, $C_1$-$C_8$-alkylthio, $C_1$-$C_8$-alkyl, $C_2$-$C_8$-alkenyl, $C_2$-$C_8$-alkynyl or hydroxyl $C_1$-$C_8$-alkyl.

18. The method of claim 15, wherein said decarboxylation is performed with the decarboxylase in isolated or purified, and, optionally, immobilized form, or by culturing a microorganism expressing the decarboxylase activity in the presence of a compound of the formula I.

19. The method of claim 15, wherein $R^1$ represents a linear or branched mono-unsaturated $C_2$-$C_8$-alkenyl group and $R^2$ is a $C_1$-$C_8$-alkyl group.

20. The method of claim 19, wherein $R^1$ represents a linear $C_1$-$C_6$-alken-1-yl group and $R^2$ is a $C_1$-$C_6$-alkyl group.

21. The method of claim 20, wherein $R^1$ represents, ethenyl, or propen-1-yl, buten-1-yl.

\* \* \* \* \*